US012376737B1

(12) United States Patent
Piskun et al.

(10) Patent No.: US 12,376,737 B1
(45) Date of Patent: Aug. 5, 2025

(54) TISSUE RETRACTOR FOR MINIMALLY INVASIVE SURGERY

(71) Applicant: Boston Scientific Scimed, Inc., Maple Grove, MN (US)

(72) Inventors: Gregory Piskun, Delray Beach, FL (US); Brian Tang, Fremont, CA (US); Jeffrey P. Radziunas, Wallingford, CT (US); John To, Newark, CA (US); Mariel Fabro, San Francisco, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 261 days.

(21) Appl. No.: 17/968,331

(22) Filed: Oct. 18, 2022

Related U.S. Application Data

(63) Continuation of application No. 16/688,453, filed on Nov. 19, 2019, now Pat. No. 11,471,026, which is a
(Continued)

(51) Int. Cl.
*A61B 1/00* (2006.01)
*A61B 1/018* (2006.01)
(Continued)

(52) U.S. Cl.
CPC ...... *A61B 1/00154* (2013.01); *A61B 1/00066* (2013.01); *A61B 1/00082* (2013.01);
(Continued)

(58) Field of Classification Search
CPC .............. A61B 17/0218; A61B 1/2736; A61B 1/00085; A61B 1/00154; A61B 1/32
See application file for complete search history.

(56) References Cited

U.S. PATENT DOCUMENTS

| 457,787 A | 8/1891 | Leisenring |
|---|---|---|
| 827,193 A | 7/1906 | Thrash |

(Continued)

FOREIGN PATENT DOCUMENTS

| CA | 2939211 A1 | 8/2015 |
|---|---|---|
| CN | 1579352 A | 2/2005 |

(Continued)

OTHER PUBLICATIONS

International Search Report and Written Opinion dated May 6, 2016 for International Application No. PCT/US2016/016911.
(Continued)

*Primary Examiner* — Olivia C Chang
(74) *Attorney, Agent, or Firm* — Seager, Tufte & Wickhem, LLP

(57) ABSTRACT

Improved methods and devices for performing an endoscopic surgery including a system for performing minimally invasive procedures including a flexible catheter having a first lumen, a first flexible tube positioned in the first lumen, and a second flexible tube positioned in the first lumen. The first lumen defines a first space configured and dimensioned to receive an endoscope. The first flexible tube and second flexible tube are fixed at a proximal portion and configured to float within the first lumen of the catheter. First and second flexible guides are slidably positioned within the first and second flexible tubes and dimensioned to receive a first instrument for axial movement therein, the first and second flexible guides movable to an angled position with respect to a longitudinal axis. A working space expanding system positioned at a distal portion of the flexible catheter, the working space expanding system movable from a non-expanded insertion position to an expanded position forming an expanded region to expand the working space within the body lumen.

17 Claims, 48 Drawing Sheets

Related U.S. Application Data continuation of application No. 14/622,831, filed on Feb. 14, 2015, now Pat. No. 10,595,711, which is a continuation-in-part of application No. 13/913,466, filed on Jun. 9, 2013, now Pat. No. 9,186,131, which is a continuation-in-part of application No. 13/531,477, filed on Jun. 22, 2012, now Pat. No. 8,932,211, which is a continuation-in-part of application No. 12/970,604, filed on Dec. 16, 2010, now Pat. No. 8,506,479.

(60) Provisional application No. 61/287,077, filed on Dec. 16, 2009.

(51) Int. Cl.

| | | |
|---|---|---|
| *A61B 1/31* | (2006.01) | |
| *A61B 1/32* | (2006.01) | |
| *A61B 17/00* | (2006.01) | |
| *A61B 17/02* | (2006.01) | |
| *A61B 17/128* | (2006.01) | |
| *A61B 17/34* | (2006.01) | |

(52) U.S. Cl.
CPC ...... *A61B 1/00085* (2013.01); *A61B 1/00087* (2013.01); *A61B 1/00135* (2013.01); *A61B 1/018* (2013.01); *A61B 1/31* (2013.01); *A61B 1/32* (2013.01); *A61B 17/00234* (2013.01); *A61B 17/0218* (2013.01); *A61B 17/1285* (2013.01); *A61B 2017/00269* (2013.01); *A61B 2017/003* (2013.01); *A61B 2017/00557* (2013.01); *A61B 2017/00818* (2013.01); *A61B 2017/0225* (2013.01); *A61B 17/3421* (2013.01); *A61B 2017/345* (2013.01)

(56) References Cited

U.S. PATENT DOCUMENTS

| | | |
|---|---|---|
| 1,621,159 A | 3/1927 | Evans |
| 2,072,346 A | 3/1937 | Smith |
| 2,434,167 A | 1/1948 | Knoblauch |
| 3,495,586 A | 2/1970 | Regenbogen |
| 3,517,128 A | 6/1970 | Hines |
| 3,557,794 A | 1/1971 | Van Patten |
| 4,040,413 A | 8/1977 | Ohshiro |
| 4,083,369 A | 4/1978 | Sinnreich |
| 4,224,929 A | 9/1980 | Furihata |
| 4,295,464 A | 10/1981 | Shihata |
| 4,519,403 A | 5/1985 | Dickhudt |
| 4,611,594 A | 9/1986 | Grayhack et al. |
| 4,710,171 A | 12/1987 | Rosenberg |
| 4,718,406 A | 1/1988 | Bregman et al. |
| 4,836,204 A | 6/1989 | Landymore et al. |
| 4,966,596 A | 10/1990 | Kuntz et al. |
| 5,025,778 A | 6/1991 | Silverstein et al. |
| 5,059,199 A | 10/1991 | Okada et al. |
| 5,087,265 A | 2/1992 | Summers |
| 5,112,310 A | 5/1992 | Grobe |
| 5,167,239 A | 12/1992 | Cohen et al. |
| 5,197,971 A | 3/1993 | Bonutti |
| 5,211,624 A | 5/1993 | Cinberg et al. |
| 5,211,638 A | 5/1993 | Dudar et al. |
| 5,259,366 A | 11/1993 | Reydel et al. |
| 5,336,227 A | 8/1994 | Nakao et al. |
| 5,386,817 A | 2/1995 | Jones |
| 5,411,475 A | 5/1995 | Atala et al. |
| 5,411,508 A | 5/1995 | Bessler et al. |
| 5,423,830 A | 6/1995 | Schneebaum et al. |
| 5,454,365 A | 10/1995 | Bonutti |
| 5,655,698 A | 8/1997 | Yoon |
| 5,709,657 A | 1/1998 | Zimmon |
| 5,716,321 A | 2/1998 | Kerin et al. |
| 5,722,103 A | 3/1998 | Walega |
| 5,776,097 A | 7/1998 | Massoud |
| 5,840,031 A | 11/1998 | Crowley |
| 5,947,983 A | 9/1999 | Solar et al. |
| 5,954,731 A | 9/1999 | Yoon |
| 5,997,547 A | 12/1999 | Nakao et al. |
| 6,009,877 A | 1/2000 | Edwards |
| 6,042,596 A | 3/2000 | Bonutti |
| 6,119,913 A | 9/2000 | Adams et al. |
| 6,142,931 A | 11/2000 | Kaji |
| 6,142,933 A | 11/2000 | Longo et al. |
| 6,203,552 B1 | 3/2001 | Bagley et al. |
| 6,214,024 B1 | 4/2001 | Houser |
| 6,264,086 B1 | 7/2001 | McGuckin |
| 6,302,311 B1 | 10/2001 | Adams et al. |
| 6,343,731 B1 | 2/2002 | Adams et al. |
| 6,405,732 B1 | 6/2002 | Edwards et al. |
| 6,423,058 B1 | 7/2002 | Edwards et al. |
| 6,428,473 B1 | 8/2002 | Leonard et al. |
| 6,443,959 B1 | 9/2002 | Bland et al. |
| 6,494,881 B1 | 12/2002 | Bales et al. |
| 6,605,078 B2 | 8/2003 | Adams |
| 6,616,603 B1 | 9/2003 | Fontana |
| 6,656,191 B2 | 12/2003 | Ouchi |
| 6,695,198 B2 | 2/2004 | Adams et al. |
| 6,805,273 B2 | 10/2004 | Bilotti et al. |
| 6,808,491 B2 | 10/2004 | Kortenbach et al. |
| 6,840,423 B2 | 1/2005 | Adams et al. |
| 6,866,178 B2 | 3/2005 | Adams et al. |
| 6,874,669 B2 | 4/2005 | Adams et al. |
| 6,913,610 B2 | 7/2005 | Nakao |
| 6,923,806 B2 | 8/2005 | Hooven et al. |
| 6,938,814 B2 | 9/2005 | Sharma et al. |
| 7,014,646 B2 | 3/2006 | Adams |
| 7,059,331 B2 | 6/2006 | Adams et al. |
| 7,063,659 B2 | 6/2006 | Goto et al. |
| 7,169,115 B2 | 1/2007 | Nobis et al. |
| 7,276,066 B2 | 10/2007 | Ouchi |
| 7,396,329 B2 | 7/2008 | Nakao |
| 7,445,598 B2 | 11/2008 | Orban, III |
| 7,918,787 B2 | 4/2011 | Saadat |
| 7,959,559 B2 | 6/2011 | Yamaya |
| 8,007,508 B2 | 8/2011 | Cox |
| 8,277,373 B2 | 10/2012 | Maahs et al. |
| 8,506,479 B2 | 8/2013 | Piskun et al. |
| 8,517,933 B2 | 8/2013 | Mohr |
| 8,608,652 B2 | 12/2013 | Voegele et al. |
| 8,764,630 B2 | 7/2014 | Yamatani |
| 8,777,961 B2 | 7/2014 | Cabrera et al. |
| 8,932,326 B2 | 1/2015 | Riina et al. |
| 8,979,884 B2 | 3/2015 | Milsom et al. |
| 9,039,601 B2 | 5/2015 | Piskun |
| 9,050,004 B2 | 6/2015 | Diao et al. |
| 9,161,746 B2 | 10/2015 | Piskun et al. |
| 9,168,053 B2 | 10/2015 | Cox |
| 9,259,233 B2 | 2/2016 | Gruber et al. |
| 9,370,379 B2 | 6/2016 | Osman |
| 9,375,224 B2 | 6/2016 | Jansen |
| 9,661,984 B2 | 5/2017 | Piskun |
| 2001/0047169 A1 | 11/2001 | McGuckin, Jr. et al. |
| 2001/0049497 A1 | 12/2001 | Kalloo et al. |
| 2001/0056260 A1 | 12/2001 | Grimes et al. |
| 2002/0123748 A1 | 9/2002 | Edwards et al. |
| 2002/0183593 A1 | 12/2002 | Chin et al. |
| 2002/0193660 A1 | 12/2002 | Weber et al. |
| 2003/0023143 A1 | 1/2003 | Abe et al. |
| 2003/0050663 A1 | 3/2003 | Khachin et al. |
| 2003/0074015 A1 | 4/2003 | Nakao |
| 2003/0135230 A1 | 7/2003 | Massey et al. |
| 2003/0187494 A1 | 10/2003 | Loaldi |
| 2003/0225432 A1 | 12/2003 | Baptiste et al. |
| 2003/0225433 A1 | 12/2003 | Nakao |
| 2004/0034278 A1 | 2/2004 | Adams |
| 2004/0158263 A1 | 8/2004 | McAlister et al. |
| 2004/0204725 A1 | 10/2004 | Bayer |
| 2004/0210116 A1 | 10/2004 | Nakao |
| 2004/0249367 A1 | 12/2004 | Saadat et al. |
| 2005/0027288 A1 | 2/2005 | Oyagi et al. |
| 2005/0177105 A1 | 8/2005 | Shalev |
| 2005/0234297 A1 | 10/2005 | Devierre et al. |

(56) References Cited

U.S. PATENT DOCUMENTS

| | | |
|---|---|---|
| 2005/0234299 A1 | 10/2005 | Eitenmuller et al. |
| 2005/0240147 A1 | 10/2005 | Makower et al. |
| 2005/0251111 A1 | 11/2005 | Saito et al. |
| 2005/0251177 A1* | 11/2005 | Saadat ............... A61F 5/0086 606/153 |
| 2005/0272977 A1 | 12/2005 | Saadat et al. |
| 2005/0273085 A1 | 12/2005 | Hinman et al. |
| 2006/0074277 A1 | 4/2006 | Yoshida |
| 2006/0100480 A1 | 5/2006 | Ewers et al. |
| 2006/0189845 A1 | 8/2006 | Maahs et al. |
| 2006/0191975 A1 | 8/2006 | Adams et al. |
| 2006/0247662 A1 | 11/2006 | Schwartz et al. |
| 2006/0264706 A1 | 11/2006 | Piskun |
| 2007/0005093 A1 | 1/2007 | Cox |
| 2007/0021778 A1 | 1/2007 | Carly |
| 2007/0093809 A1 | 4/2007 | Edwards et al. |
| 2007/0255207 A1 | 11/2007 | Hangai et al. |
| 2007/0287886 A1 | 12/2007 | Saadat |
| 2007/0287889 A1 | 12/2007 | Mohr |
| 2007/0293724 A1 | 12/2007 | Saadat et al. |
| 2008/0045842 A1 | 2/2008 | Furnish |
| 2008/0051629 A1 | 2/2008 | Sugiyma et al. |
| 2008/0058590 A1 | 3/2008 | Saadat et al. |
| 2008/0132835 A1 | 6/2008 | Nagamatsu et al. |
| 2008/0161645 A1 | 7/2008 | Goldwasser et al. |
| 2008/0188868 A1 | 8/2008 | Weitzner et al. |
| 2008/0228209 A1 | 9/2008 | DeMello et al. |
| 2008/0249534 A1 | 10/2008 | Gruber et al. |
| 2008/0262492 A1 | 10/2008 | Lee |
| 2008/0269557 A1 | 10/2008 | Marescaux et al. |
| 2008/0269559 A1 | 10/2008 | Miyamoto et al. |
| 2008/0275300 A1 | 11/2008 | Rothe et al. |
| 2008/0300454 A1 | 12/2008 | Goto |
| 2009/0018500 A1 | 1/2009 | Carter et al. |
| 2009/0030369 A1 | 1/2009 | Nagamatsu et al. |
| 2009/0149716 A1 | 6/2009 | Diao et al. |
| 2009/0156996 A1 | 6/2009 | Milsom et al. |
| 2009/0287046 A1 | 11/2009 | Yamatani |
| 2009/0312645 A1 | 12/2009 | Weitzner et al. |
| 2010/0010296 A1 | 1/2010 | Piskun |
| 2010/0049137 A1 | 2/2010 | Fischer, Jr. |
| 2010/0094327 A1 | 4/2010 | Milsom et al. |
| 2010/0106240 A1 | 4/2010 | Duggal et al. |
| 2010/0152590 A1 | 6/2010 | Moore et al. |
| 2011/0065985 A1 | 3/2011 | Wehrheim |
| 2011/0077498 A1 | 3/2011 | McDaniel |
| 2011/0105850 A1* | 5/2011 | Voegele ............. A61B 17/3423 606/119 |
| 2011/0160538 A1 | 6/2011 | Ravikumar et al. |
| 2011/0172491 A1 | 7/2011 | Piskun et al. |
| 2011/0224494 A1 | 9/2011 | Piskun et al. |
| 2011/0245858 A1 | 10/2011 | Milsom et al. |
| 2011/0306832 A1 | 12/2011 | Bassan et al. |
| 2012/0053485 A1 | 3/2012 | Bloom |
| 2012/0083797 A1 | 4/2012 | Cabrera et al. |
| 2012/0095498 A1 | 4/2012 | Stefanchik et al. |
| 2012/0109178 A1 | 5/2012 | Edwards et al. |
| 2012/0165604 A1 | 6/2012 | Stokes et al. |
| 2013/0090527 A1 | 4/2013 | Axon |
| 2013/0172828 A1 | 7/2013 | Kappel et al. |
| 2013/0192116 A1 | 8/2013 | Elftmann, Jr. |
| 2013/0274553 A1 | 10/2013 | Piskun et al. |
| 2013/0274556 A1 | 10/2013 | Nearman et al. |
| 2013/0317303 A1 | 11/2013 | Deshmukh et al. |
| 2013/0324795 A1 | 12/2013 | Nakajima et al. |
| 2014/0142393 A1 | 5/2014 | Piskun et al. |
| 2014/0316379 A1 | 10/2014 | Sonderegger et al. |
| 2015/0150436 A1 | 6/2015 | Cornhill et al. |
| 2015/0157192 A1 | 6/2015 | Piskun et al. |
| 2015/0265268 A1 | 9/2015 | Diao et al. |
| 2015/0265818 A1 | 9/2015 | Piskun et al. |
| 2015/0272564 A1 | 10/2015 | Piskun et al. |
| 2015/0327754 A1 | 11/2015 | Leeflang et al. |
| 2015/0351890 A1 | 12/2015 | Levin et al. |
| 2016/0038172 A1 | 2/2016 | Cox |
| 2016/0081702 A1 | 3/2016 | Kan et al. |
| 2016/0106466 A1 | 4/2016 | Gruber et al. |
| 2016/0157843 A1 | 6/2016 | Dickson et al. |
| 2016/0374658 A1 | 12/2016 | Piskun |

FOREIGN PATENT DOCUMENTS

| | | |
|---|---|---|
| CN | 101048101 A | 10/2007 |
| CN | 100452044 C | 1/2009 |
| CN | 100462044 C | 2/2009 |
| CN | 201200436 Y | 3/2009 |
| CN | 102018493 A | 4/2011 |
| CN | 102695541 A | 9/2012 |
| CN | 103340679 A | 10/2013 |
| CN | 104135972 A | 11/2014 |
| EP | 0163502 A2 | 12/1985 |
| EP | 1588670 A1 | 10/2005 |
| EP | 2512577 A2 | 10/2012 |
| GB | 2365340 A | 2/2002 |
| JP | S63292935 A | 11/1988 |
| JP | H06296617 A | 10/1994 |
| JP | H08317928 A | 12/1996 |
| JP | H08336538 A | 12/1996 |
| JP | 2533732 Y2 | 4/1997 |
| JP | H09503677 A | 4/1997 |
| JP | H1028691 A | 2/1998 |
| JP | 2000166936 A | 6/2000 |
| JP | 2000325303 A | 11/2000 |
| JP | 2001527429 A | 12/2001 |
| JP | 2003033436 A | 2/2003 |
| JP | 2003522590 A | 7/2003 |
| JP | 2004154485 A | 6/2004 |
| JP | 2004529708 A | 9/2004 |
| JP | 2005046274 A | 2/2005 |
| JP | 2006244071 A | 9/2006 |
| JP | 2007511247 A | 5/2007 |
| JP | 2008528239 A | 7/2008 |
| JP | 2008536552 A | 9/2008 |
| JP | 2009523054 A | 6/2009 |
| JP | 2009279406 A | 12/2009 |
| JP | 2010511440 A | 4/2010 |
| JP | 2011072782 A | 4/2011 |
| JP | 2012075908 A | 4/2012 |
| JP | 2013514827 A | 5/2013 |
| JP | 2015000280 A | 1/2015 |
| JP | 2015525109 A | 9/2015 |
| JP | 2016526397 A | 9/2016 |
| WO | 9101773 A1 | 2/1991 |
| WO | 9635469 A1 | 11/1996 |
| WO | 9640347 A1 | 11/1996 |
| WO | 03000139 A1 | 1/2003 |
| WO | 2004103430 A2 | 12/2004 |
| WO | 2005048828 A1 | 6/2005 |
| WO | 2006110275 A2 | 10/2006 |
| WO | 2007081601 A2 | 7/2007 |
| WO | 2008011163 A2 | 1/2008 |
| WO | 2008070556 A1 | 6/2008 |
| WO | 2009059296 A1 | 5/2009 |
| WO | 2009076176 A1 | 6/2009 |
| WO | 2009117696 A1 | 9/2009 |
| WO | 2011084616 A2 | 7/2011 |
| WO | 2012068048 A1 | 5/2012 |
| WO | 2012114569 A1 | 8/2012 |
| WO | 2013050880 A2 | 4/2013 |
| WO | 2013192116 A1 | 12/2013 |
| WO | 2014164661 A1 | 10/2014 |
| WO | 2014200737 A1 | 12/2014 |
| WO | 2015026968 A1 | 2/2015 |
| WO | 2015191125 A1 | 12/2015 |

OTHER PUBLICATIONS

European Search Report dated Jun. 1, 2014 for International Application No. PCT/US2014/040429.

European Search Report dated May 3, 2011 for European Patent Application No. 06789411.3.

Written Opinion dated Jun. 20, 2007 for International Application No. PCT/US06/30464.

(56) References Cited

OTHER PUBLICATIONS

Chinese Office Action dated May 12, 2009 for Chinese Application No. 200680028706.2.
International Search Report and Written Opinion for PCT Application No. PCT/US17/50685, dated Dec. 14, 2017, 16 pages.
European Communication for European Patent Application No. 14733912.1, dated Jun. 11, 2018, 2 pages.
International Search Report and Written Opinion dated May 9, 2018, for PCT/US17/68991, 11 pages.
International Search Report and Written Opinion for International Application No. PCT/US18/14388, dated Jun. 19, 2018, 9 pages.
International Search Report and Written Opinion for PCT/US10/60802, dated Aug. 24, 2011, 12 pages.
International Search Report and Written Opinion for International Application No. PCT/US18/21779, dated Jun. 14, 2018, 10 pages.
"Oleg Shikhman vs. Bobcat Endoscopy, LLC (F/K/A LumenR LLC) and Gregory Piskun, M.D. Complaint," filed Oct. 17, 2017 at Judicial District of Fairfield at Bridgeport, 25 pages.
"Oleg Shikhman vs. Bobcat Endoscopy, LLC (F/K/A/ LumenR LLC) and Gregory Piskun, M.D. Reply to Affirmative Defenses, Matters in Avoidance and Answer to Counterclaims", Docket No. X03-HHD-CV17-6087023-S, dated Dec. 12, 2018, 19 pages.
"Oleg Shikhman vs. Bobcat Endoscopy, LLC (F/K/A/ LumenR LLC) and Gregory Piskun, M.D., Answer, Special Defenses and Counterclaims," Docket No. HHD-CV-608 7023-S, dated Sep. 13, 2018, 23 pages.
"Oleg Shikhman vs. Bobcat Endoscopy, LLC (F/K/A/ LumenR LLC) and Gregory Piskun, M.D., First Amended Answer, Affirmative Defenses and Counterclaims", Docket No. X03-CV17-6087023-S, dated Nov. 9, 2018, 24 pages.
"Letter from Jeffrey M. Chamberlain, Senior Principal at Kacvinsky Daisak Bluni pllc to Michael J. Rye, Esq. c/o Cantor Colburn, LLP", dated Nov. 13, 2018, 3 pages.
Letter from Michael J. Rye, Partner at Cantor Colburn LLP to Michael Mahoney, CEO at Boston Scientific Corporation, dated Oct. 17, 2017, 3 pages.
Letter from Michael J. Rye, Partner at Cantor Colburn LLP to Jeffrey M, Chamberlain at Kacvinsky Daisak Bluni PLLC, dated Aug. 28, 2018, 2 pages.

*Oleg Shikhman* v. *Bobcat Endoscopy LLC, et al*; Memorandum of Decision, filed Oct. 31, 2019, 22 pages (p. 1, line 15-p. 2, line 3; p. 2, lines 7-8, p. 7, lines 4-6; p. 8 lines 3-13; p. 10, line 4-p. 11, line 9, p. 18, line 5-p. 19, line 2; p. 18. footnote 15.).
International Search Report and Written Opinion for International Application No. PCT/US2016/031355, dated Sep. 23, 2016, 17 pages.
International Search Report and Written Opinion for International Application No. PCTUS2013/046200, dated Sep. 23, 2013, 11 pages.
International Search Report and Written Opinion dated Jun. 20, 2007 for International Application No. PCTUS0630464, 6 pages.
Letter from Philip G. Hampton, II at Haynes and Boone, LLP to Kurt W. Lockwood, Esq. at Kacvinsky Daisak Bluni PLLC, dated Nov. 16, 2018, 2 pages.
Letter from Kurt W. Lockwood, Principal at Kacvinsky Daisak Bluni pllc, to Philip G. Hampton, II c/o Haynes and Boone, LLP dated Nov. 9, 2018, 16 pages.
*Sergey Kantsevoy* v. *LumenR LLC* Complaint, Civil Action No. 17-359, filed Feb. 7, 2017, 18 pages.
*Sergey Kantsevoy* vs. *LumenR LLC*, Answer, Affirmative Defenses and Counterclaims, Civil Action No. 17-cv-359 (ELH), filed Feb. 28, 2017, 25 pages.
*Sergey Kantsevoy* v. *LumenR LLC*, Dr. Sergey Kantsevoy's Answer to LumenR LLC's Counterclaims, Civil Action No. 17-359 (ELH), filed Mar. 17, 2017, 8 pages.
The Extended PCT Search Report Application No. PCT/US2016/031355 dated Jul. 18, 2016. aaaa.
European Search Report for the European Patent Application No. EP19214960, dated Apr. 17, 2020, 6 pages.
Extended European Search Report and Written Opinion for the European Patent Application No. EP192114866, dated Apr. 20, 2020, 10 pages.
International Search Report and Written Opinion for the International Patent Application No. PCTUS2020063710, dated Mar. 30, 2021, 15 pages.
International Preliminary Report on Patentability dated Jun. 28, 2012 for International Application No. PCT/US2010/060802.
International Search Report and Written Opinion for Application No. PCT/US2014/04029, dated Aug. 1, 2014, 11 pages.

* cited by examiner

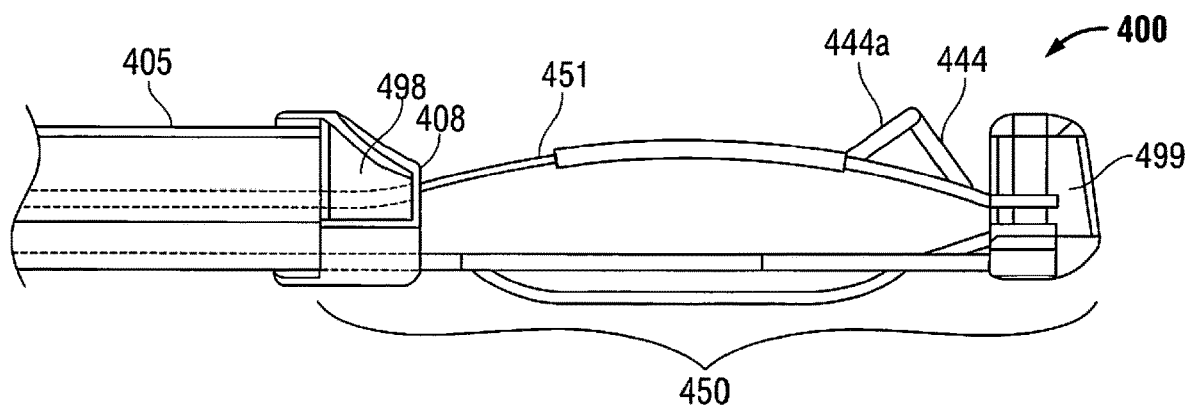
FIG. 4A
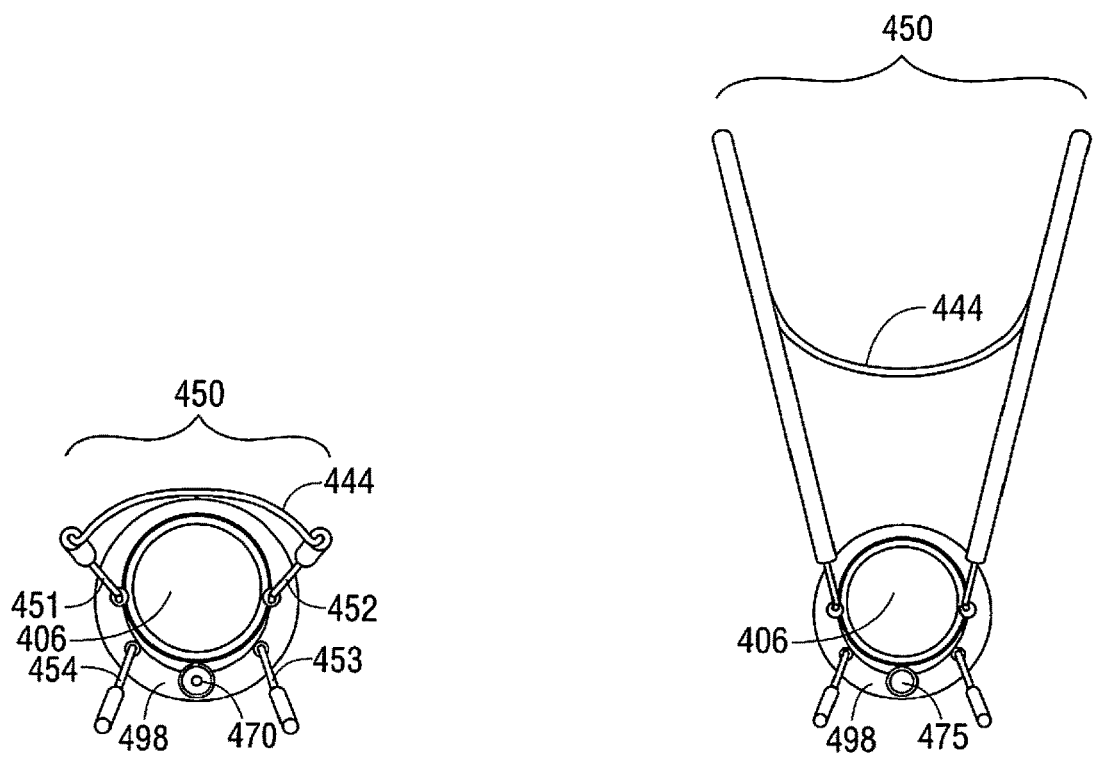
FIG. 4B  FIG. 4C

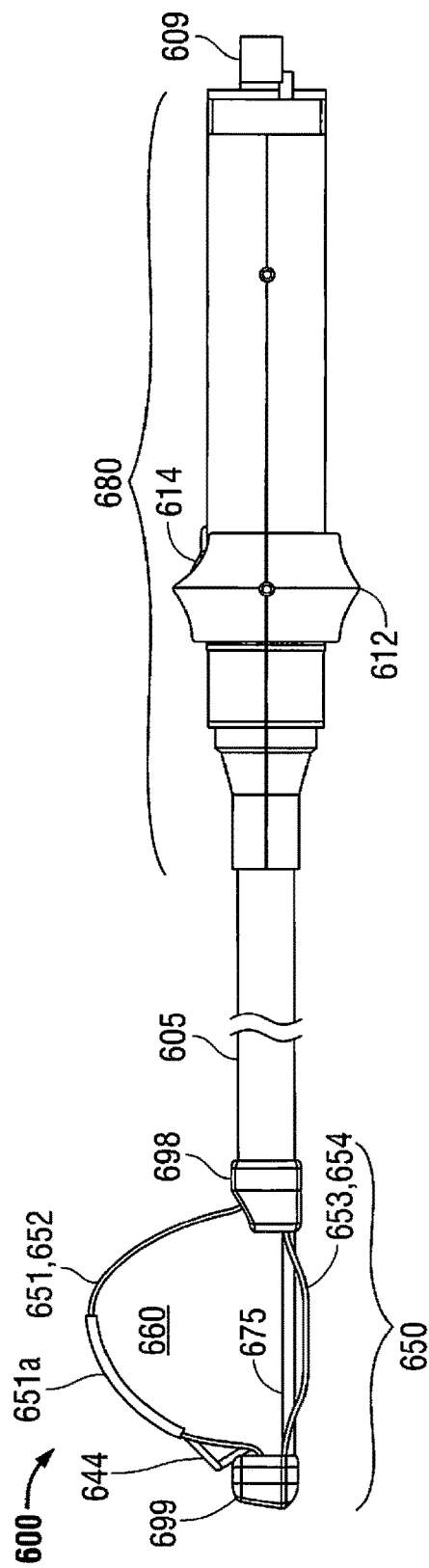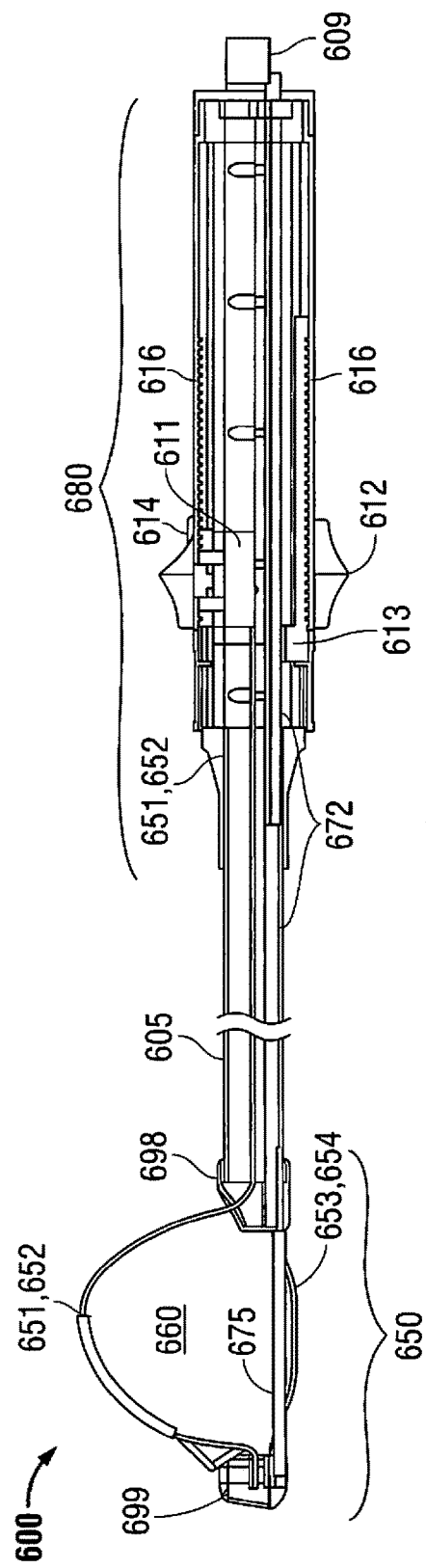

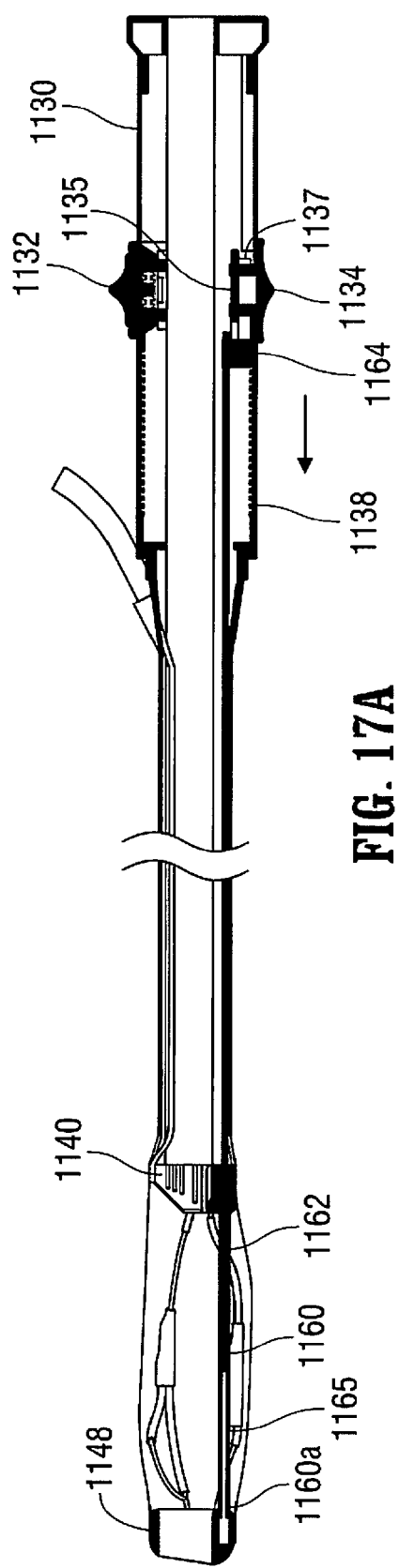
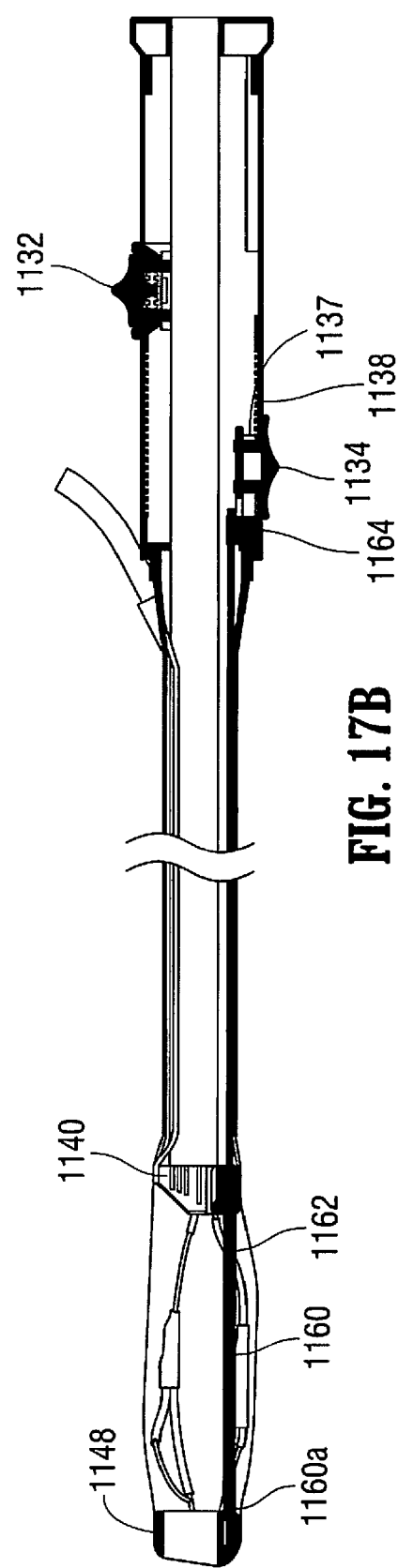
FIG. 17A
FIG. 17B

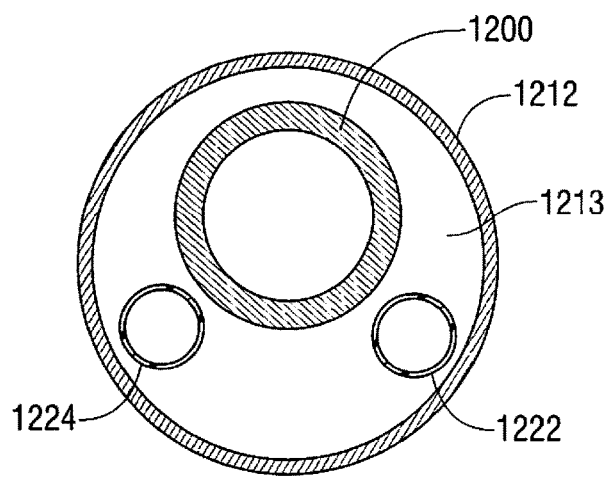
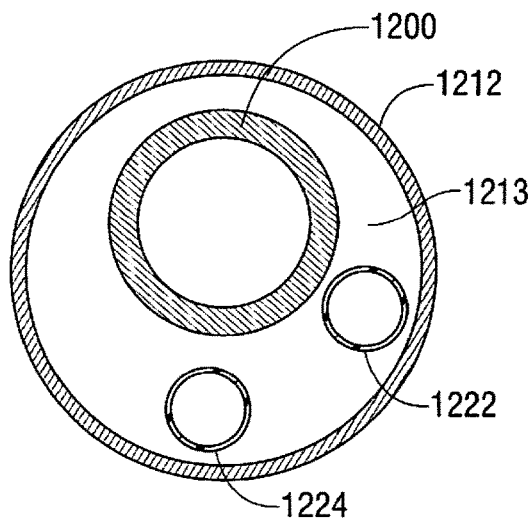
FIG. 37A   FIG. 37B
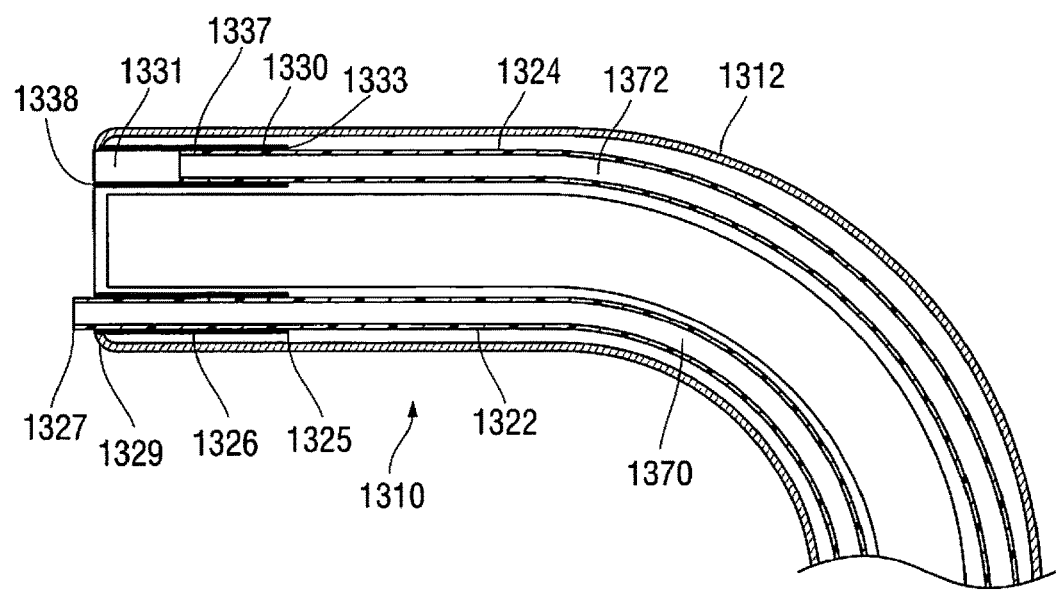
FIG. 38

TISSUE RETRACTOR FOR MINIMALLY INVASIVE SURGERY

CROSS-REFERENCE TO RELATED APPLICATION

This application is a continuation of U.S. application Ser. No. 16/688,453 filed Nov. 19, 2019, which is a continuation of U.S. application Ser. No. 14/622,831 filed Feb. 14, 2015, now U.S. Pat. No. 10,595,711, which is a continuation in part of application Ser. No. 13/913,466, filed Jun. 9, 2013, now U.S. Pat. No. 9,186,131, which is a continuation in part of Ser. No. 13/531,477, filed Jun. 22, 2012, now U.S. Pat. No. 8,932,211, which is a continuation in part of application Ser. No. 12/970,604, filed Dec. 16, 2010, now U.S. Pat. No. 8,506,479, which claims priority under 35 U.S.C. § 119 to U.S. Provisional Application Ser. No. 61/287,077, filed Dec. 16, 2009. The entire contents of each of these applications are incorporated herein by reference.

FIELD OF INVENTION

The teachings provided herein are generally directed to improved methods and devices for operatively treating gastrointestinal disorders endoscopically in a stable, yet dynamic operative environment, and in a minimally-invasive manner.

DESCRIPTION OF THE RELATED ART

Endoscopic procedures involving the gastrointestinal system offer advantages over conventional surgery in that they are less invasive and may provide visualization. These procedures continue to evolve to address problems and provide new methods of treatment identified by those skilled in the art.

One current problem includes a lack of technology for an optimal minimally-invasive expansion of a stable, working space adjacent to the target tissues that could otherwise collapse around the target lesion or defect during an operative treatment. Having the ability to effectively expand and optimally reconfigure (reshape) the working space could markedly facilitate an intra-luminal operation. A better expanded, stable and optimally configured working space allows the instruments and endoscope to be independently manipulated and properly visualized around the target tissue. One of skill would appreciate having the ability to see and approach both the target tissue and the surrounding anatomy for reference, orientation, and surgical maneuvering.

Another current problem includes a lack of an endoscopic technology for not only expanding, but also affixing and reshaping, both the target tissue and surrounding tissue. In a bowel, for example, such a stable operative space could include a space that is non or less collapsible, with limited peristalsis or aperistaltic, and/or affixed at a particular point in the abdominal cavity. The fixed point can be considered fixed in relation to, for example, a fixed body point in the patient, such as the patient's hip. Significant bowel movement is considered to be highly undesirable during an intra-luminal operation on the bowel, for example, since it may create a challenging, unstable operative environment. Such bowel movement is normal, of course, even in a sedated patient and can be caused, for example, by bowel collapse from an air leak, peristalsis, breathing, and movement of the scope and instruments. Having a technology to overcome this problem would help provide a stable operative space, which is clinically desired by one of skill in the operative environment.

Another current problem includes a lack of an endoscopic technology for retracting the tissue dynamically, for example, through an adjustable tissue retraction structure allowing for a controlled degree of expansion or collapse of the structure, to further configure the working space as desired around the instruments and target tissue. Such control can effectively provide for a method of adjusting the retractor, as well as tissue placement, in- and -around the working space. By increasing and releasing the tension on the retractor, the amount of tissue to be placed in the working space, for example, can be better-gauged and controlled during a procedure. Moreover, the tissue retraction and, particularly, traction- contra-traction can be facilitated to help create a desired dissecting plane or position the tissue more optimally during an operation. Having a technology to overcome this problem would help create an operative environment that is more desirable for tissue dissection, retraction, cutting and a removal of tissue.

Another current problem includes a lack of an endoscopic technology for organizing the endoscope, instruments, and working space in a manner that can maximize the working space for the treatment. The larger working space can improve the ability to manipulate the instruments and endoscope in a minimally-invasive manner from outside the body. Namely, one of skill would like to have a working space that has a point of entry for the instruments that is as far as practical from the target tissue to provide additional flexibility in approaching and visualizing the target tissue, perhaps providing more operating room for selecting a trajectory of the instruments toward the target tissue that is, for example, at least substantially perpendicular to the plane of dissection of the target tissue. Having a technology to overcome this problem would provide the person of skill with a system and procedure that is more desirable for a removal of tissue.

In view of at least the above, one of skill in the art of endoscopic, gastrointestinal surgical treatments would appreciate the technology taught herein which provides one or more of (i) a minimally-invasive expansion of the intraluminal working space; (ii) an affixing, particularly an affixing that includes a reconfiguring without stretching or reconfiguring with stretching, of both the target tissue and surrounding tissue to help provide a stable, operative space; (iii) a retracting of the tissue dynamically, allowing for a partial or complete expansion or collapse, to further configure the working space between the instruments and the target tissue; and (iv) an organization of the endoscope instruments, such as the retractor and tools to maximize the working space and maneuverability, allowing for a maximum flexibility in approaching and visualizing the target tissue. It should be appreciated that having such improvements would reduce the technical complexity, and increase the efficacy and safety of, otherwise complex endoscopic operations. Moreover, doing so at a low cost, while using an affordable system that is introduced in the subject atraumatically and in a manner that does not substantially disrupt the conventional colonoscopy workflow, would be seen by those of skill as a very substantial advancement in the field of endoscopic surgical procedures.

SUMMARY

The teachings provided herein are generally directed to improved methods and devices for operatively treating gastrointestinal disorders endoscopically in a stable, yet dynamic operative environment, and in a minimally-invasive manner. The systems, for example, include an endoscopic surgical suite. The surgical suite can have a reversibly-expandable retractor that expands to provide a stable, operative environment within a subject. The expansion can be asymmetric around a stabilizer subsystem to maximize space for a tool and in some embodiments an endoscope to each be maneuvered independently to visualize a target tissue and treat the target tissue from outside the patient in a minimally invasive manner. Embodiments taught herein provide, among other improvements, an increase in distance between tool ports and the target tissue to improve maneuverability and triangulation of the tools with respect to the target tissue, as well as a larger field of view.

In some embodiments, floating channels are provided to increase the flexibility of the system as compared to the use of fixed channels. The floating channels receive flexible instrument guides which provide channels for working instruments. Alternatively, working instruments can be inserted directly into the floating channels.

In one aspect of the present disclosure, a system for performing minimally invasive procedures in a working space within a body lumen of a patient, such as in a gastrointestinal tract, is provided comprising a flexible catheter having an inner wall, an outer wall, a first lumen, a first flexible tube positioned in the first lumen, and a second flexible tube positioned in the first lumen. The first lumen defines a first space configured and dimensioned to receive an endoscope. The first and second flexible tubes are fixed at a proximal portion and configured to float within the first lumen of the flexible catheter. A first flexible guide is slidably positioned within the first flexible tube and is configured and dimensioned to receive a first instrument for axial movement therein. The first flexible guide has a longitudinal axis and a distal portion movable to an angled position with respect to the longitudinal axis of the first flexible guide. A second flexible guide is slidably positioned within the second flexible tube and is configured and dimensioned to receive a second instrument for axial movement therein. The second flexible guide has a longitudinal axis and a distal portion movable to an angled position with respect to the longitudinal axis of the second flexible guide. A body working space expanding system is positioned at a distal portion of the flexible catheter and is movable from a non-expanded insertion position to an expanded position forming an expanded region to expand the working space within the body lumen. The distal portion of the first flexible guide and the distal portion of the second flexible guide are movable to angled positions within the expanded region.

In some embodiments, the system includes a covering for the expanding system having an opening to receive body tissue. The opening in the covering in some embodiments is closable for example by a string or suture.

In some embodiments, the first flexible tube and/or the second flexible tube is unattached to the flexible catheter at a distal end. In other embodiments, the first flexible tube and/or the second flexible tube is attached to the flexible catheter at a distal end.

The system can further include a first tubular support positioned within the flexible catheter, wherein the first flexible tube is unattached to the flexible catheter at a distal end so the first flexible tube telescopes within the first tubular support as the flexible catheter is bent a sufficient amount. The system can further include a second tubular support positioned within the flexible catheter, wherein the second flexible tube is unattached to the catheter at a distal end so the second flexible tube telescopes with respect to the second tubular support as the catheter is bent a sufficient amount.

In some embodiments, first flexible tube and/or the second flexible tube is dimensioned to telescope to extend into the expanded region formed by the expanding system.

In some embodiments, the expanding system comprises a plurality of flexible elements, wherein upon expansion of the expanding system to the expanded position first and second flexible elements of the plurality of flexible elements move from their collapsed insertion position outwardly away from a longitudinal axis of the catheter to the expanded position. Third and fourth flexible elements of the plurality of flexible elements can in some embodiments remain substantially in the non-expanded insertion position.

The system can further include a stabilizer movable from a first position to a second position to increase the stability and rigidity of the expanding system. In other embodiments, at least one of the flexible elements has sufficient rigidity to stabilize the expanding system.

The system can include an actuator positioned at a proximal region of the catheter and operably coupled to the working space expanding system to move the first and second elements between the non-expanded and expanded positions.

In some embodiments, the system includes a proximal coupler to retain a proximal portion of the first and second flexible elements and a distal coupler to retain a distal portion of the first and second elements, wherein the proximal and distal couplers include a lumen dimensioned to receive the endoscope therethrough when the catheter is backloaded over the endoscope.

In accordance with another aspect of the present disclosure, a system for performing minimally invasive procedures in a working space within a body lumen of a patient is provided comprising a flexible main tube having a first lumen, a first flexible tube positioned within the first lumen and floating within the first lumen of the tube such that at least an intermediate portion of the first flexible tube moves radially within the first lumen. The first lumen is further configured and dimensioned to receive an endoscope, the first lumen enabling floating movement of the endoscope within the first lumen. A first flexible guide is slidably positioned within the first flexible tube, the first flexible guide configured and dimensioned to receive a first instrument for axial movement therein, and the first flexible guide has a longitudinal axis and a distal portion movable to an angled position with respect to the longitudinal axis. A working space expanding system is positioned at a distal portion of the catheter, the expanding system movable from a non-expanded insertion position to an expanded position forming an expanded cage to expand the working space within the body lumen. The distal portion of the first flexible guide is movable within the expanded cage.

In some embodiments, the system further includes a second flexible tube positioned within the first lumen, the second flexible tube floating within the single lumen of the tube such that at least an intermediate portion of the second flexible tube moves radially within the first lumen and a second flexible guide is slidably positioned within the second flexible tube. The second flexible guide is configured and dimensioned to receive a second instrument for axial movement therein, the second flexible guide having a longitudinal axis and a tube distal portion movable to an angled position with respect to the longitudinal axis.

In some embodiments, one or both of the first and second flexible tubes are unattached at a distal portion so they telescope within the flexible catheter. The expanding system can further include a stabilizing structure to rigidify the cage.

In accordance with another aspect of the present disclosure, a system for performing minimally invasive procedures in a working space within a body lumen of a patient is provided, the system comprising a flexible catheter having a proximal portion and a distal portion and a working space expanding system positioned at the distal portion. The expanding system is movable from a non-expanded insertion position to an expanded position forming an expanded region to expand the working space within the body lumen to form an asymmetric working space, the expanding system including first and second flexible retractor elements movable laterally outwardly to expand the working space within the body lumen. The expanding system further includes a third element, the third element extending longitudinally and configured to increase the rigidity of the structure.

In accordance with another aspect of the present disclosure, a system for performing minimally invasive procedures in a working space within a body lumen of a patient is provided, the system comprising a flexible catheter having an inner wall, an outer wall, a first flexible tube, and a second flexible tube. The catheter is insertable over an endoscope such that the endoscope is received within the flexible catheter. The first and second flexible tubes are attached to the catheter at a proximal portion thereof to provide first and second floating lumens to reduce the stiffness of the flexible catheter, the first flexible tube configured and dimensioned to receive one or both of a) a first flexible guide for axial movement therein or b) a first endoscopic tool for axial movement therein. The second flexible tube is configured and dimensioned to receive one or both of a) a second flexible guide for axial movement therein orb) a second endoscopic tool for axial movement therein.

A working space expanding system is positioned at a distal portion of the flexible catheter. The expanding system is movable from a non-expanded insertion position to an expanded position forming an expanded cage to expand the working space within the body lumen, and, in some embodiments, an asymmetric shape to form an asymmetric working space. The distal portion of the first and second flexible guides is movable within the expanded cage.

In some embodiments, the distal tips of the flexible guides can be substantially aligned with the longitudinal axis when positioned within the catheter and return to the angled position when exposed from the first and second flexible tubes.

The system can include a first and/or second actuator. The first actuator can be positioned at a proximal region of the catheter and operably coupled to a stabilizing element to move the stabilizing element between a first position and a second position to increase the stability and rigidity of the cage. The second actuator can be positioned at a proximal region of the catheter and operably coupled to the first and second flexible elements of the reshaping system to move the first and second elements between the non-expanded and expanded positions.

The system in some embodiments includes a proximal coupler to retain a proximal portion of the first and second elements of the reshaping system and a distal coupler to retain a distal portion of the first and second elements, wherein the proximal and distal couplers can include an opening dimensioned to receive the endoscope therethrough when the catheter is backloaded over the endoscope.

In some embodiments, a first and/or second transverse bridge member can be provided. The first transverse bridge member can be provided to join the first and second flexible elements of the expanding system to increase the rigidity of the expanding system. The second transverse bridge member can be provided to join the third and fourth elements to increase the rigidity of the expanding system.

In some embodiments, the first and second flexible tubes are independently axially movable and independently rotatable and are removably insertable through the catheter and remain unattached to the catheter.

In some embodiments, the first and second endoscopic tools are angled toward the target tissue to achieve triangulation with the target tissue.

In some embodiments, a working instrument is insertable through a working channel of the endoscope and into the working space created by the expanding system.

In some embodiments, the instrument insertable through the flexible guides can include by way of example a grasper, a forceps, a snare, a clamp, a scissor, a knife, a dissector, an endoscopic stapler, a tissue loop, a clip applier, a suture-delivering instrument, or an energy-based tissue coagulator or cutter.

During a use of the some embodiments of the system which utilize the floating system, the channel (guide) and the endoscope form an at least substantially floating arrangement that (v) at least substantially increases the flexibility of the system over a second such system having separate lumens for a tool and an endoscope, that are affixed to the lumen throughout the length of the outer tube. The increased flexibility resulting from the floating system facilitates an ease of positioning the system in the subject for the treatment of the target tissue.

The systems provided herein can be used in several different methods of treatment. For example, the systems can be used in a method of treating a gastrointestinal lesion using a multidirectional and multi-angular approach to the lesion. The method can include positioning the system in a subject's gastrointestinal tract, the positioning including placing the retractor in proximity to a target lesion for a treatment; expanding the retractor to create the treatment space for use of the tool; improving visualization, for example, some lesions can be seen much better when tissue is retracted and stabilized; optimally positioning the target tissue in relation to the tool, for example, by optimizing the position of the duodenal papilla, facilitating its cannulation during a procedure; treating the target tissue with the tool; collapsing the retractor; and, withdrawing the system from the subject. The lesion can include, for example, a perforation, a tissue pathology a polyp, a tumor, a bleed, a diverticuli, an ulcer, a cancerous tissue, an abnormal vessel, or an appendix.

BRIEF DESCRIPTION OF THE FIGURES

FIGS. 3A-3L illustrate how a system as taught herein can be used in removing a lesion in a colon, according to some embodiments, the colon shown in a cutaway view to show the system in perspective, wherein FIG. 3A illustrates the system being inserted into the colon and having a sheath covering the retractor, FIG. 3B illustrates the retractor in the non-expanded position, FIG. 3C illustrates the retractor in the expanded position to create an asymmetric working space and further showing the endoscope in an articulated position, FIG. 3D is a view similar to FIG. 3C showing two endoscopic instruments extending from respective tool channels, FIG. 3E illustrates the tool channels and the endoscopic instruments bent toward the target lesion, FIG. 3F illustrates the lesion being removed from the wall of the colon by the endoscopic instruments, FIG. 3G illustrates the lesion removed from the wall of the colon and positioned within the retractor, FIG. 3H illustrates endoscopic instruments extending from the tool channels and bent toward the colon wall to repair the defect in the colon wall resulting from removal of the lesion, FIG. 3I illustrates placement of clamps to close the tissue defect in the colon wall, FIG. 3J illustrates the retractor in the collapsed position to capture the lesion for removal from the colon; FIG. 3K illustrates the retractor encapsulated within the sheath for removal from the colon, and FIG. 3L illustrates the closed tissue defect after completion of the surgical procedure.

FIGS. 4A-4E illustrate details of a system as taught herein, in side, axial, and oblique views of expanded and collapsed configurations, and including a stabilizer subsystem, according to some alternate embodiments, wherein FIG. 4A is a side view of the system with the retractor in the non-expanded (collapsed) position, FIG. 4B is an axial view of the system with the retractor in the non-expanded position, FIG. 4C is an axial view of the system with the retractor in the expanded position, FIG. 4D is a perspective view of the system in the position of FIG. 4A, and FIG. 4E is a view similar to FIG. 4D showing the retractor in the expanded position.

FIGS. 5A-5D illustrate side and top views of a system as taught herein, having side views and top views of expanded and collapsed configurations, according to some alternate embodiments, wherein FIG. 5A is a side view of the system with the retractor in the non-expanded (collapsed) position, FIG. 5B is a side view similar to FIG. 5A showing the retractor in the expanded position; FIG. 5C is a top view of the system with the retractor in the non-expanded position of FIG. 5A, and FIG. 5D is a top view of the system with the retractor in the expanded position of FIG. 5B.

FIGS. 6A-6D illustrate side views of a system as taught herein, having side views and cross-sections of expanded and collapsed configurations of the system, according to some other alternate embodiments, wherein FIG. 6A is a side view of the system with the retractor in a non-expanded (collapsed) position; FIG. 6B is a side view similar to FIG. 6A with a housing half removed to show internal components of the system, FIG. 6C is a side view similar to FIG. 6A showing the retractor in an expanded position, and FIG. 6D is a side view similar to FIG. 6B showing the retractor in the expanded position.

FIGS. 10A-10E illustrate an alternate embodiment of the system wherein a retractor sheath covers a retractor of a system as taught herein, according to some embodiments, wherein FIG. 10A is a top view of the system with the retractor in a non-expanded (collapsed) position, FIG. 10B is a perspective view of the system in a non-expanded position, FIG. 10C is a side view of the system with the retractor in a non-expanded position, FIG. 10D is a top view of the system showing the retractor in an expanded position, and FIG. 10E is a side view of the system showing the retractor in the expanded position.

FIGS. 17A and 17B are side views in partial cross-section showing movement of the actuator from a proximal position to a distal position to advance the rigidifying structure to stiffen the retractor system.

FIGS. 37A and 37B are transverse cross-sectional views through the outer tube showing radial movement of an intermediate portion of the floating channels within the lumen of the outer tube.

FIG. 38 is a cross-sectional view illustrating bending of the outer tube and movement of the floating channels of FIGS. 35A-35C.

DETAILED DESCRIPTION

Figure 1:
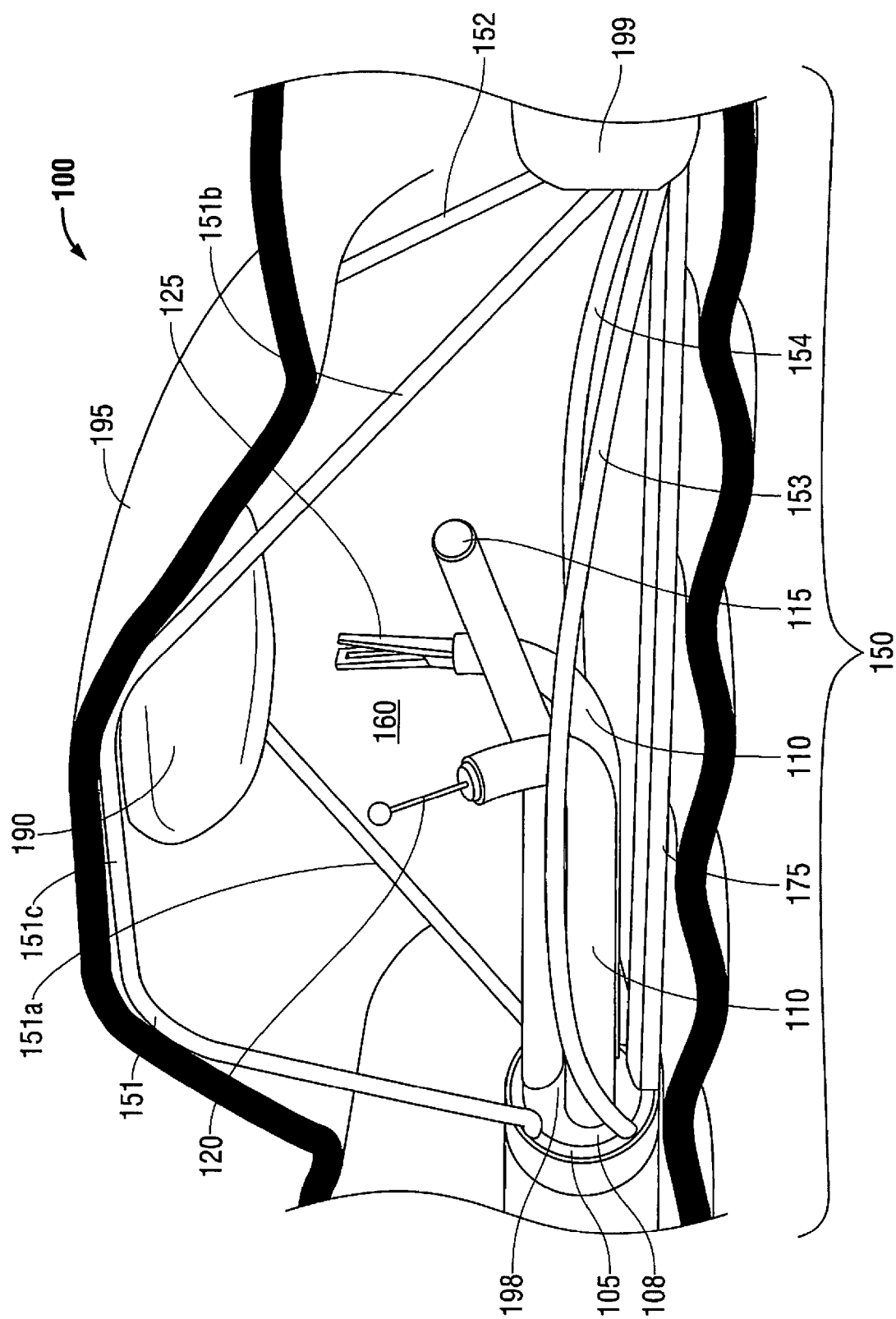
FIG. 1 illustrates a system for operatively treating gastrointestinal disorders endoscopically in a stable, yet dynamic operative environment, and in a minimally-invasive manner, according to some embodiments.

The teachings provided herein are generally directed to improved methods and devices for operatively treating gastrointestinal disorders endoscopically in a stable, yet dynamic operative environment, and in a minimally-invasive manner. The systems, for example, include an endoscopic surgical suite that is created by the systems disclosed herein. The surgical suite can have a reversibly-expandable retractor that expands to provide a stable, operative environment within a subject. In some embodiments, the expansion can be asymmetric around a stabilizer subsystem to maximize space for a tool and an endoscope to each be maneuvered independently to visualize a target tissue and treat the target tissue from outside the patient in a minimally invasive manner. Embodiments taught herein can provide, among other improvements, an increase in distance between tool ports and the target tissue to enhance the independent maneuverability and triangulation of each of the tools with respect to the target tissue. This increase in distance can also provide a way of obtaining a larger field of view. The systems taught herein, for example, can (i) enable a working space to be dynamically configured around the target tissue in tortuous body lumens and orifices such as the gastrointestinal tract using controls from outside the body;

(ii) provide a flexible, passageway for multiple surgical tools and instruments, such as endoscope and graspers to be passed from outside the body towards the target tissues; (iii) organize and/or constrain tools in the working space; (iv) at least substantially immobilize and/or stabilize the target tissue and surrounding tissue for a treatment; and/or {v) enable control over the geometry position, and orientation of the instruments such as the grasper in the working space from outside the body.

In some embodiments disclosed herein, an articulating endoscope is inserted through a channel of the catheter; in other embodiments the system is backloaded over a flexible endoscope, such as a conventional colonoscope, then the endoscope is inserted to a position adjacent the target tissue and then the catheter is advanced over the flexible endoscope so the reshaping (retractor) system (cage) is next to the target tissue.

In some embodiments disclosed herein, the endoscopic working instruments (tools) for treating the target tissue are inserted directly through a respective lumen or channel of the multi-lumen catheter. In these embodiments where the instruments (tools) are inserted directly into the lumen of channel of the catheter, the working instruments can have a curve at a distal end which automatically assumes the curved position when exposed from the catheter so it can curve toward the target tissue, or alternatively, the working instruments can have a mechanism actively controlled by the user to articulate/angle the distal tip. In other embodiments, instead of the endoscopic working instruments (tools) being inserted directly into the channel or lumen of the catheter, a flexible tube is inserted through the lumen or channel of the catheter and acts as a guide for the instrument. That is, the flexible tube is first inserted into the lumen or channel of the catheter and then the endoscopic instrument is inserted through the respective flexible tube. The flexible tube can have a curve at a distal end which automatically assumes the curved position when exposed from the catheter so it can curve toward the target tissue, or alternatively, the flexible tube can have a mechanism actively controlled by the user to articulate/angle the distal tip. In these embodiments utilizing the flexible tubes, the curving and maneuverability of the flexible tubes controls the positioning and orientation of the endoscopic instruments, and therefore the endoscopic instruments need not be provided with a pre-curved tip or articulating mechanisms.

In preferred embodiments, the systems disclosed herein include a retractor which creates an asymmetric working space within the body lumen. More particularly, when working in a confined body lumen, such as the colon, expansion of the lumen is limited because it is undesirable to over-expand which could stretch the lumen beyond its ability to return to its normal state or more dangerously could rupture the lumen. The asymmetric working spaces disclosed herein are designed to reconfigure or reshape the body lumen-transform the cylindrical space within the body lumen to a non-cylindrical asymmetrical space (i.e., changing the geometry) to shift the space around the target tissue to create more working space around the target tissue to provide both visual and mechanical improvements. Stated another way, in a cylindrical working space, there is a lot of area of unused space while in the reshaping of the embodiments disclosed herein the space is moved or shifted to reduce the unused space and create a larger area for tissue access and treatment.

The terms "treat," "treatment", and "treating" used herein include, for example, the therapeutic and/or prophylactic uses in the prevention of a disease or disorder, inhibition of a disease or disorder, and/or amelioration of symptoms of disease or disorder. The term "subject" and "patient" can be used interchangeably and refer to an animal such as a mammal including, but not limited to, non-primates such as, for example, a cow, pig, horse, cat, dog, rat, and mouse; and, primates such as, for example, a monkey or a human.

In some embodiments, the systems taught herein can include dynamically reconfigurable, asymmetric retractor structures on the distal end of a flexible and torque-able multi-channel shaft having a handle that allows for control over both the stiffness and geometry of the working space formed by the expansion of the retractor. In some embodiments, the retractor can include a stabilizer subsystem having 2-8, 3-5, 4-6, or any range therein, flexible retractor elements. In some embodiments, the retractor elements can be aligned at least substantially parallel to each other when fully collapsed for positioning in the patient. In some embodiments, the retractor elements are aligned on planes that are within about 5-30 degrees, about 10-25 degrees, about 15-20 degrees, about 15 degrees, or any range therein, of each other. In some embodiments, the retractor elements form a frame that has a length ranging from about 4-12 cm. 6-10 cm, 7-9 cm, 5-11 cm, or any range therein. In some embodiments, the frame is about 8 cm long. In some embodiments, the retractor elements form a frame that has a width ranging from about 1-5 cm. 2-4 cm, or any range therein. In some embodiments, the frame is about 3 cm wide. In some embodiments, the retractor elements form a frame that has a height ranging from about 1-5 cm. 2-4 cm, or any range therein. In some embodiments, the frame is about 3 cm high. One of skill will appreciate that there are a number of suitable materials that can be used to make the retractor elements for the purposes set-forth herein. In some embodiments, the retractor elements can be made from NITINOL. In some embodiments, the retractor element can comprise multifilament steel wires or polymer cords. The polymer materials can include polyetheretherketone (PEEK), nylon, polyester, polycarbonate, polyurethane, or polyethylene. The gauge of the retractor elements can vary, depending on material. In some embodiments, the retractor elements can comprise wires that range from about 0.020"–0.40" in diameter. In some embodiments, the retractor elements are about 0.030" in diameter.

The term "about" is used in the teachings herein to describe possible variations in amounts or ranges that can be used in embodiments. It can be used in embodiments, for example, to include the exact amount or range specified, as well as a variation of which that would not create a substantial difference in function. A difference in function can be insubstantial, for example, where it is less than 20% in some embodiments, less than 15% in other embodiments, less than 10% in yet other embodiments, or perhaps even less than 5% in yet other embodiments. One of skill will appreciate that the percentage difference in function required for to be substantial will depend on the function of the embodiment itself that is under comparison.

The methods, devices, and systems taught herein can be used for minimally-invasive procedures. A non-invasive procedure, in contrast, can be defined as a procedure that includes no violation of the skin or the mucosa, and no appreciable damage to any other tissues of the body. A minimally-invasive surgical operation, on the other hand, involves minimal access trauma and minimal collateral tissue damage during a surgical operation. The terms "minimal," "minimize," "minimizing," "minimized," "avoid," "avoiding," "avoided/ can be used interchangeably in some embodiments. Minimally-invasive surgery is desirable, for example, to reduce trauma to the patient, speed the healing process, reduce risk and, thus, reduce the length and expense of a hospital stay by minimizing or avoiding tissue damage, or risk of tissue damage. Tissue damage, or the risk thereof, can be minimized or avoided, for example, where a procedure is designed to minimize or avoid unnecessary tissue contact that may otherwise be associated with a procedure. The gentle procedures taught herein, for example, are directed to preserving tissue during a gastrointestinal surgery.

The systems taught herein can be dynamic in some embodiments, for example, such that the tissue retraction can include partial or complete expansion or collapse of a retractor to facilitate an increase or decrease in the distance between instruments and the target tissue, which is useful in reconfiguring the work space and aiding in axial movements of the tools. By increasing and releasing the tension, the amount of tissue to be placed in the working space can also be better-gauged during a procedure, for example, and tissuetraction-contra-traction can be facilitated to help in creating a dissecting plane during a removal of tissue. One of skill will appreciate having the ability to dynamically reconfigure the working space and optimize traction-contra-traction on the target tissue, as this can facilitate surgical manipulations.

The systems disclosed herein also enable triangulation to be achieved. Tissue triangulation, wherein the tissue is triangulated between two endoscopic instruments, enhances access and maneuverability.

FIG. 1 illustrates a system for operatively treating gastrointestinal disorders endoscopically in a stable, yet dynamic operative environment, and in a minimally-invasive manner, according to some embodiments. The system 100 can include a multi-lumen-catheter retractor system for ease of positioning in a subject, and such systems can be designed to provide a minimally invasive treatment of the subject. The system 100 can have a flexible outer tube 105 configured for guiding one or more channels 110 and an endoscope 115 within the system 100. The flexible outer tube 105 can have a lumen (not shown), a proximal end (not shown), and a distal end 108 to house, for example, the channel(s) and the endoscope during use of the system 100. The lumen can extend from the proximal to the distal end so the tool channels 110 can be manipulated at a proximal end by the user. The outer tube 105 can alternatively be a multi-luminal tube, so a separate lumen accommodates the endoscope and the individual tool channels, and during the use of the system 100, the channel 110 can serve as a guide through which a tool 120,125 can be inserted and manipulated in a treatment of a target tissue 190 in the gastrointestinal tract 195 (or other areas} of the subject. The channel 110 can, for example, be in operable contact with an independently manipulable-and-articulable tool, the channel having an elevator component for moving a bendable section. Thus, the length of the channel in some embodiments is sufficient so it can extend out the proximal end of the outer tube 105 for manipulation by the user. The tool channels are bendable or articulable at a distal end so they angle away from the longitudinal axis and toward the target tissue 190. Such bendability can be achieved by providing tool channels (guides) 110 of shape memory material with a shape memorized bent position as shown in FIG. 1. When contained within the lumen of the outer tube 105 for insertion, the tool channels 110 would have a substantially straightened position, and when advanced from the distal end of the outer tube 105, would return to the bent position of FIG. 1. Other materials could also be utilized. In alternate embodiments, the tool channel 110 can have a mechanism such as an elevator component or a control wire attached to a distal end which can be pulled by the user or pulled by an actuator to move the tool channel to the bent position. These different ways to achieve bendability (articulation) of the tool channels can be used for the various embodiments of the systems described herein.

In some embodiments, the tool inserted through the tool channel can be any tool known to one of skill. For example, the tool 120,125 can include a grasper, a forceps, a snare, a scissor, a knife, a dissector, a clamp, an endoscopic stapler, a tissue loop, a clip applier, a suture-delivering instrument, or an energy-based tissue coagulator or cutter. The bendability of the channel 110 for moving a bendable section, often a distal end of the channel 110, manipulates, i.e., bends, the tool 120,125 positioned therein. In some embodiments, at least one channel 110 and/or the endoscope 115 can have at least substantial freedom to move within the outer tube 105 during operation, or "float," such that the system 100 can be considered to be a floating, multi-lumen-catheter retractor system. It should be appreciated that the terms "tool" and "instrument" can be used interchangeably in some embodiments taught herein. As can be appreciated, the tool 120,125 can be flexible, at least at a distal end such that when the tool channel 110 bends in a manner described above, it also bends the tool which is positioned therein. Alternatively, it is also contemplated that the tool 120,125 can be articulable or controllably bendable or composed of shape memory or other material so it bends without reliance on the bendability of the tool channels 110.

Although two tool channels 110 are illustrated, it should also be appreciated that a system with more than two tool channels or with only one tool channel can also be utilized. Additionally, the endoscope can have a working channel for insertion of a working instrument such as a grasper or dissector.

It is also contemplated that the tools can be provided with bendability characteristics so that they can be inserted directly through the lumen of the outer tube 105 without the need for tool channels. In these embodiments, the tools themselves have the bendable or articulable feature so as not to rely on the tool channels for bending/angling toward the target tissue.

In some embodiments, the system can comprise a stable, yet dynamic operative environment in that it can include a reversibly-expandable retractor 150, as shown in FIG. 1, that expands to form a treatment space or working chamber 160 in the subject. The retractor 150 can be configured, for example, for the expansion to occur distal to the distal end 108 of the outer tube 105. In some embodiments, the retractor can at least substantially render the target tissue 190 aperistaltic for the treatment. The retractor 150 can have a variety of configurations to serve, for example, as a scaffolding within the gastrointestinal tract 195. For example, the retractor 150 can include retractor elements 151,152, 153,154, along with a proximal coupler 198 operably connected to the retractor elements 151,152,153,154, whether at least substantially attached and/or at least slidably-engaged to the retractor elements 151,152,153,154, and a distal nexus or hub (or coupler) 199 for a distal point of an operable connection with the retractor elements 151,152,153,154.

In the embodiment of FIG. 1, retractor element 151 is a flexible element having a proximal portion 151*a* extending from the proximal coupler 198 at a first angle, a distal portion 151*b* extending from the distal hub or coupler 199 at a second angle preferably different from the first angle, and an engaging portion 151*c*, which engages the tissue, extending between the proximal and distal portions 151*a*, 151*b*. As shown, portion 151*a* extends at a greater angle to the longitudinal axis than distal portion 151*c* providing an asymmetric expansion of the retractor element itself. Thus, the length of the distal portion 151*b* exceeds the length of proximal portion 151*a*. Retractor element 152 can be similarly configured and angled as retractor element 151, or alternatively of a different configuration and angle. Retractor elements 151 and/or 152 can alternatively be configured so the proximal and distal portions are of the same length and angles. Note the retractor elements 151, 152 expand in a direction to one side of the longitudinal axis. This asymmetric expansion creates an asymmetric chamber described below.

The retractor 150 can be a reversibly-stabilized and reversibly-expandable retractor, the retractor 150 forming an asymmetrical treatment space 160 upon the expansion. And, the retractor 150 can be configured to reversibly stiffen an otherwise flexible arrangement of the retractor 150, the arrangement designed to facilitate ease of positioning of the system 100 in the subject and to reversibly stiffen for the expansion of the retractor 150. The stabilization of the retractor 150 can, in some embodiments, include a stabilizer subsystem for stabilizing the retractor 150 as taught herein, the stabilizer having, for example, an at least substantially-rigid beam 175 to support the expanded retractor 150.

Rigidifying the retractor systems as disclosed in the various embodiments herein, i.e., by utilizing a substantially rigid beam, advantageously stabilizes the retractor system, i.e., limits bending of the distal tip which could otherwise occur due to the opposing force of the tissue during expansion. Thus, the stabilizer carries the load and works to create a more stabilized chamber. In some embodiments, beam 175 can be substantially rectangular in cross-section, substantially circular in cross-section or of other cross-sectional shapes. It can be provided of a stiffer material than the retractor elements. In some embodiments, the beam can have a cross sectional dimension larger than a cross sectional dimension of the retractor element. As shown in FIG. 1, the beam 175 is at the base of the chamber formed by the retractor elements, with the retractor elements extending radially (laterally) away from the beam 175. The beam 175 can be formed by the more rigid element exposed when the retractor elements are exposed from the outer tube for expansion, or alternatively, can be advanced independently from within the outer tube as in some of the embodiments described in more detail below.

In some embodiments, the outer tube can have any dimensions believed to be useful to one of skill for the purposes taught herein. For example, the outer tube can have an outer diameter ranging from about 3 mm to about 30 mm, about 5 mm to about 25 mm, about 7 mm to about 22 mm, from about 9 mm to about 20 mm, from about 11 mm to about 18 mm, from about 8 mm to about 15 mm, from about 10 mm to about 16 mm, or any range therein in increments of 1 mm. The length of the outer tube can range, for example, from about 30" to about 72", from about 31" to about 36", from about 28" to about 80", from about 32" to about 40", from about 34" to about 38", or any range therein in increments of 1".

The outer tube can be manufactured from any materials know to be useful to one of skill for the purposes taught herein. For example, the outer tube can comprise a polymer, or perhaps a polymer having an embedded wire reinforcement. The wire reinforcement can be a mesh, a braid, a helical coil or any combination thereof. The wire reinforcement can include any material believed by one of skill to be useful for the purposes set-forth herein. For example, wire reinforcement can comprise a material having an elastic modulus that is about 1-3 orders of magnitude higher than the polymer tube. The wire material can comprise, for example, a stainless steel having a diameter ranging from about 0.003" to about 0.017", about 0.005" to about 0.015", about 0.010" to about 0.012", or any range therein in increments of about 0.001". The tube hardness, or durometer, can be any of that which one of skill will find useful for the purposes set forth herein. For example, the hardness can range, for example, from about 50 Shore A to about 60 Shore A, about 40 Shore A to about 80 Shore A, about 45 Shore A to about 70 Shore A, or any range therein in increments of 1 Shore A. One of skill will appreciate that the outer tube should be flexible, elastically bendable, but sufficiently stiff torsionally to transmit torque from the handle or proximal end of the system to the retractor or distal end of the system.

The outer tube can be connected to at a distal end to a ring, referred to herein as the proximal coupler in some embodiments, which can have portals formed therein for retractor elements to slide through, as well as a desired orientation and positioning of the channels for the endoscope and at least one tool, such that the retractor elements, endoscope, and at least one tool are organized relative to each other in a predetermined manner to achieve a particular function, such as an increase in working space, a better view of a plane of dissection, or any other procedural variable deemed of interest to one of skill. For example, in the embodiment shown in FIG. 1. the portals for the retractor elements are spaced radially outwardly from the portals for the endoscope and the tool channels.

In some embodiments, the retractor structures taught herein for substantially immobilizing the lesion to the extent desired for the treatment. For example, the current use of loops and a piece-meal removal of flat or wide-based polyps, such as those having a base of about 1 cm or wider, may not provide clear surgical margins, whereas the systems taught herein can, in some embodiments, immobilize or affix the entire circumference of the bowel wall around the treatment area and facilitate the production of clear surgical margins. One of skill will appreciate having a working space that can be provided by the systems taught herein, the working space being (i) at least substantially non-collapsible, (ii) at least substantially aperistaltic; and, (iii) at least substantially affixed at a particular point in the abdominal cavity in relation to any fixed body point, like a hip, for example. This is a significant improvement over existing systems, as existing systems have not addressed many existing problems including, for example, bowel collapse that can result from an air leak from the working space; peristalsis that is normal, even in a sedated patient; and, additional undesired bowel movements caused by the patient's breathing, movement of the scope or other instrument manipulation, or perhaps even by a surrounding peristalsis causing movement at a treatment area. Such problems are addressed by systems taught herein. As such, systems taught herein can offer a rigid, stable structure having at least substantial resistance to a variety of moving forces in the abdomen that are typically present during a gastrointestinal endoscopic procedure. One of skill will appreciate decreasing the effects of these moving forces on the working space to help reduce otherwise inherent technical complexities, limited efficacies, and decreased safety during endoscopic procedures.

In addition to creating the working space with the above advantages, the working space is formed to create a sufficient working distance for the tools for treatment, e.g., polyp dissection, to enhance maneuvering and manipulating the individual tools, enabling tissue triangulation. Working space distance is also advantageously formed to enhance visibility of the target tissue.

In some embodiments, the systems taught herein can be slidably positioned over an endoscope during use. In these embodiments, the endoscope would first be inserted to a position adjacent the target tissue and then the multi-lumen tube or catheter advanced over the endoscope, with the endoscope sliding over the endoscope receiving lumen (channel) of the outer tube or catheter. In fact, it should be appreciated that there are a variety of methods of using systems taught herein that are already used by one of skill in current state-of-the-art procedures. For example, the method can include inserting the multi-luminal tube into an overtube, cover, or sheath. And, in some embodiments, the endoscope can be a colonoscope. In many embodiments, regardless of the method of use, the retractor structures can mechanically retract one side of the colonic wall in an asymmetric manner to increase the distance between the target lesion and the opposite wall, as well as between the lesion and the instruments in their most retracted, but visualized, position to increase the effective work space.

In some embodiments, the systems can include a multi-lumen catheter having at least 2 working channels for manipulating tools and an endoscope, each of the two working channels having 6 degrees of freedom that are independent from each other and the endoscope. The ability to independently manipulate the endoscope and tools allows, for example, one instrument to retract the tissue or lesion away or substantially perpendicular to another instrument, for example, the dissecting instrument, while independently optimizing the endoscope's position and, hence, the view of the treatment area. This would facilitate the removal of tissue with clear margins. The channels can manipulate the tools with several degrees of freedom, 6 degrees of freedom in some embodiments, providing a greatly enhanced maneuverability in the working area when compared to current state-of-the-art systems. In some embodiments, the at least one independently manipulable-and-articulable tool can be independently rotatable to an angle of up to about 360 degrees, about 315 degrees, about 270, about 225 degrees, about 180 degrees, about 135 degrees, or about 90 degrees in the working area. In addition the tools can be independently bendable to an angle of up to about 180 degrees, about 135 degrees, about 90 degrees, or about 45 degrees in at least one direction in the working area.

The systems taught herein can provide for organizing the orientation of the floating channels, in order to further facilitate improving the flexibility of the system. In some embodiments, for example, the proximal coupler, the ring that can be attached to the distal end of the outer tube, can be used to organize the tools and endoscope in a particular arrangement to facilitate a particular positioning of the tools as they emerge from the shaft into the working space created by the retractor. In some embodiments, the tool channels can be placed further than the endoscope from the retractor elements that expand the most. Likewise, the proximal end of the outer tube can also have respective openings for each of the channels, and these openings can be, for example, a part of a handle coupler, or the handle itself, operably connecting one or more of the channels to the outer tube. The operable connection between the outer tube and channels can provide for controlling the endoscope and tools, for example, from outside the patient. The rings can be made of any material believed by one of skill to be suitable for the purposes discussed herein. For example, the rings can be made of stainless steel, or perhaps a plastic such as polycarbonate or acrylonitrile butadiene styrene (ABS).

It should be appreciated that, in some embodiments, the systems taught herein can include any combination of components, the selected combination of which is designed to be operable with components that are obtained separate from the system. For example, the system can include an outer tube and a retractor component, the outer tube being operable with at least one channel obtained separately and an endoscope obtained separately. Likewise, the system can include an outer tube, a retractor, and an endoscope, and the channels are obtained separately; or an outer tube, a retractor, and a channel, the endoscope obtained separately. Moreover, the system can include an outer tube, a retractor, an endoscope, and at least one channel; or, a handle, an outer tube, a retractor, an endoscope, at least one channel, and at least one tool.

The terms "substantial," and "substantially" can be used, for example, to refer to a relative measure for a parameter. It can be used in some embodiments, for example, to refer to a degree of change or function that relates to an amount, a performance, or some other characteristic. The following are for purposes of example in describing general embodiments: As described, the systems can be considered to be floating systems, can have a floating channel, a floating endoscope, multiple floating channels, or a combination thereof, in some embodiments. For example, the phrase, "an at least substantially floating arrangement within the system", can refer to an arrangement, for example a channel or endoscope arrangement, that can have some attachment that restricts movement in at least one direction, a minimal attachment to minimize such restriction of movement, or perhaps no attachment at all, to another system component. For example, a channel or endoscope can be arranged to be at least substantially floating in the outer tube relative to a second such system that does not use a floating-type arrangement to increase flexibility, or inherently achieve an increase in flexibility, of the second such system. As such, in many embodiments, the endoscope and/or channel can have a substantial portion of its arrangement unattached within the system, allowing the substantial portion to "float" or move substantially freely within the outer tube. The "substantial portion" can be, for example, a percentage of the arrangement that must remain unattached within the system to provide a performance characteristic, such as an increased flexibility of the system when compared to the second such system that does not use a floating-type arrangement to increase flexibility, or inherently achieve an increase in flexibility, of the second such system.

The phrase, "at least substantially render the target tissue aperistaltic for the treatment", for example, can refer to the target tissue having some minimal peristalsis, or perhaps no peristalsis, under the conditions of normal use to provide a performance characteristic, such as controlling movement of the target tissue to facilitate treatment. The phrase, "at least substantially attached", for example, "at least substantially attached to the lumen of the outer tube", for example, can refer to a component having a fixed attachment or moveable attachment. In some embodiments, the attachment can be between the component and the lumen, such that there is a loss of at least one degree of freedom of movement of the component. For example, the component can slide and/or rotate in relation to the lumen of the outer tube, as long as the sliding and/or rotating occur in relation to a particular fixed point on the lumen. Likewise, "at least substantially attached" can, of course, mean "fixed", "reversibly fixed," or the like, in some embodiments. Likewise, "at least slidably-attached" can refer to an attachment between components that allows for at least sliding motion between components such as, for example, a sliding motion between a port and a tube. In some embodiments, an endoscope can be at least slidably-attached, for example, where the scope is allowed to slide in the direction of the scope's central axis in and out of a port, such that the distance that the scope extends beyond the port is adjustable. And, in some embodiments, a component can be "at least slidably-attached" where it can slide as well as move in other directions. For example, the port can be substantially larger than the scope, in some embodiments, such that the scope can slide axially, as well as move side-to-side, align its central axis parallel to the central axis of the outer tube, or perhaps, misalign its central axis to not be parallel to the central axis of the outer tube.

The phrase, "at least substantially increases the flexibility" can refer to an orientation of components that enhances the flexibility of a system when compared to another orientation and design of the components. For example the phrase "at least substantially increases the flexibility of the system over a second such system" can refer to a comparison of flexibility of the claimed system over the second system not having the floating arrangement under the conditions of normal use, such that the flexibility of the system has increased to a minimal amount that improves the ease of positioning the system in the subject for the treatment of the target tissue.

The phrase, "at least substantially rigid component," can refer to a component that is rigid, or sufficiently rigid, such that the desired function is obtained, under the forces that are created with normal use. For example, a desired function may be to prevent or inhibit the occurrence of a bending moment of the rigid component at one or more points along the length of a retractor upon expansion of the retractor in the subject. In some embodiments, the systems taught herein can have a retractor with four retractor elements, at least two of which are expandable in the subject to create a working space for a treatment. In this example, the expansion of the at least two retractor elements toward the target tissue to create the working space requires a force sufficient to retract the tissue and, creates an opposing force in the opposite direction that can create the bending moment in the rigid component. One of skill should appreciate that such a bending moment can be problematic, for example, where it contributes to an instability that affects the user's control over the position of the retractor during a treatment of the target tissue. In such embodiments, a component that prevents or inhibits the bending moment can be "at least substantially rigid," for example, where the user retains a desired level of control, or at least sufficient control, over the position of the retractor during the retraction of the target tissue. In some embodiments, a component that prevents or inhibits a bending moment, whether in or out of the subject, can be at least substantially rigid where the bending of the component due to the expansion of the retractor creates a deflection that ranges from 0.0 to about 5 degrees, about 1.0 degree to about 10 degrees, about 2.0 degrees to about 12 degrees, about 3.0 degree to about 10 degrees, about 1.0 degree to about 15 degrees, about 1.0 degree to about 9.0 degrees, about 1.0 degree to about 8.0 degrees, about 1.0 degree to about 7.0 degrees, about 1.0 degree to about 6.0 degrees, about 1.0 degree to about 5.0 degrees, about 1.0 degree to about 4.0 degrees, or any range therein in increments of about 0.1 degree. In some embodiments, the deflection of the rigid component cannot exceed about 1.0 degree, about 2.0 degrees, about 3.0 degrees, about 4.0 degrees, about 5.0 degrees, about 6.0 degrees, about 7.0 degrees, about 8.0 degrees, about 9.0 degrees, about 10.0 degrees, or any 0.1 degree increment therein. The bending can be measured, for example, as a point of deflection from the original position of the rigid component's axis from force created on the rigid component through the expansion.

The terms "substantial" or "substantially" can be used interchangeably in some embodiments, and can be described using any relative measures acceptable by one of skill. For example, relative percentages can be used to indicate a substantial amount, substantial change, substantial difference, substantial function, or the like. In some embodiments, the percentage can be greater than 10%, greater than 20%, greater than 30%, greater than 40%, or greater than 50%. In some embodiments, the percentage can be greater than 60%, greater than 70%, or greater than 80%. And, in some embodiments, the percentage can be greater than 90%, greater than 95%, or in some embodiments, even greater than 99%. For example, a substantial [amount]" or a "substantial [change]", can include any amount or change relative to a reference parameter. The amount or change, for example, can include an increase or decrease relative to the reference parameter, can be compared to a reference point for the parameter. The deviation from the reference point can be, for example, in an amount of at least 1%, at least 2%, at least 3%, at least 5%, at least 10%, at least 15%, at least 20%, at least 25%, at least 30%, at least 35%, at least 40%, at least 45%, or any 1% increment therein. Also, for example, a "substantial [function]" or "substantially [functioning]" limitation can serve as a comparison to a reference function parameter, to indicate a deviation that will still provide the intended function. Reference functions can include, for example, floating, aperistalsis, attaching, flexing, rigidity, a position or positioning relative to another object, and the like. The deviation from the reference point can be, for example, in an amount of less than 1%, less than 3%, less than 5%, less than 10%, less than 15%, less than 20%, less than 25%, less than 30%, less than 35%, less than 40%, less than 45%, or any 0.1% increment therein. For example, a component can have an acceptable, substantial [function] when it deviates from the reference by less than the acceptable deviation.

As such, the system can include a floating, multi-lumen-catheter retractor system for ease of positioning in a subject, and such systems can be designed to provide a minimally invasive treatment of the subject. In some embodiments, the systems comprise a highly flexible outer tube configured for guiding a floating channel and/or a floating endoscope in an at least substantially floating arrangement within the system. This flexible outer tube can have a lumen, a proximal end, and a distal end. And, during a use of the system, the floating channel can serve as a guide through which a tool is manipulated in a treatment of a target tissue in a subject. In some embodiments, the tool can include a grasper, a forceps, a scissor, a knife, a dissector, an endoscopic stapler, a tissue loop, a clip applier, a suture-delivering instrument, or an energy-based tissue coagulator or cutter. And, in some embodiments, the floating channel can have an elevator component for moving a bendable section to manipulate the tool. In some embodiments, at least one channel and/or the endoscope can have at least substantial freedom to move within the outer tube during operation, or "float," such that the system can be considered to be a floating, multi-lumen-catheter retractor system as taught herein.

Likewise, the system can also comprise a stable, yet dynamic operative environment in that it can include a reversibly-expandable retractor (working space expanding system) that expands to form a treatment space in the subject. The retractor can be configured, for example, for the expansion to occur distal to the distal end of the outer tube and at least substantially render the target tissue aperistaltic for the treatment; wherein, during a use of the system in a subject, the floating channel can be at least substantially attached to the lumen of the outer tube at a first proximal location and a first distal location, and be at least substantially floating in the lumen of the outer tube between the first proximal location and the first distal location. Likewise, during the use of the system, the floating endoscope can be at least slidably-attached to the lumen of the outer tube at a second proximal location and a second distal location, and be at least substantially floating in the lumen of the outer tube between the second proximal location and second distal location. And, during the use of the system, the at least substantially floating arrangement can at least substantially increase the flexibility of the system over a second such system, the second such system having a lumen for a tool and an endoscope affixed to the lumen throughout the length of the outer tube between the proximal end and the distal end of the outer tube. The increased flexibility of the at least substantially floating arrangement can facilitate an ease of positioning the system in the subject for the treatment of the target tissue. Moreover, the retractor can be a reversibly-stabilized and reversibly-expandable retractor, the retractor forming an asymmetrical treatment space upon the expansion. And, the retractor can be configured to reversibly stiffen an otherwise flexible arrangement of the retractor, the flexible arrangement designed to facilitate the ease of positioning of the system in the subject and to reversibly stiffen for the expansion of the retractor.

Figure 2A:
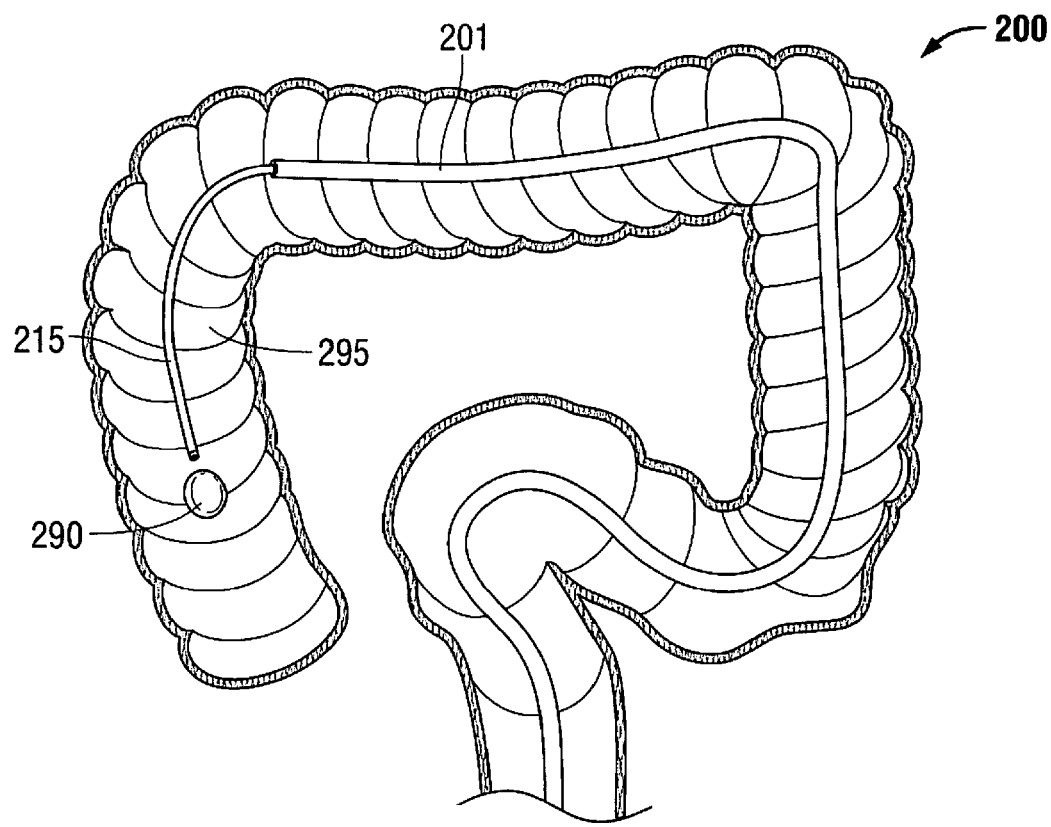
FIGS. 2A and 2B illustrate how a system as taught herein can be positioned for treating a lesion in the ascending colon, according to some alternate embodiments.
Figure 2B:
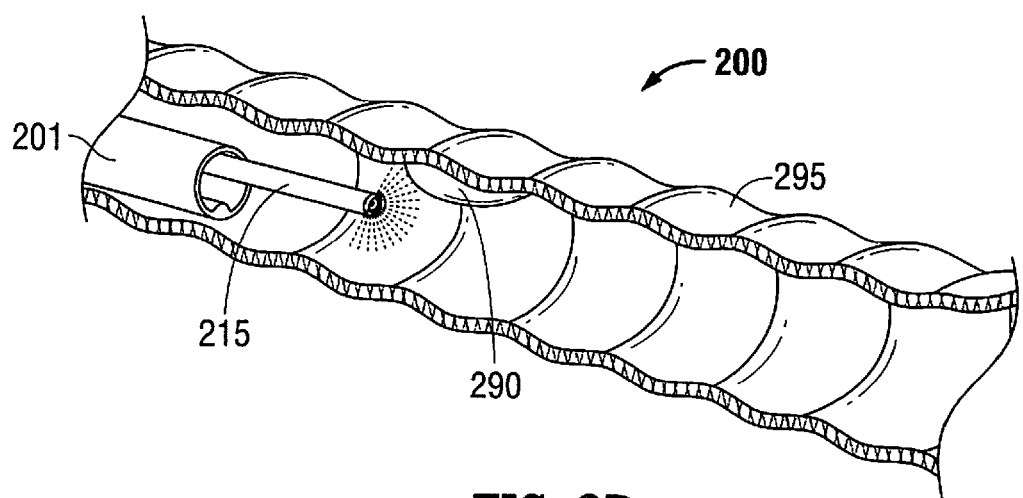

FIGS. 2A and 2B illustrate how a system as taught herein can be positioned for treating a lesion in the ascending colon, according to some embodiments. It should be appreciated that any series of steps and methods known to one of skill to be useful in the positioning 200 can be used with systems taught herein. FIG. 2A illustrates how an endoscope 215 can be used to locate the lesion, a target tissue 290 in a portion of the ascending colon 295. FIG. 2B illustrates how the multi-lumen-catheter retractor system 201 can be guided to the target tissue 290 using the endoscope 215 as a guide for the positioning 200 of the system in the treatment of the target tissue 290. As can be appreciated, the multi-lumen catheter is advanced over the endoscope 215 as shown in FIG. 2B.

Figure 3A:
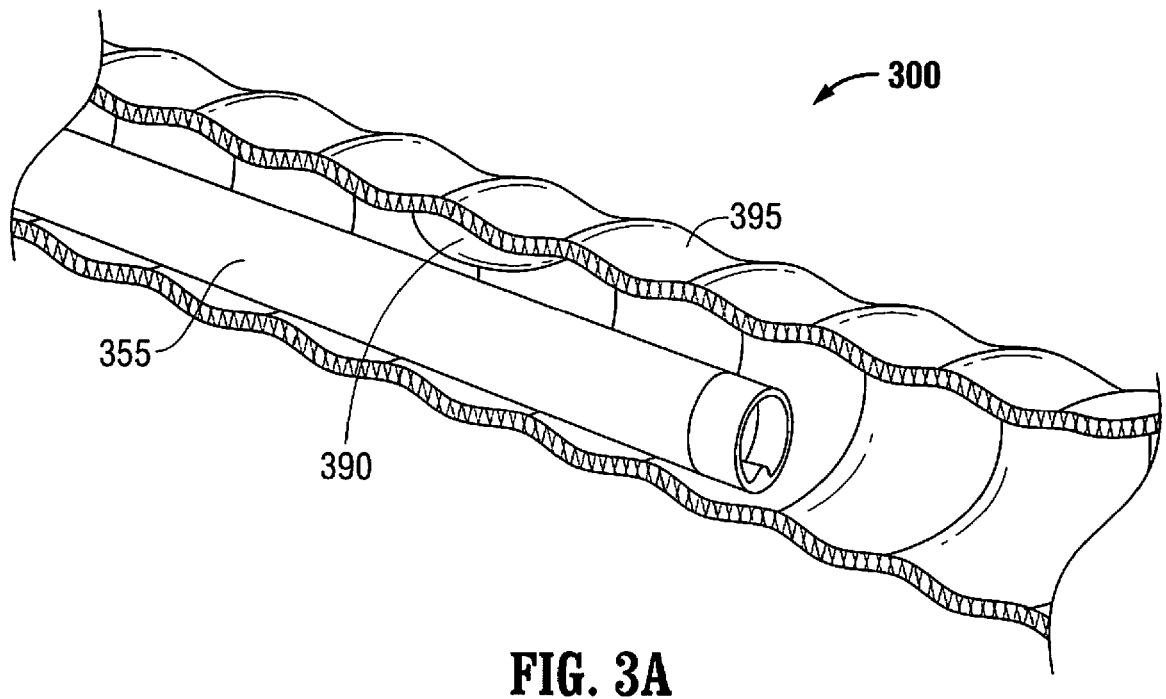
Figure 3B:
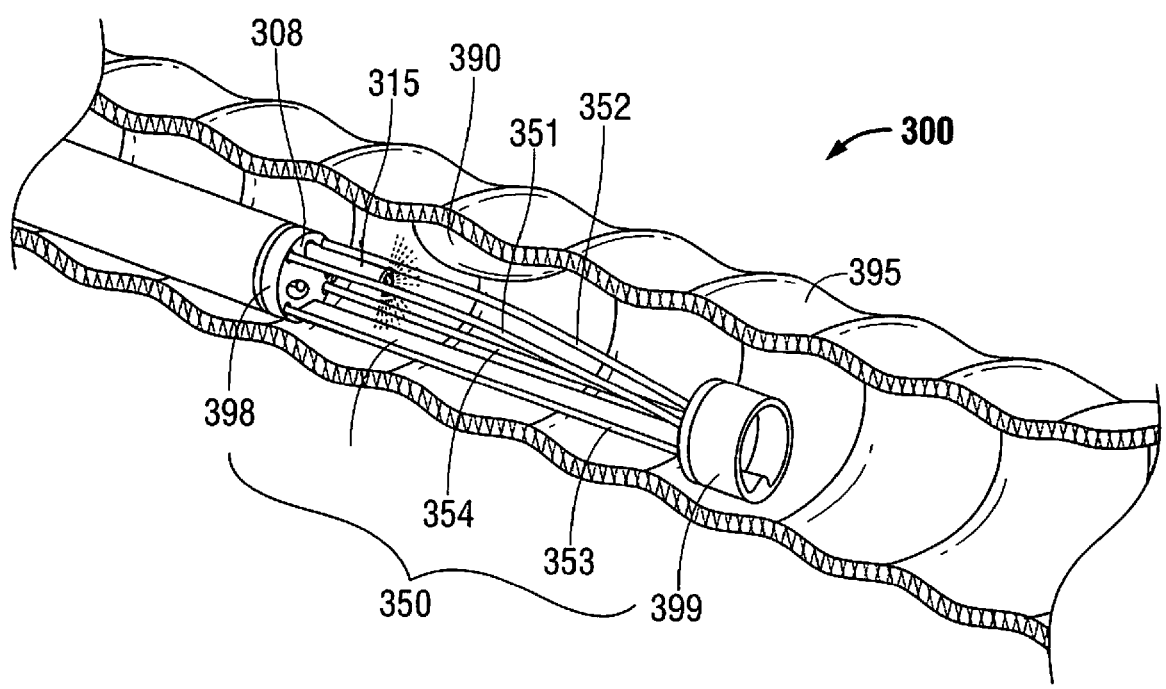
Figure 3C:
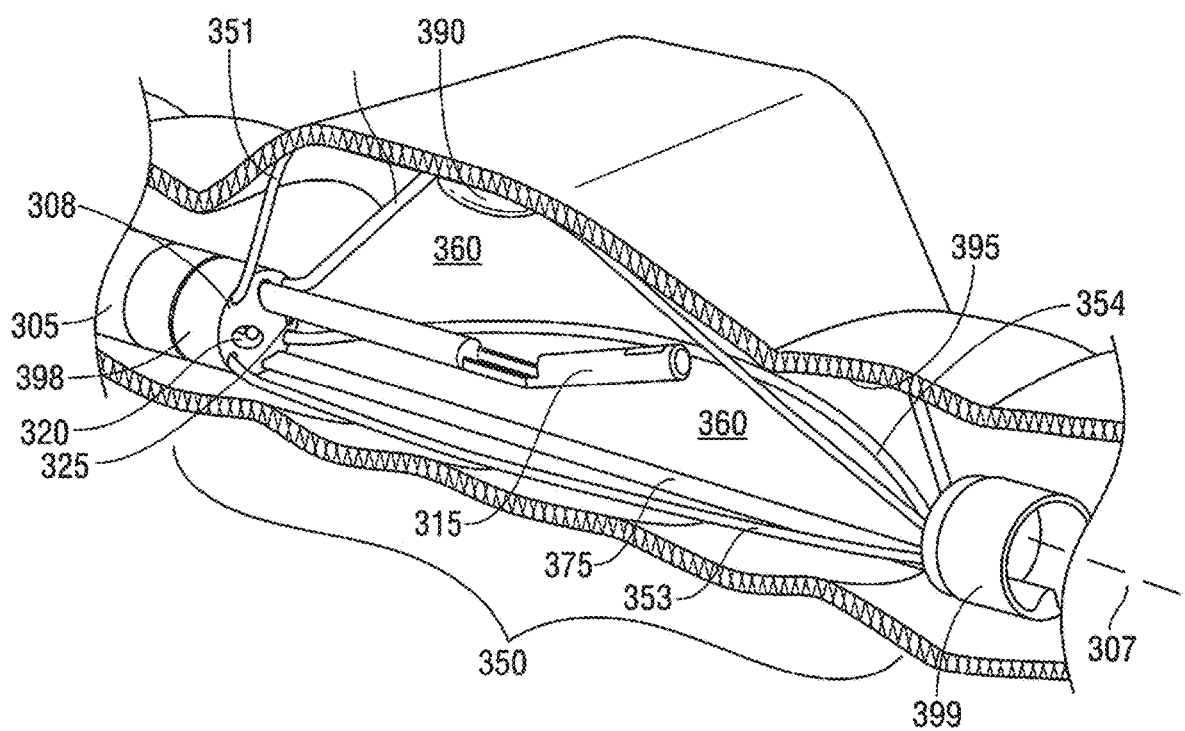

FIGS. 3A-3L illustrate how a system as taught herein can be used in removing a lesion in a colon, according to some embodiments. As noted above, the system can also be used in other areas of the patient's body and to treat other target tissue. The description herein regarding removal of a polyp from the wall of the colon is shown and described by way of example as the system (as well as the other systems disclosed herein) can be used for other surgical applications and in other body spaces. The system can be positioned as in FIGS. 2A and 2B in the treatment 300 of a gastrointestinal lesion 390, and a multidirectional and multi-angular approach to the lesion can be used. As in FIGS. 2A and 2B, for example, the approach can include identifying a lesion in a gastrointestinal lumen of a subject using an endoscope 315; and, forming a substantially rigid and stable endoluminal working area for treating a target tissue, the gastrointestinal lesion 390. In FIG. 3A, the system is positioned at the lesion 390, and in FIG. 3B, the expandable retractor 350 is exposed for subsequent expansion to create an asymmetrical working space 360 (FIG. 3C). In FIG. 3A, a sheath or cover 355 is positioned over the retractor elements to facilitate insertion, with the distal end of the sheath 355 abutting the distal coupler 399 or alternatively overlying the distal coupler. After insertion to the target site, the sheath (or outer tube) 355 is removed to expose the retractor elements for subsequent expansion. as shown in FIG. 3B. It should also be appreciated that, alternatively, the retractor elements can be biased to an expanded position and retained in a collapsed delivery position by the sheath 355. In such embodiments, removal of the sheath 355 to expose the retractor elements would enable the retractor elements to automatically expand to their expanded position of FIG. 3C.

Figure 3D:
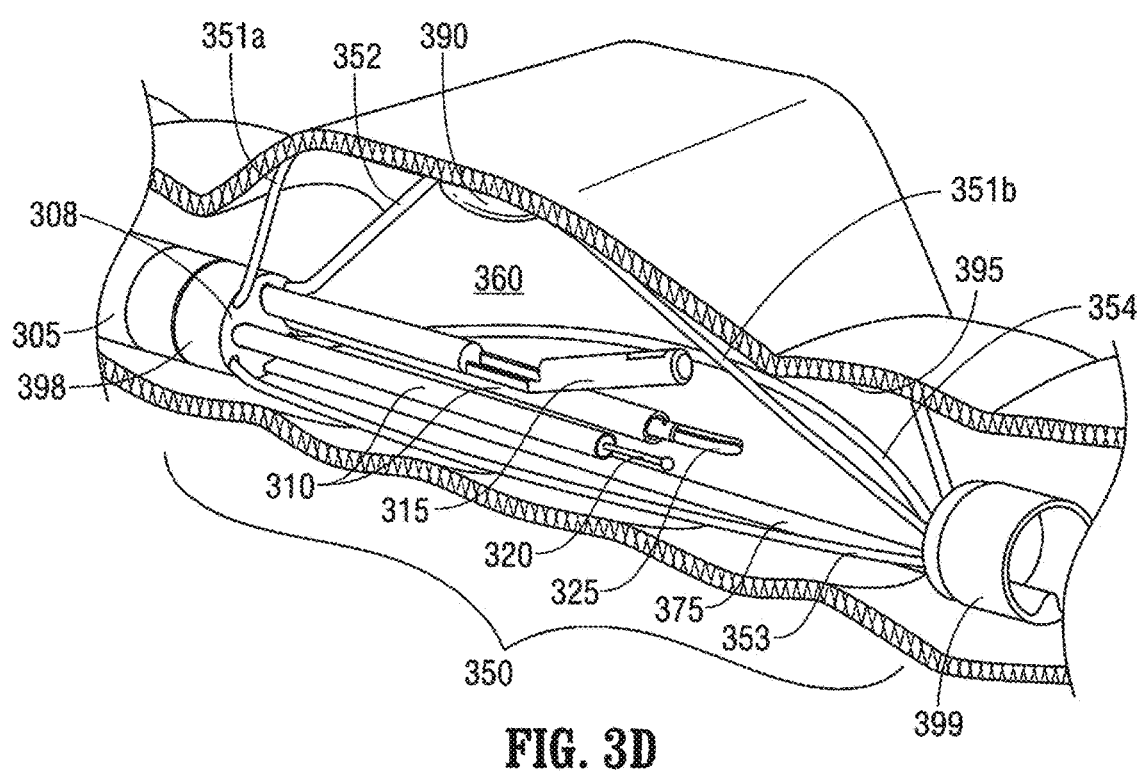

FIGS. 3C and 3D illustrate the creation of the working space 360 within the body lumen, and manipulation of the endoscope 315 and tools 320,325. After positioning the retractor 350 in proximity to the lesion 390, the retractor 350 is expanded to form the asymmetrical working space 360 for the treating of the lesion 390. The retractor 350 in some embodiments can be expanded by moving distal coupler 399 and proximal coupler 398 relative to one another, wherein as the distance between the couplers 399, 398, shortens, the retractor elements are forced more laterally with respect to the longitudinal axis of the outer tube (catheter) 305. In alternate embodiments, the retractor elements can be operably connected to an actuator such that the actuator is moved to bow the retractor elements such as in the embodiment of FIG. 11 discussed in detail below. In still other alternative embodiments, the retractor elements can be composed of a shape memory or other material such that when exposed from the outer tube or sheath, they automatically return to their expanded configuration, e.g., their shape memorized expanded configuration. When such shape memorized retractor elements are utilized, once exposed they would automatically move from the position of FIG. 3B to the position of FIG. 3C.

The system can have any configuration taught herein, such as (i) at least one independently manipulable-and-articulable scope 315 to be used in viewing the lesion 390,
(ii) at least one tool channel 310 for at least one independently manipulable-and-articulable tool 320,325 to be used in the treating of the lesion 390, and (iii) the retractor 350, which can be an asymmetrically expandable structure. In some embodiments, the retractor 350 can be expanded asymmetrically toward the lesion 390, the expanding including a portion of the retractor 350 pushing on tissue surrounding the lesion 390 to increase the working area (space) within the body space (lumen) by providing an asymmetrical working area and thus facilitate an entry of the lesion 390 into the working area 360 for the treating. The retractor 350 can be located distal to the distal end of the outer tube 305 and the asymmetrical working area 360 can be substantially rigid and stable relative to the independently manipulable-and-articulable scope 315 and the at least one tool 320,325 to facilitate treating the lesion 390. The treating of the lesion 390 can include, for example,
(i) viewing the lesion 390 with the articulating scope 315 and (ii) using the at least one tool 320,325 in the treatment of the lesion 390 with a multidirectional and multi-angular approach to the lesion 390 in the asymmetrical working area 360.

In the embodiment of FIGS. 3A-3J, four retractor elements are provided. Two retractor elements 353, 354 are at the base of the retractor system and can have an outwardly bowed or arcuate shape, or alternatively, a substantially straight shape, or have accurate and substantially straight portions. Two retractor elements 351, 352 expand more radially outwardly to apply a force against the wall of the colon on which the lesion is found. These retractor elements are described in more detail below.

In some embodiments, the independently manipulable-and-articulable scope 315 and the at least one tool 320,325 can be independently movable axially in the working area 360, independently rotatable in the working area 360, and independently bendable in at least one direction in the working area 360. Accordingly, in some embodiments, the portion of the retractor 350 pushing on the tissue surrounding the lesion 390, e.g. retractor elements 351, 352, can be expanded further from the central axis 307 of the distal end of the outer tube 305 than other portions of the retractor to provide an even larger working area 360 for the treating of the lesion 390 when compared to a second such structure that merely expands symmetrically around the central axis 307 of the distal end of the outer tube 305. This is due to the fact that it is desirable to create the largest working distance from the instrument tips to the target tissue, achieved by changing the configuration, i.e., reshaping, of the colon in the target area, but without overstretching, damaging or rupturing the colon.

Note that after the retractor system is expanded as shown in FIG. 3C, the endoscope 315 can be articulated in the working space 360 toward the target lesion 390 to improve visibility.

Figure 3E:
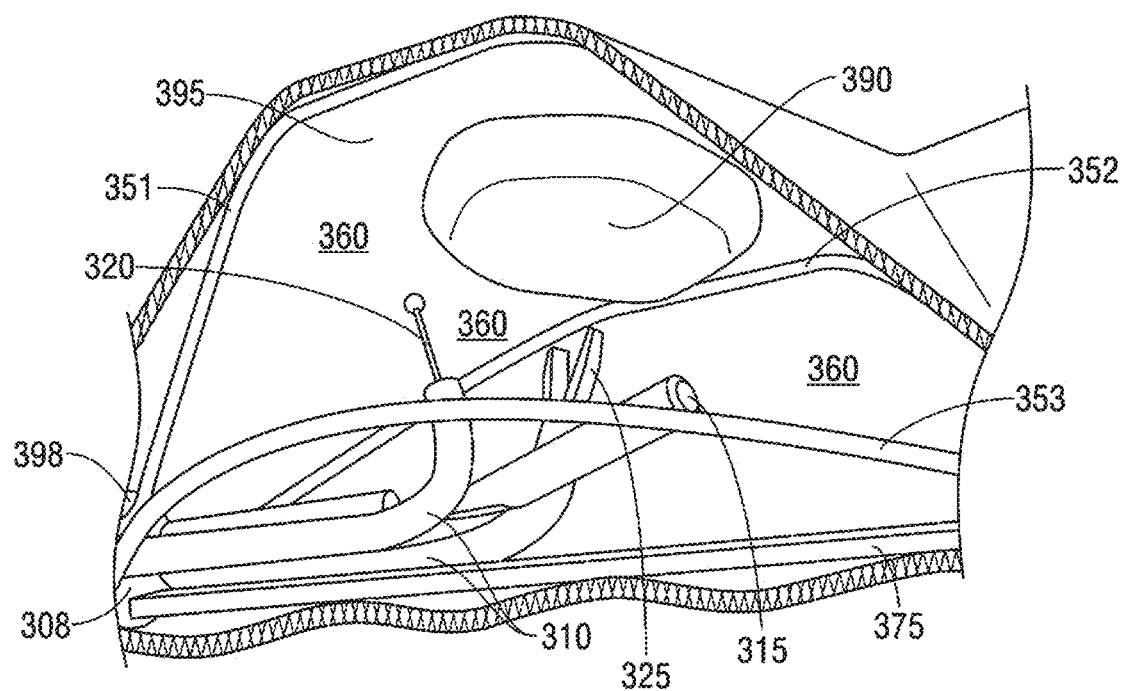

FIG. 3E illustrates a multidirectional and multi-angular approach to the lesion 390, showing the step of positioning the work area 360, endoscope 315, and tools 320,325 in relation to the lesion 390. After the retractor 350 is expanded as shown in FIG. 3C, the user of the system can view and approach the lesion 390 with the tools 320,325 from nearly any desired angle within the working space 360. The tool channels 310 are advanced through the respective lumens in the multi-lumen catheter or tube and the endoscopic tools or instruments are inserted through the tool channels 310, with the distal ends of the tools extending distally of the tool channel 310 as shown in FIG. 3D. The advantages of the tool channels are described below in more detail in conjunction with the embodiment of FIG. 11, and such advantages are applicable to this and other embodiments utilizing the tool channels. As noted above, it is also contemplated that in alternative embodiments, the endoscopic tools can be inserted directly into the lumens of the catheter or tube, without the use of tool channels, provided they have the bending/articulating characteristics described above which enable their manipulation without the use of bendable/articulatable tool channels.

Figure 3F:
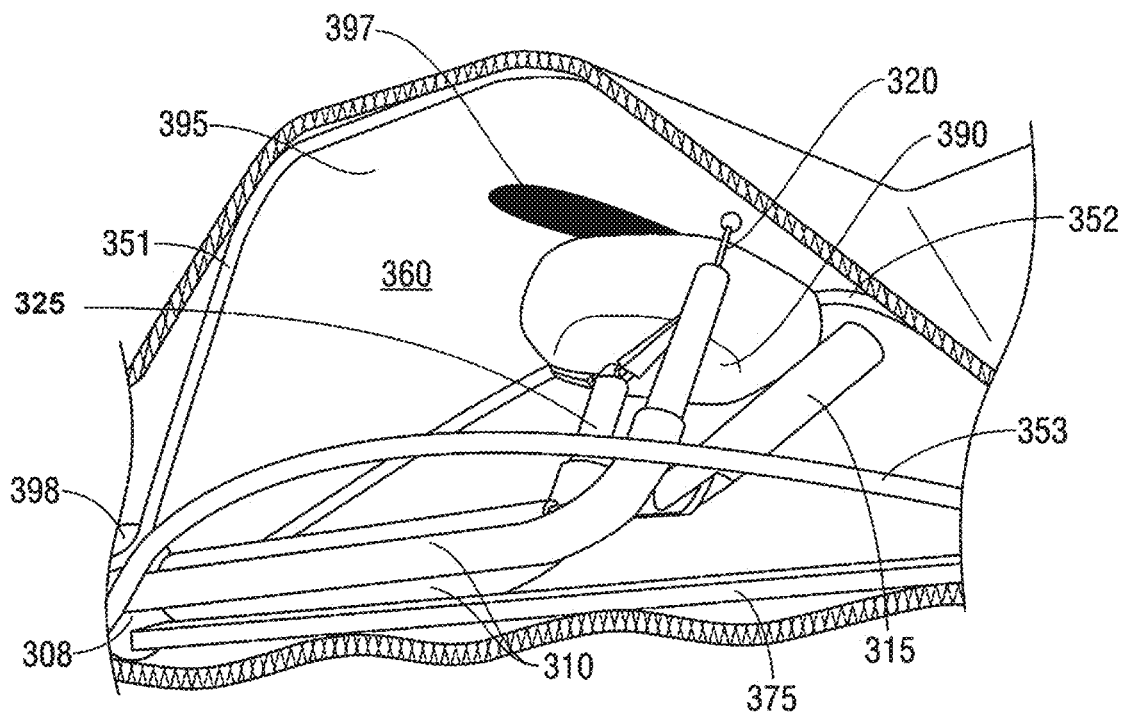
Figure 3G:
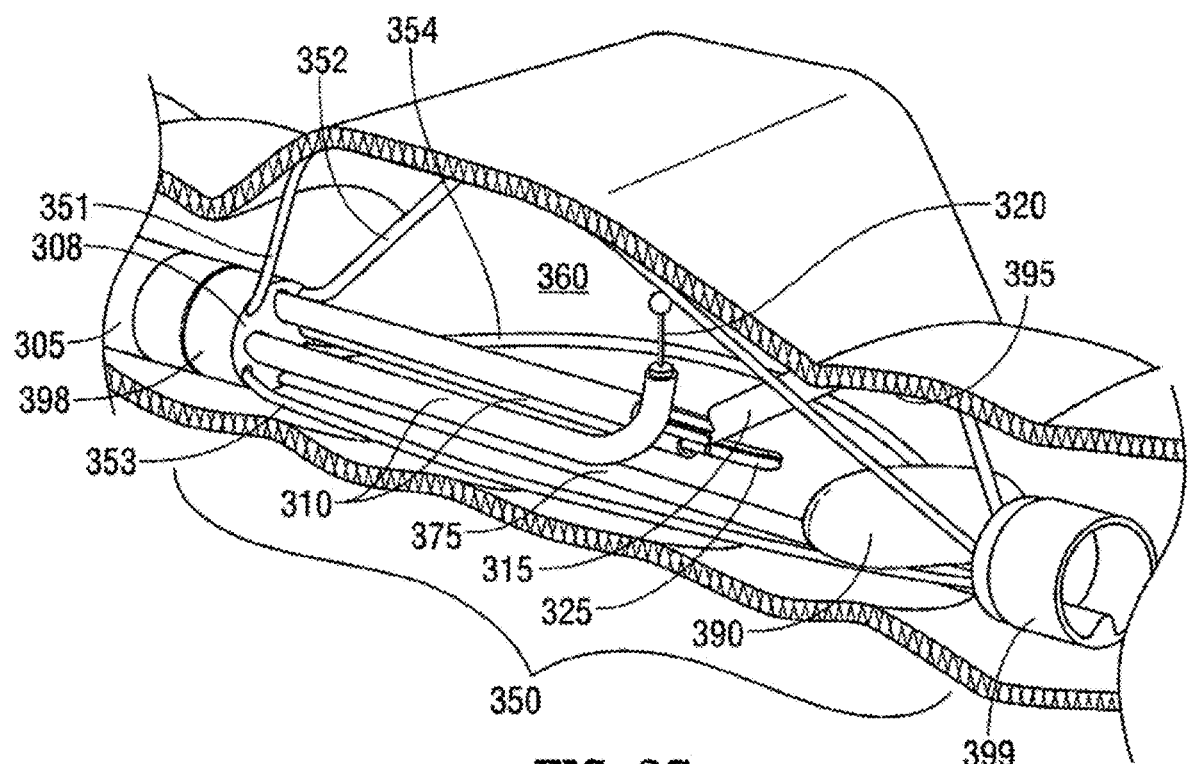
Figure 3H:
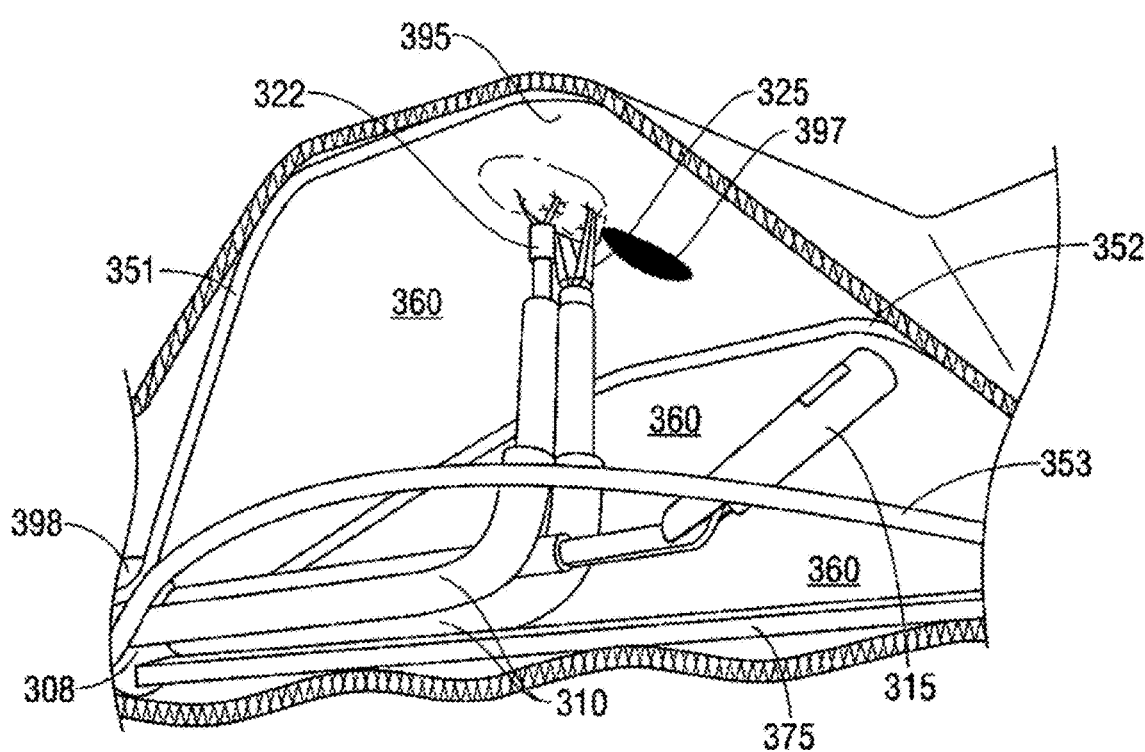
Figure 3I:
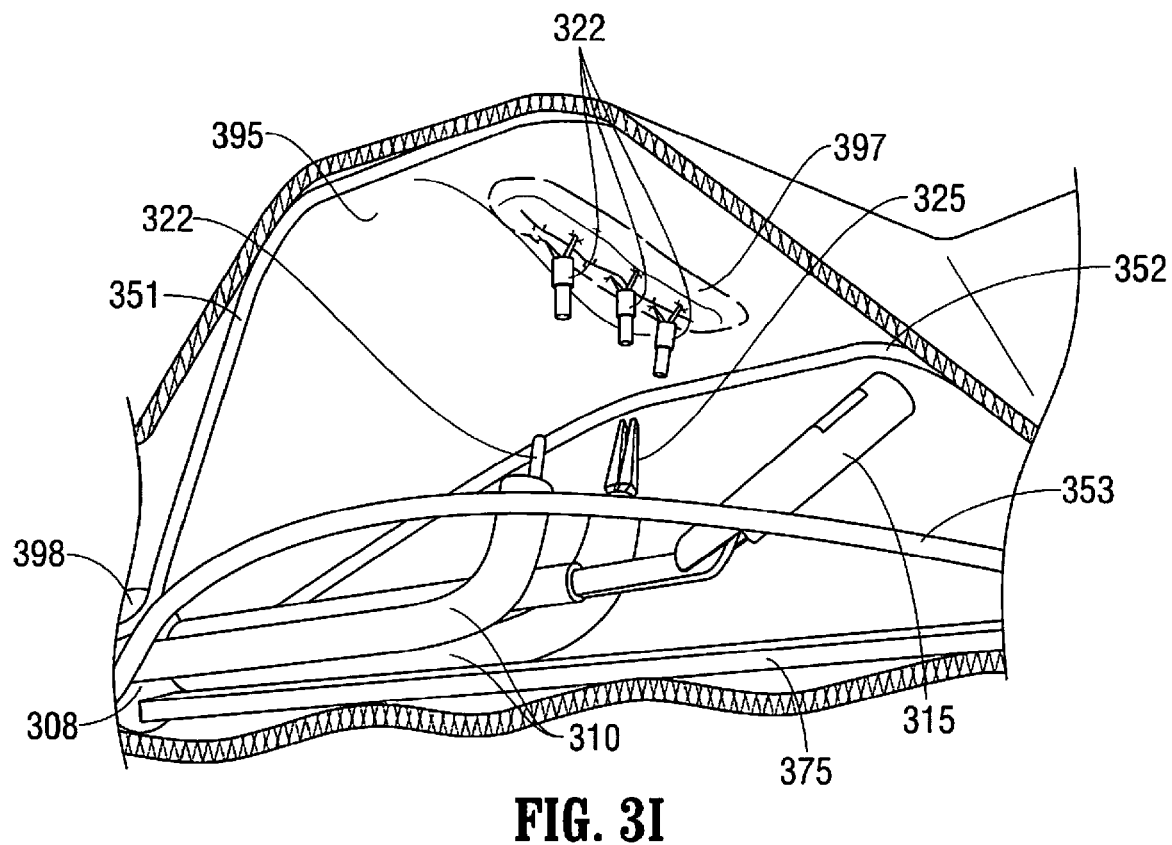
Figure 3J:
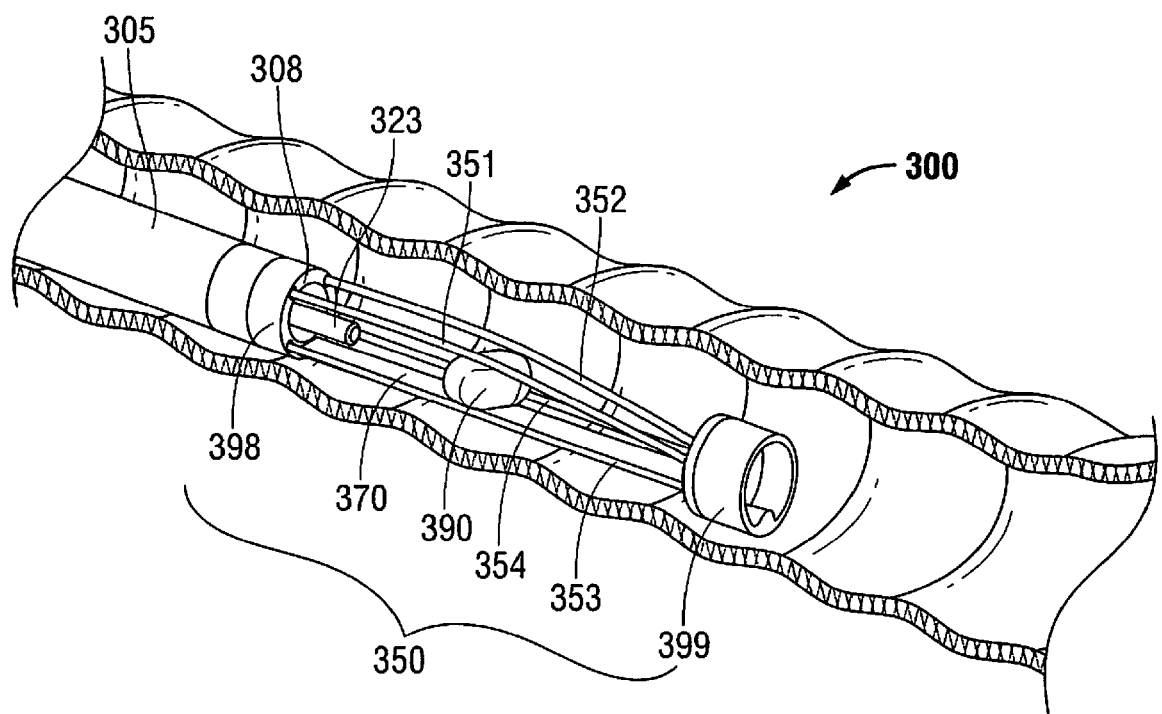
Figure 3K:
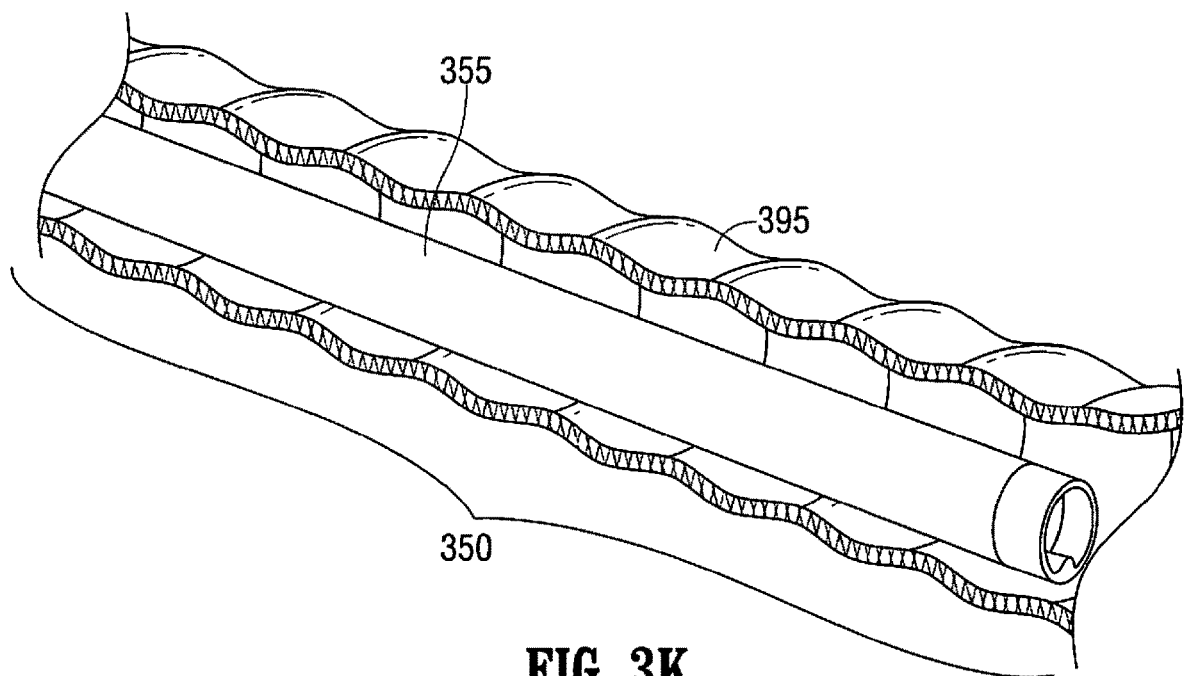
Figure 3L:
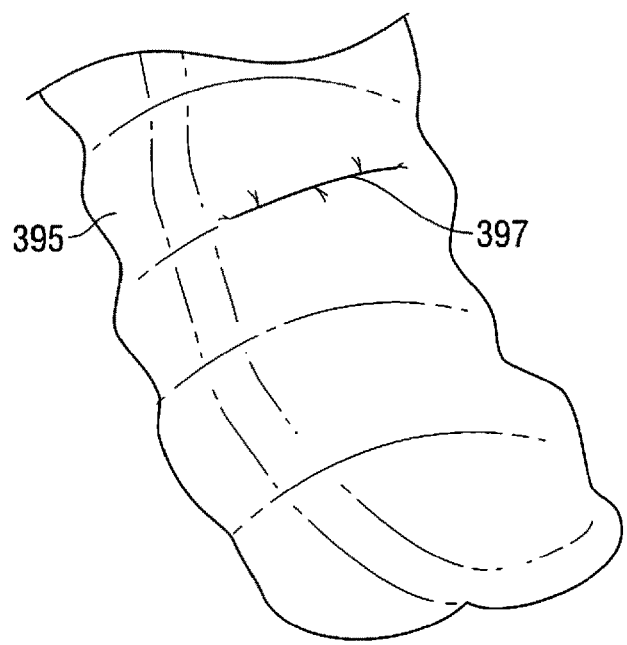

FIG. 3F illustrates the versatility of the system, showing the step of removing the lesion 390 using tool 320 to excise the lesion 390 from an independently chosen first angle, while tool 325 can be used to grasp the lesion 390 from an independently chosen second angle and endoscope 315 can be used to view the lesion 390 from an independently chosen third angle. As shown, the different angling of the tools 320 325 advantageously achieve tissue triangulation to facilitate access, maneuverability and removal of the lesion. After the excision of the lesion 390 from the gastrointestinal tract 395 by the dissection tool 320, a tissue defect 397 remains. Note the dissection tool 320 can in some embodiments be in the form of an electrosurgical instrument, although other dissecting/excising tools can also be utilized. FIG. 3G illustrates the step of releasing the excised lesion 390 into the retractor assembly in preparation for completion of the procedure. FIGS. 3H and 3I illustrate the step of closing the tissue defect 397, showing that tool 320 for excision of the lesion 390 has been replaced by tool 322 for closure of the lesion. The lesion can be closed by various methods such as mechanical (e.g., clips staples or structures), glue, electrosurgical energy, etc. FIGS. 3J and 3K illustrate the steps of capturing the lesion 390 for removal using tool 323 and collapsing the retractor 350 to capture and contain the lesion 390 within the collapsed retractor elements 351, 352, 353, 354 in preparation for removal of the system from the subject, including the use of an optional retractor cover 355 or other sheath or sleeve which can be slid over the catheter to further encapsulate the lesion retained within the collapsed retractor elements. FIG. 3L is a view of the closed tissue defect following completion of the treatment.

In some embodiments, as shown for example in FIGS. 3B-3J, the system can comprise a stable, yet dynamic operative environment in that it can include a reversibly-expandable retractor 350 that expands to form a treatment space 360 in the subject. The retractor 350 can be configured, for example, for the expansion to occur distal to the distal end 308 of the outer tube (catheter) 305. In some embodiments, the retractor can at least substantially render the target tissue 390 aperistaltic for the treatment. The retractor 350 can have a variety of configurations to serve, for example, as a scaffolding within the gastrointestinal tract 395. For example, the retractor 350 can include retractor elements 351,352,353,354, along with a proximal coupler or hub 398 operably connected to the retractor elements 351, 352,353,354, whether at least substantially attached and/or at least slidably-engaged to the retractor elements 351,352, 353,354, and a distal nexus or coupler 399 for a distal point of an operable connection with the retractor elements 351, 352,353,354. The distal nexus or hub 399 is shown in the shape of a ring, although it can be virtually any shape desirable to one of skill, such as a cone, hemisphere, sphere, and the like, and it may or may not include a port for passage of the endoscope beyond the distal end of the system. As noted above, in some embodiments, the proximal coupler 398 can be moved toward the distal coupler 399, the distal coupler moved toward the proximal coupler 398, or both couplers moved toward each other to reduce their distance to force the retractor elements radially outwardly. The extent of outward expansion of the retractor elements can be controlled by controlling the distance between the proximal and distal couplers 398, 399, The retractor can be repeatedly moved between expanded and retracted positions as desired by adjusting the distance between the coupler 398, 399. Such controlled expansion of the retractor elements can also be achieved by operatively coupling the proximal end of the retractor elements to an actuator as in the embodiment of FIG. 11. Alternatively, as noted above, the retractor elements can be composed of a material, e.g., shape memory material, to automatically expand when exposed from a catheter or sheath.

In the expanded position of the retractor elements as shown, retractor element 351 is a flexible element having a proximal portion 351a extending from the proximal coupler 398 at a first angle, a distal portion 351b extending from the distal hub or coupler 399 preferably at a second angle different from the first angle, and an engaging portion 351c, which engages the tissue, extending between the proximal and distal portions 351a, 351b. As shown, portion 351a extends at a greater angle to the longitudinal axis than distal portion 351b providing an asymmetric expansion of the retractor element itself. Thus, the length of the distal portion 351b exceeds the length of portion 351a. Retractor element 352 can be similarly configured and angled as retractor element 351, or alternatively of a different configuration and angle. Retractor elements 351 and/or 352 can alternatively be configured so the proximal and distal portions are of the same length and angles. Note the retractor elements 351, 352 expand in a direction to one side of the longitudinal axis. This asymmetric expansion creates an asymmetric chamber (working space). Retractor elements 351, 352 can extend in an arcuate or bowed manner or substantially straight manner as mentioned above. In some embodiments, the retractor elements 351, 352 only expand in one direction with respect to the longitudinal axis of the catheter so they remain above (as viewed in the orientation of FIG. 3D) a longitudinal plane containing the longitudinal axis. In some embodiments, only elements 351, 352 expand while elements 353, 354, which form the base of the retractor (cage) remain in substantially the same position in the insertion (collapsed) and expanded position of the retractor. Note as with the retractor elements of FIG. 1, the elements 351, 352, 353, 354 can be covered with a plastic or other material to create a covered chamber as in the embodiment of FIG. 10A described below.

The retractor 350 can be a reversibly-stabilized and reversibly-expandable retractor, the retractor 350 forming an asymmetrical treatment space 360 upon the expansion. And, the retractor 350 can be configured to reversibly stiffen an otherwise flexible arrangement of the retractor 350, the arrangement designed to facilitate ease of positioning of the system 300 in the subject and to reversibly stiffen for the expansion of the retractor 350. The stabilization of the retractor 350 can, in some embodiments, include a stabilizer subsystem as taught herein, the stabilizer having, for example, an at least substantially-rigid beam 375 to support the expanded retractor 350. The substantially rigid beam 375 can be substantially rectangular in cross-section, substantially circular in cross-section or of other cross-sectional shapes. It can be provided of the same or of a stiffer material than the retractor elements. It helps to create a more stabilized chamber as described herein. As shown, the beam 375 is at the base of the chamber formed by the retractor elements, with the retractor elements extending radially (laterally) away from the beam 375. The beam 375 can be formed by the more rigid element exposed when the retractor elements are exposed from the outer tube for expansion, or alternatively, can be advanced independently from the outer tube or formed by advancement of a rigidifying structure as in some of the embodiments described in more detail below.

Figure 4D:
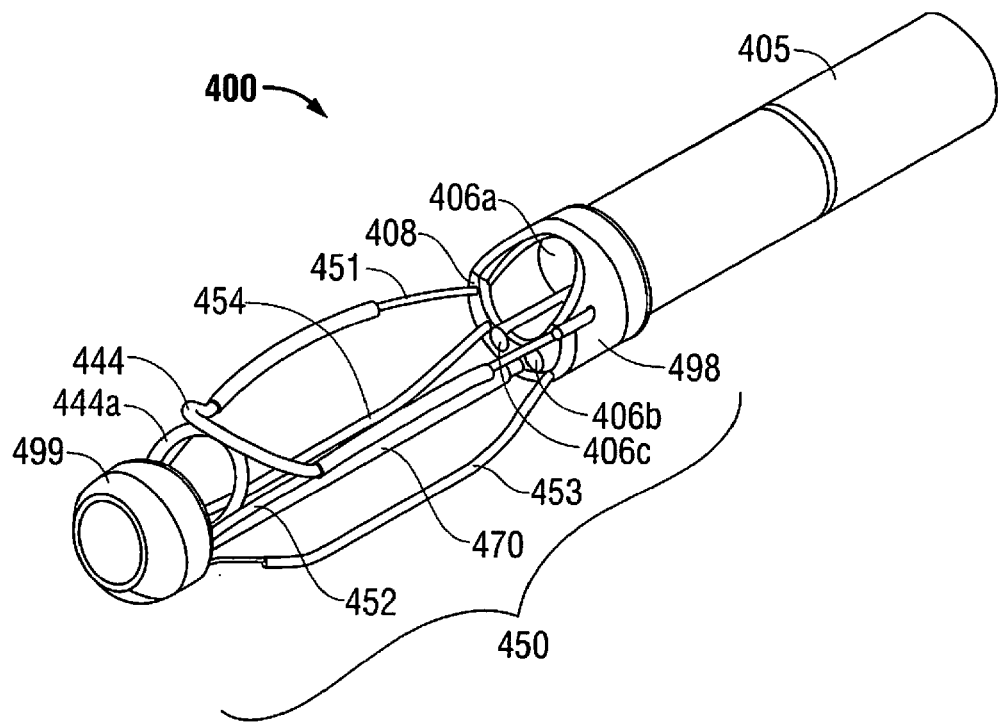

FIGS. 4A-4E illustrate details of an alternate system as taught herein, in side, axial, and oblique views of expanded and collapsed configurations, and including a stabilizer subsystem, according to some embodiments. The figures illustrate an example of a multi-lumen catheter system which is similar to the system of FIGS. 3A-3K in that it has a reversibly-stabilized and reversibly-expandable retractor for a minimally invasive treatment of a subject. FIGS. 4A-4C illustrate side and axial views that show that the system 400 can comprise a flexible outer tube (or catheter) 405 for guiding a tool channel (not shown) and an endoscope (not shown) within the system 400 in the same manner as system 300. The flexible outer tube 405 has a lumen, a proximal end (not shown), and a distal end 408. The one or more tool channels (not shown) serves as a guide through which an endoscopic tool (not shown) can be manipulated in a treatment of a target tissue in a subject in the same manner as tool channels 310 of FIG. 3G manipulate tools 320, 325. In some embodiments, the retractor 450 can be a reversibly-stabilized and reversibly-expandable retractor 450 forming a treatment space upon expansion and configured for the expansion to occur distal to the distal end 408 of the outer tube 405. The retractor 450 can be designed to reversibly-stiffen an otherwise flexible arrangement of the retractor 450, the flexible arrangement designed to facilitate the positioning of the system in the subject and to reversibly-stiffen for the expansion of the retractor 450. In these embodiments, the reversibly-stiffened arrangement of the retractor 450 can form an at least substantially-rigid beam 475 from an otherwise flexible beam 470 as a structural support for the expansion of the retractor 450. In some embodiments, the stabilizer subsystem can include the flexible beam 470, which may comprise a flexible tube, and a way for creating the at least substantially-rigid beam 475. This, as taught herein, can include all embodiments taught herein, including the mechanisms for slidably-engaging an at least substantially-rigid rod or beam, for example, within the flexible rod or beam 470 prior to expanding the retractor. In some embodiments, the terms "rod" and "beam" can be used interchangeably and, in some embodiments, the terms "beam" and "tube" can be used interchangeably. The beam 475 can be configured and function in the same manner as described above for beam 375, including the alternatives described herein.

In some embodiments, the flexible beams taught herein in each of the embodiments disclosed can comprise a polymer, such as polyimide, polyether block amides (PEBAX), nylon, polyethylene, polyurethane, polyvinylchloride (PVC), PEEK, or polytetrafluoroethylene (TEFLON). One of skill will appreciate that the flexible beams can be reinforced tubes made from components and designs known to the art. The flexible beam can be, for example, a flexible tube that is reinforced with metal wires, braids, or coils that include, for example, a metal such as a stainless steel or NITINOL. In some embodiments, the flexible tube can be kink resistant and transmit torque. And, in some embodiments, the flexible tube can comprise a combination of both flexible sections and rigid sections. In these embodiments, a flexible section can lie between rigid sections, for example. Such flexible tubes can include composites of overlapping tubes joined using any method known to one of skill, including bonding using epoxy or cyanoacrylates, in some embodiments.

In some embodiments, any of the systems taught herein can include a bridge member to add stability to the retractor. For example, the retractor system 450 can include a bridge member 444 configured to maintain a desired orientation of the retractor elements 451,452,453,454 during the expansion, the bridge member 444 operably stabilizing at least two 451,452 of the four retractor elements 451,452,453,454. That is, in the embodiment of FIG. 4A, the bridge member 444 is attached to the two retractor elements 451, 452 which are configured to expand laterally outwardly to expand or reconfigure the tissue wall. The bridge member 444 creates a transverse structure for the elements 451,452, limiting side-to side movement. As shown, bridge member 444 can also include a second bridge section 444a connected to bridge 444 and to retractor elements 452 and 453 thereby connecting all four retractor elements 451, 452, 453, 454. The upper surface (as viewed in the orientation of FIG. 4B) can be arcuate as shown. The bridge member 444 can be a separate component or alternately integrally formed with one both of the retractor elements 451, 452. The bridge member can be composed of a material similar to the elements 451, 452 or can be composed of a different material.

Additional bridge members can be provided on the retractor elements 451, 452 to increase stability. Note that one or more bridge members can be used with the other retractor embodiments disclosed herein. Note that the bridge member 444 can, in some embodiments, in the collapsed position, angle radially outwardly from the longitudinal axis such as in FIGS. 4B and 4D, but change to angle more radially inwardly in the expanded position of FIGS. 4C and 4E.

Additionally, an additional bridge member (or multiple bridge members) can extend between the two lower (as viewed in the orientation of FIG. 4C) retractor elements 453, 454 independent of bridge member 444. These elements 453, 454 can help open up the lower section of the retractor system, and the bridge member(s), whether independent or connected to bridge 444, can help to stabilize these elements, e.g., limit side to side movement. Such bridge members on the lower retractor elements can be used with the other retractor embodiments disclosed herein.

In some embodiments, each of the systems taught herein can have an outer tube that is wire-reinforced, such as mesh, braided, or the like, to provide kink resistance and torque-ability to the system, as well as to further facilitate a positioning of the system in the subject.

Figure 4E:
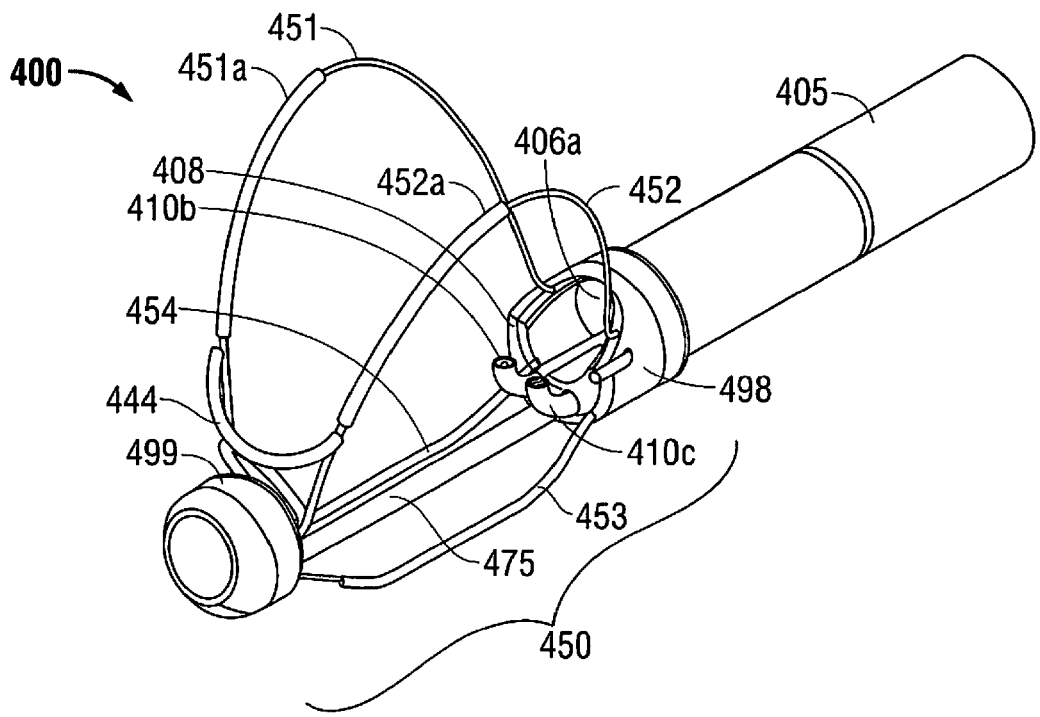

FIGS. 4D and 4E illustrate oblique views of the system 400 in collapsed and expanded configurations. The multi-lumen concept is presented with clarity in these figures, showing multiple lumens 406a, 406b, 406c in the catheter 405 in system 400. Lumen 406a can contain an endoscope (not shown) such as endoscope 315 described above, lumen 406b can contain a first working channel 410b for a first endoscopic tool (not shown), and lumen 406c can contain a second working channel 410c for a second endoscopic tool (not shown). The lumens 406b, 406c can receive the first and second tools directly therein, or alternatively, receive tool channels (flexible guides) 410b, 410c like tool channels 310 described above for angling the endoscopic tools slidably positioned therein. FIG. 4D illustrates the system in the collapsed configuration and FIG. 4E illustrates the system in the expanded configuration. In FIG. 4E, the tool channels {flexible guides) 410b and 410c are shown exposed from the catheter 405 so their distal ends are in a curved position. The tool channels can be further advanced axially to align the curved distal ends with the target tissue.

The system 400 also includes retractor elements 451,452, 453 and 454. The retractor system further includes a flexible tube or beam 470 in the collapsed configuration, whereas in the expanded configuration, the retractor system has a rigid beam 475 that was formed from the flexible beam 470. A rigid beam can be formed from a flexible beam, in some embodiments, by slidably inserting a rigid rod into a flexible tube that composes the flexible beam. More specifically, in this embodiment, the flexible beam 470 slidably receives thereover a stabilizing or rigidifying structure such as a rigid rod. The rigidifying (stabilizing) structure can be independently actuated by the user by actuating a control, such as a slidable lever, operably connected to the rigidifying structure, such that movement of the actuator distally advances the rigidifying structure over the flexible beam 470 to thereby stiffen the beam. Alternatively, the flexible beam 470 can have a lumen to slidably receive therein a rigidifying structure such as a rigid rod. The structure in either version can optionally be retracted from the flexible beam 470 to return the system back to the original more flexible state to aid collapsing of the retractor system. The beam 470 can be substantially circular in cross-section, although other cross-sectional shapes are also contemplated. As in the aforedescribed embodiments, the rigid beam limits deflection of the distal end of the catheter which could otherwise occur by pressure exerted on the distal end by the body lumen wall.

In many embodiments, the term "tool channel" can be used interchangeably with the term "working channel "or tool guide." And, in some embodiments, a channel can be a separate component placed inside the outer tube, or it can be a space remaining in the lumen of the outer tube between separate components that were placed in the outer tube, the separate components including, for example, an endoscope, a working channel, an instrument, a guide, and the like.

In some embodiments, as shown for example in FIGS. 4A-4E, the system can comprise a stable, yet dynamic operative environment in that it can include a reversibly-expandable retractor 450 that expands to form a treatment space 460 in the subject. The retractor 450 can be configured, for example, for the expansion to occur distal to the distal end 408 of the outer tube 405. In some embodiments, the retractor can at least substantially render the target tissue 490 aperistaltic for the treatment. The retractor 450 can have a variety of configurations to serve, for example, as a scaffolding within the gastrointestinal tract 495. For example, the retractor 450 can include retractor elements 451,452,453,454, along with a proximal coupler 498 operably connected to the retractor elements 451,452,453,454, whether at least substantially attached and/or at least slidably-engaged to the retractor elements 451,452,453,454, and a distal nexus or coupler 499 for a distal point of an operable connection with the retractor elements 451,452,453,454. Relative movement of the couplers 498, 499 can expand the retractor elements as described above. Alternatively, as described above, the retractor elements can be operably attached to a proximal actuator which moves the proximal portions relative to the fixed distal portions to bow the retractor elements outwardly, which in preferred embodiments can be made of superelastic material (although other materials are contemplated), or shape memorized retractor elements can be utilized.

The retractor elements 451 and 452 can have a covering 451a, 452a, respectively, which add bulk to the retractor elements 451, 452 by increasing its cross-sectional diameter. This is described in more detail below in conjunction with the embodiment of FIGS. 6A-6D.

Moreover, the retractor 450 can be a reversibly-stabilized and reversibly-expandable retractor, the retractor 450 forming an asymmetrical treatment space upon the expansion. And, the retractor 450 can be configured to reversibly stiffen an otherwise flexible arrangement of the retractor 450, the arrangement designed to facilitate ease of positioning of the system 400 in the subject and to reversibly stiffen for the expansion of the retractor 450. The stabilization of the retractor 450 can, in some embodiments, include stabilizing the retractor 450 through a stabilizer subsystem as taught herein, the stabilizer having, for example, an at least substantially-rigid beam 475 to support the expanded retractor 450.

Figure 5A:
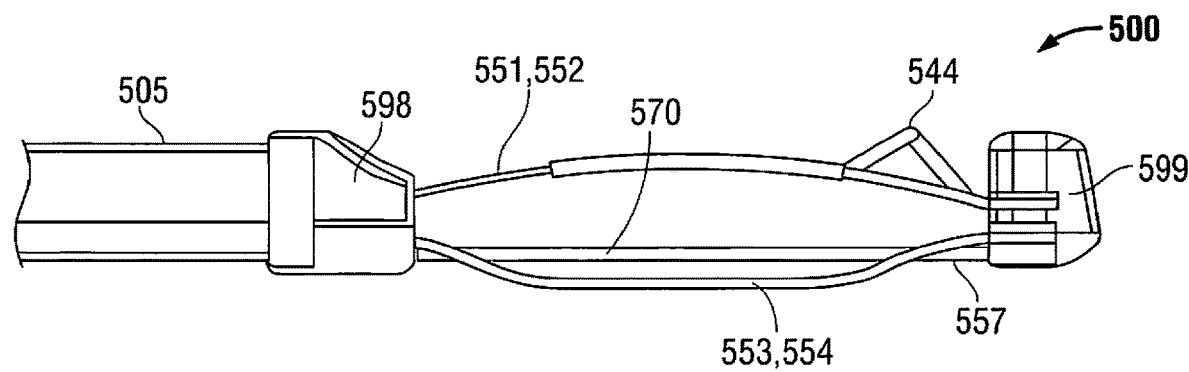
Figure 5B:
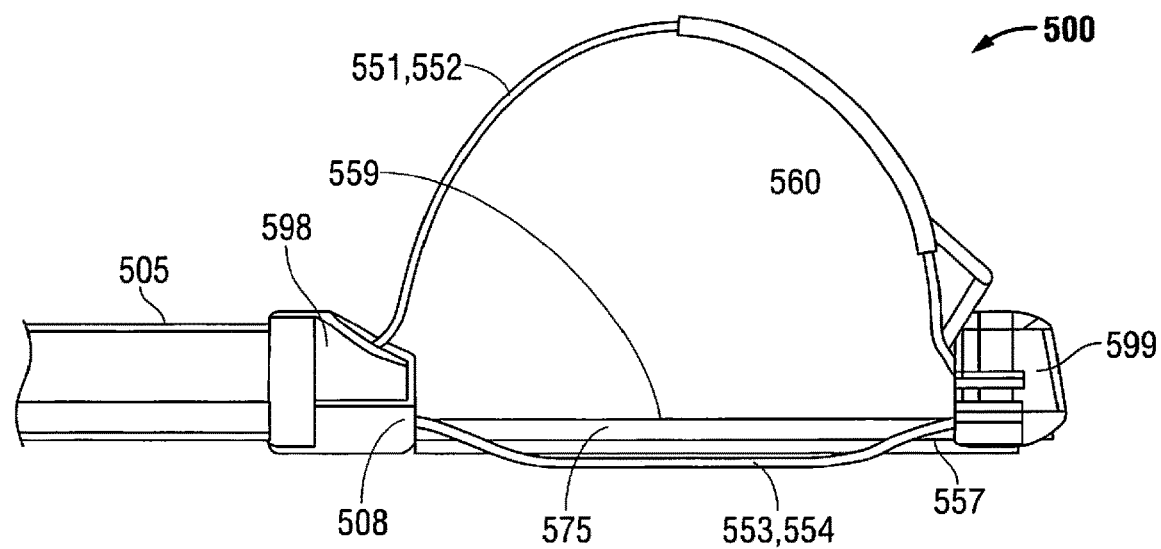
Figure 5C:
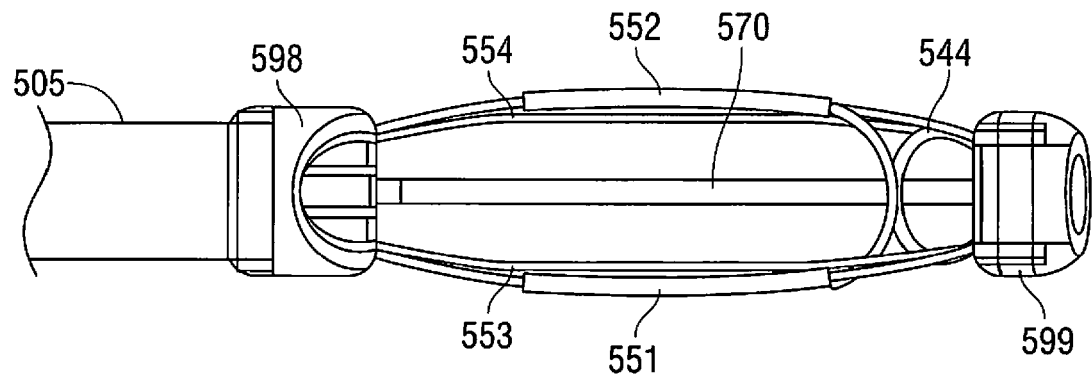
Figure 5D:
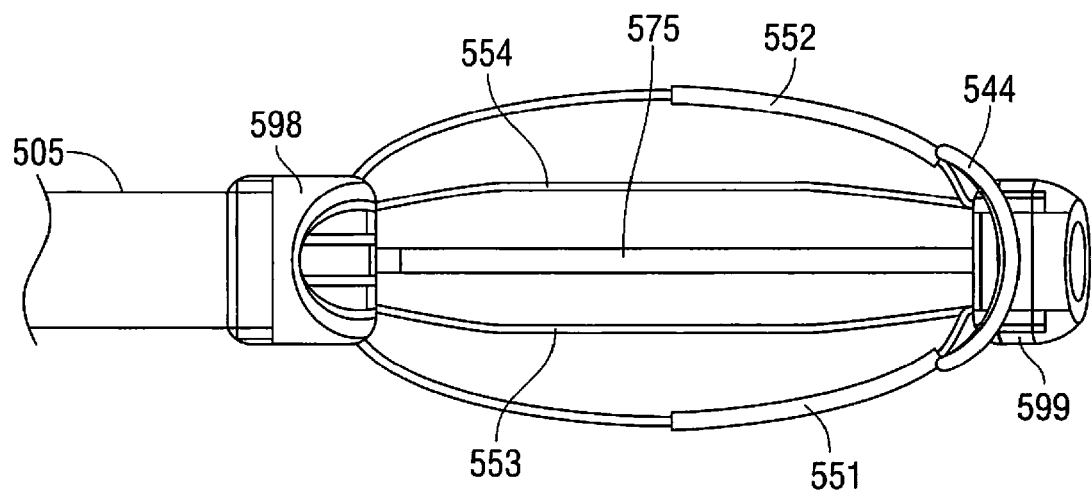

FIGS. 5A-5D illustrate side and top views of a system as taught herein, having side views and top views of expanded and collapsed configurations, according to some embodiments. The tool channels and tools are omitted for clarity, being similar to those described herein. FIGS. 5A and 5B illustrates side views of system 500 in collapsed and expanded configurations showing an example of an asymmetric work space that can be formed during an endoscopic procedure using the system 500. And, as shown in FIG. 5B, as with the previously described embodiments, the expansion can occur in a disproportionally greater amount on the luminal side 559 of the rigid beam 575 than the abluminal side 557 of the rigid beam 575 to increase the treatment, or working space 560, the treatment space 560 having a volume that is asymmetrically distributed around the rigid beam 575. In some embodiments, the expansion of the various retractors systems disclosed herein can occur in an amount that is at least 5× greater on the luminal side 559 of the rigid beam 575 than the abluminal side 557 of the rigid beam 575. And in some embodiments, the expansion can be at least 1.1× greater, at least 1.3× greater, at least 1.5× greater, at least 2.0× greater, at least 2.5× greater, at least 3.0× greater, at least 3.5× greater, at least 4.0× greater, at least 4.5× greater, at least 5.0× greater, at least 5.5× greater, at least 6.0× greater, at least 6.5× greater, at least 7.0× greater, at least 7.5× greater, at least 8.0× greater, at least 8.5× greater, at least 9.0× greater, at least 9.5× greater, at least 10.0× greater, or any 0.1× increment within this range, on the luminal side of the beam than the abluminal side of the beam.

In some embodiments, as shown for example in FIGS. 5A-5D, the system can comprise a stable, yet dynamic operative environment in that it can include a reversibly-expandable retractor 550 that expands to form a treatment space 560 in the subject. The retractor 550 can be configured, for example, for the expansion to occur distal to the distal end 508 of the outer tube 505. In some embodiments, the retractor can at least substantially render the target tissue 590 aperistaltic for the treatment. The retractor 550 can have a variety of configurations to serve, for example, as a scaffolding within the gastrointestinal tract 595. For example, the retractor 550 can include retractor elements 551,552,553,554, along with a proximal coupler 598 operably connected to the retractor elements 551,552,553,554, whether at least substantially attached and/or at least slidably-engaged to the retractor elements 551,552,553,554, and a distal nexus or coupler 599 for a distal point of an operable connection with the retractor elements 551,552,553,554. The couplers 588, 599 can be relatively movable to expand the retractor elements 551, 552 (and optionally elements 553, 554 in the embodiments where they are expandable) in the same manner as the couplers described above, e.g., couplers 198, 199. The retractor elements can alternatively be fixedly attached at their distal ends, e.g., to distal coupler 599, and operatively connected at proximal ends to an actuator or made of self-expanding material such as shape memory material as in the various embodiments described herein. Each retractor element 551, 552 in the embodiment of FIG. 5B expands to a substantially uniform (symmetric) arcuate shape, although alternatively they each can be configured to expand to a non-uniform (non-symmetric) shape as in the embodiments described above. Note that in this embodiment where the retractor elements 551, 552 individually expand to a substantially symmetric shape, there expansion is on one side of the multi lumen outer tube 505, i.e., to only one side of a longitudinal plane through which a longitudinal axis passes. Therefore, their expansion with respect to the retractor system is asymmetric while their individual expanded shape might be symmetric. Retractor elements 553, 554 have a slightly bowed configuration similar to retractor elements 353, 354. Retractor elements 553, 554, positioned as the lower elements of the cage as viewed in the orientation of FIG. 5A, can have limited expansion or can be provided so they do not expand when the retractor system expands but instead remain substantially in the same position. In such embodiments, the expanding retractor elements 551, 552 can be operably connected to an actuator and the lower elements 553, 554 can be fixedly (non-movably) attached to the catheter, e.g., to fixed proximal and distal couplers. Such attachment alternative is also applicable to the other embodiments disclosed herein wherein it is disclosed that the lower retractor elements maintain substantially the same position in the collapsed and expanded positions of the retractor system.

Moreover, as with the retractors described hereinabove, the retractor 550 can be a reversibly-stabilized and reversibly-expandable retractor, the retractor 550 forming an asymmetrical treatment space 560 upon the expansion. And, the retractor 550 can be configured to reversibly stiffen an otherwise flexible arrangement of the retractor 550, the arrangement designed to facilitate ease of positioning of the system 500 in the subject and to reversibly stiffen for the expansion of the retractor 550. The stabilization of the retractor 550 can, in some embodiments, include stabilizing the retractor 550 through a stabilizer subsystem as taught herein, the stabilizer having, for example, an at least substantially-rigid beam 575 to support the expanded retractor 550. In the embodiment of FIGS. 5A-5D, the rigid beam 575 can be provided in a permanently stiffened condition as beam 175 of FIG. 1, or alternatively can be formed by advancement of a rigidifying (stabilizing) structure over a flexible element or into the lumen of the flexible tubular member by an actuator as described above. In either case, the beam rigidifies the retractor system in the asymmetrical configuration creating the stable asymmetrical working space to facilitate access and manipulation of the target tissue.

FIGS. 6A-6D illustrate side views of a system as taught herein having side views and cross-sections of expanded and collapsed configurations of the system, according to some embodiments.

Figure 6A:
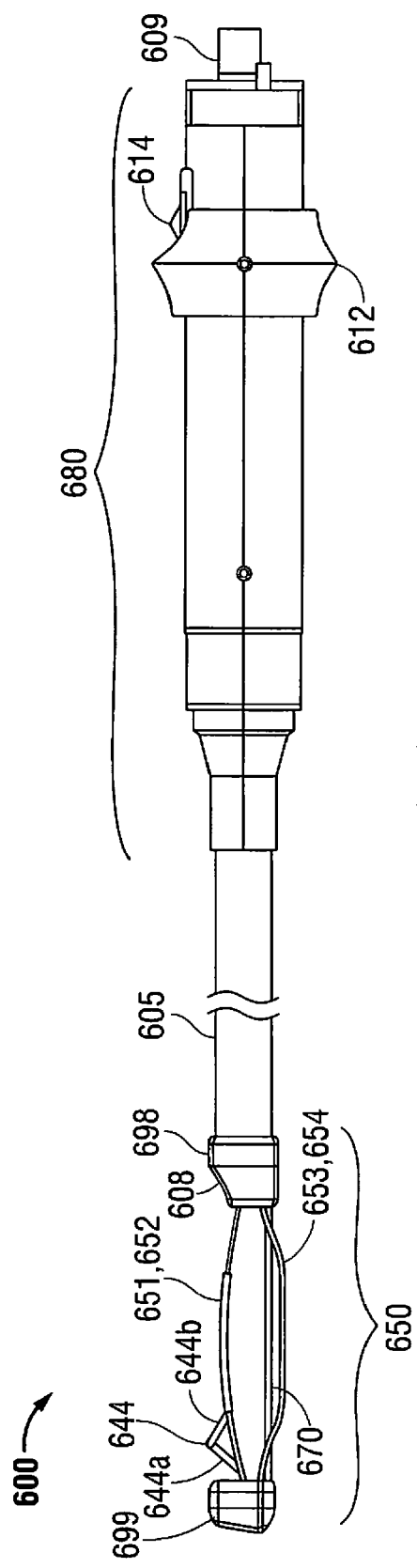
Figure 6B:
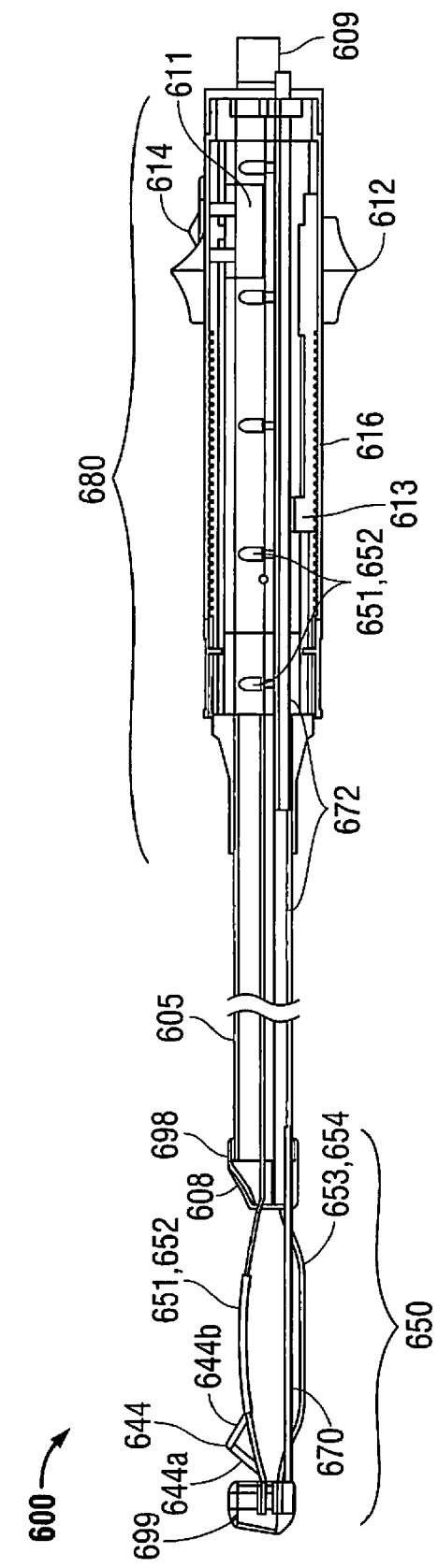

The figures illustrate an example of a multi-lumen catheter system having a reversibly-stabilized and reversibly-expandable retractor for a minimally invasive treatment of a subject. FIGS. 6A and 6B illustrate a side view that shows that the system 600 can include a flexible outer tube 605 for guiding one or more tool channels (not shown) similar to the tool channels described above and an endoscope (not shown) similar to the endoscope described above within the system 600. The flexible outer tube 605 has a lumen, a proximal end extending into the handle 680, and a distal end 608. Each tool channel (serves as a guide through which a tool (not shown) can be manipulated in a treatment of a target tissue in a subject. That is, the tool channels are configured to receive and reorient the tools inserted therethrough as in the embodiments described above. In some embodiments, the retractor 650 can be a reversibly-stabilized and reversibly-expandable retractor 650 forming a treatment space 660 upon expansion and configured for the expansion to occur distal to the distal end 608 of the outer tube 605. The retractor 650 can be designed to reversibly-stiffen an otherwise flexible arrangement of the retractor 650, the flexible arrangement designed to facilitate the positioning of the system in the subject and to reversibly-stiffen for the expansion of the retractor 650. In these embodiments, the reversibly-stiffened arrangement of the retractor 650 can form an at least substantially-rigid beam 675 from an otherwise flexible beam 670 as a structural support for the expansion of the retractor 650.

Handle 680 at the proximal end includes entry ports for operatively combining the system with external components, such as an entry port 609 for an endoscope (not shown) and/or a tool (not shown). The handle 680 is also operatively connected to the proximal end of the outer tube 605 and can have exit ports from the handle 680 into the outer tube 605. The system can include a stabilizer subsystem, in some embodiments. For example, a stabilizer actuator 612 can be included on the handle 680 to reversibly-stiffen the flexible beam 670 to create the at least substantially-rigid beam 675 for the expansion of the retractor 650. A retractor actuator 614 can be included on the handle 680 to reversibly expand the retractor 650. The retractor 650 is shown in FIGS. 6A and 6B in the collapsed (non-expanded) condition.

FIGS. 6C and 6D illustrate oblique views of the system 600 in expanded configurations. The expanded configurations have a rigid beam 675 that was formed from the flexible beam that is typically present in the collapsed state for positioning in the subject. The rigid beam 675 can be formed from a flexible beam, in some embodiments, by slidably inserting a rigid member (e.g., a rod) either over or alternatively into a flexible member that composes the flexible beam to transform the flexible beam into a stiffer, more rigid beam. As shown in FIGS. 6B and 6D, the stabilizer actuator 612 is operably connected to the rigid member (stabilizing structure) such as rigid rod 672 through a rod coupler 613. Consequently, movement of the actuator 612 in a first direction, e.g., a distal direction from a proximal position, will cause the stabilizing structure 672 to advance over the flexible beam 670 to rigidify it (forming beam 675) to stabilize the retractor system, and movement of the actuator 612 in a reverse, e.g., a proximal direction back to its proximal position, will retract the stabilizing structure 672 from the flexible beam 670 to return the flexible beam 670 to its more flexible condition.

The retractor actuator 614 is operably connected to retractor elements 651, 652 through an element coupler 611. The stabilizer actuator 612 and/or the retractor actuator 614 can be reversibly engageable with the handle 680, in some embodiments, such that the stabilizer actuator 612 and/or the retractor actuator 614 can be reversibly-fixed in position relative to the handle 680. In some embodiments, the stabilizer actuator 612 and/or the retractor actuator 614 can be multi-positional, having at least three positions for expansion and/or collapse of the retractor. In some embodiments, the stabilizer actuator 612 and/or the retractor actuator 614 can have a plurality of ratchet teeth 616 to provide a plurality of positions for reversibly-fixing the stabilizer and/or for reversibly fixing the retractor in position during expansion or collapse of the retractor. As shown in FIG. 68, in the proximal position of the retractor actuator 614, coupler 611 is in the proximal position and the retractor elements are in the non-expanded position. To expand the retractor elements, retractor actuator 614 is slid distally to move the attached coupler 611 distally, as shown in FIG. 6D, thereby causing the attached elements 651, 652 to bend outwardly due to their fixed connection at their distal end to the distal coupler 699.

One of skill will appreciate that the handle can be any of a variety of shapes to provide a desired or ergonomic position for operation of the system. By way of example, the retractor actuator can be configured as a finger-activated button on the handle 680 that slides back and forth through a slot in the handle 680 to expand or collapse the retractor elements. A means for dynamically adjusting or ratcheting the retractor position can be provided along the handle slot to lock the position of the retractor elements in place when the retractor actuator button is not pressed. A button on the opposite side of the handle can be operatively connected to the stabilizer subsystem to convert the flexible beam into a rigid beam, or convert the rigid beam into a flexible beam. The handle can have inner channels routed axially, for example, within the body of the handle and in communication with ports for tools and endoscope introduction into the outer tube. In some embodiments, the handle can be configured to require that the stabilizer actuator is activated before the retractor actuator can be activated, serving as a "safety" mechanism in the operation of the system.

As such, in some embodiments, as shown for example in FIGS. 6A-6D, the system can comprise a stable, yet dynamic operative environment in that it can include a reversibly-expandable retractor 650 that expands to form a treatment space or working chamber 660 in the subject. The retractor 650 can be configured, for example, for the expansion to occur distal to the distal end 608 of the outer tube 605. In some embodiments, the retractor can at least substantially render the target tissue 690 aperistaltic for the treatment. The retractor 650 can have a variety of configurations to serve, for example, as a scaffolding within the gastrointestinal tract 695. For example, the retractor 650 can include retractor elements 651, 652, 653, 654, along with a proximal coupler 698 operably connected to the retractor elements 651,652, 653,654, whether at least substantially attached and/or at least slidably-engaged to the retractor elements 651,652, 653,654, and a distal nexus or coupler 699 for a distal point of an operable connection with the retractor elements 651, 652,653,654. More specifically, the distal end of the retractor elements 651, 652 are attached within slots or openings in the proximal end of the distal coupler 699. The proximal ends of the retractor elements 651, 652 extend proximally through lumens in the catheter to attach to movable coupler 611. In this manner, with the distal ends of the retractor elements 651, 652 fixed, distal movement of the coupler 611 forces retractor elements to bow outwardly as shown. Retractor elements 653, 654 can be attached to the distal coupler 699 and in some embodiments attached to movable coupler 611 if some expansion of these retractor elements 653, 654 is desired, or alternatively, fixedly attached to the catheter if expansion is not desired and expansion is limited to the retractor elements 651, 652.

It should be appreciated, that such couplers for retraction element expansion disclosed in FIGS. 6A-6D can be utilized with the other embodiments of the retractor systems disclosed herein. Additionally, it should be appreciated that alternative ways to expand the retractor elements can be utilized, including for example providing relatively movable couplers 698, 699 to expand the retractor elements 651, 652, (and optionally 653, 654) in the same manner as the couplers described above, e.g., couplers 198, 199. The retractor elements can also alternatively be made of self-expanding material such as shape memory material.

Each of the retractor elements 651, 652 in the embodiment of FIGS. 6A-6D expand to a substantially symmetric arcuate shape, although alternatively they can be configured to expand to an asymmetric shape as in the embodiments described above. Note that in in this embodiment where the retractor elements 651, 652 expand to a substantially symmetric shape, their expansion is on one side of a longitudinal axis of the multi lumen tube outer tube (catheter) 605. Therefore, the expansion of the retractor system is asymmetric while their individual expanded shape is substantially symmetric. Retractor elements 653, 654 can optionally expand slightly outwardly in a bowed configuration. The retractor element 651 can have a covering thereon. Similarly, retractor element 652 can have a covering thereon. The covering extends over an intermediate portion of the elements 651, 652 and can be in the form of a heat shrink tubing. The covering helps control expansion by providing a less flexible region. This covering is similar to covering 451a and 452a of the embodiment of FIGS. 4D, 4E.

As described herein, the retractor 650 can be a reversibly-stabilized and reversibly-expandable retractor, the retractor 650 forming an asymmetrical treatment space 660 upon the expansion. And, the retractor 650 can be configured to reversibly stiffen an otherwise flexible arrangement of the retractor 650, the arrangement designed to facilitate ease of positioning of the system 600 in the subject and to reversibly stiffen for the expansion of the retractor 650. The stabilization of the retractor 650 can, in some embodiments, include a means for stabilizing the retractor 650 through a stabilizer subsystem as taught herein, the stabilizer having, for example, an at least substantially-rigid beam 675 to support the expanded retractor 650.

The rigid rod can be a straight component comprising a rigid material, for example stainless steel or another metal or alloy, that is slidable in and out of the inner diameter (lumen) of the flexible tube. As such, the stabilizer subsystem can have a flexible beam or rigid beam by sliding the rigid rod proximal (i.e., anally) to the flexible tube by pulling back on the rigid rod through a mechanism operably connected to the handle. The rigid rod can be pushed forward (i.e., orally) into the flexible tube to stiffen and straighten the flexible tube as in the embodiments described above. By pushing the rigid rod across the length of the flexible tube, the flexible tube, or flexible beam, becomes rigid and straight, and in effect renders the whole retractor structure at least substantially rigid and straight to stabilize the retractor system. One of skill in the art will appreciate that any mechanism of reversibly stiffening a flexible component in vivo may be used in some embodiments. For example, the flexible tube, or flexible beam, may also comprise a series of rigid tubes having a flexible, non-stretchable cable passing through the lumens of the tubes. When the cable is relaxed, the series of rigid tubes can be separated using, for example, a compressible component such as a spring between each of the series of rigid tubes to provide a flexible non-overlapping configuration. When the cable is tensioned, the compressible components compress, and the rigid tubes overlap, converting the flexible beam into a rigid beam. Such alternative mechanisms can be utilized with any of the embodiments described herein.

The reversibly-stabilized retractor, as described herein, is useful in positioning the working space at the site of treatment of the target tissue as it can be rendered flexible for positioning and later rendered rigid for expansion of the retractor. During introduction of a system taught herein into a tortuous body lumen, for example a colon, the retractor can be unexpanded and flexible. This flexibility allows the retractor to bend to conform to the bends in the tortuous body lumen, so that it can be advanced with ease and not cause trauma to the lumen. The rings which hold the retractor elements together can also have lumens that allow passage of a guide such as an endoscope. In such embodiments, when the retractor is in the flexible mode for introduction, for example, the rings can be free to slide over the guide as the system is advanced forward. In some embodiments, the lumens of the rings can be large enough relative to the diameter of the guide to allow for tilting and translation of the system on the guide, helping the system conform to the bends of the guide during advancement of the system orally or anally. Once the retractor is advanced to the target location in the lumen, the flexible beam of the retractor can be straightened and stiffened as described herein. Since the system can be flexible and torsion ally stiff, the proximal shaft or the handle can be easily rotated as desired relative to the location of the target lesion.

The retractor elements can have at least one pair that is pre-shaped having peaks pointing outwards at a desired angle. In some embodiments, the angle can range from about 45 degrees to about 135 degrees, about 60 degrees to about 120 degrees from each other on one side of the rigid beam, the vertex of the angle being the central axis of the rigid beam, as can be seen in the figures provided herein. In some embodiments, the angle is about 90 degrees between retractor elements. Upon expansion, the retractor elements bulge outwards on one side disproportionally more than the other retractor elements, resulting in an asymmetrical expansion of the retractor. The at least substantially rigid beam prevents or inhibits deformation of the retractor during creation of forces on the retractor in the expansion and prevents or inhibits bending of the catheter tip. The forces include forces from expanding tissue outwards asymmetrically, as well as the initial forces applied on the retractor elements to create an asymmetrical working space.

In some embodiments, the target lesion can be located on the side of the most expanded retractor elements so to facilitate maximizing or increasing the distance between the lesion to be treated and the portals at which the endoscope and tools are introduced into the working space. The endoscope and tools can be maneuvered independently, for example, to access the lesion at a greater range of angles than is currently clinically obtainable using state-of-the-art systems. This increased maneuverability can improve the view of the lesion and ability to manipulate and dissect the lesion. For example, a grasper can be advanced out of the instrument channel into the working space and flexed towards the polyp, grasp the polyp and retract the tissue to expose the base of the polyp for dissection by a dissection tool through the multi-channel systems taught herein. Sometimes, it can also be desired to reduce the distance between the lesion to be treated and the portals at which the endoscope and tools are introduced into the working space. For example, it can be desired to locate the lesion on the side of the least expanded retractor elements to better align the lesion with the endoscope channel substantially parallel to the lumen wall. Such a configuration may be clinically optimal while the polyp is retracted by a grasper towards the most expanded side. In such embodiments, a dissection tool can be advanced through a channel at the base of the polyp and dissect the polyp's base where it attaches to the lumen wall, while the position of the endoscope provides a close view of the base of the polyp to help identify the desired margin for dissection.

Any of the systems taught herein can include a bridge member, which provides structural support to add stability to the retractor. The bridge member can include any configuration conceivable by one of skill to provide additional support, such as a scaffolding for enhancing or buttressing the stability and rigidity of the expanded contractor. For example, bridge member 644 is configured to maintain a desired orientation of the retractor elements 651,652,653, 654 during the expansion, the bridge member 644 operably stabilizing at least two 651,652 of the four retractor elements 651,652,653,654. As shown, the bridge member outer portion in the collapsed position of the retractor 650 extends radially outwardly and in the expanded position extends more distally (see. FIG. 6D). Although only one bridge member 644 is shown, it is also contemplated that more than one bridge member could be provided to connect retractor elements 651, 652. Additionally, one or more bridge members can be provided to connect retractor elements 653, 654 to stabilize and limit side to side movement of these elements as well. Moreover, in some embodiments, each of the systems taught herein can have an outer tube, for example outer tube 605, that is wire-reinforced, such as mesh, braided, or the like, to provide kink resistance and torque ability to the system, as well as to further facilitate a positioning of the system in the subject. In some embodiments, the bridge member 644 can be configured to reduce drag from surrounding tissue during use. For example, as shown in FIGS. 6A and 6B, the bridge member 644 can be configured to facilitate a movement of the system in a gastrointestinal tract by designing the bridge member 644 to include a forward component 644a that is inclined to facilitate forward movement orally, and a reverse component 644b that is inclined to facilitate reverse movement anally.

The bridge member can be connected to the retractor elements, for example, to maintain a desired orientation of the retractor elements as they expand against a gastrointestinal tissue, for example. As the retractor is expanded, the bridge member is also expanded outward. In some embodiments, the bridge member is operably connected only to the retractor elements that expand the most, for example the retractor elements 651,652 in FIG. 6, which can be the members that incur the most induced forces on the retractor due to the disproportionate pressure applied to create the asymmetrical working space in the expansion. In some embodiments, the bridge can be designed to flex to prevent the retractor elements from collapsing towards each other or bending away from each other, while also providing some spring or elasticity to the system to comply gently with the tissue. One of skill will appreciate that the bridge member can comprise any suitable material that provides the material characteristics desired. For example, the bridge can be formed from a curved nitinol wire in some embodiments. The ends of the nitinol wires can be connected to the retractor elements using any manufacturing process deemed suitable by one of skill for the in vivo uses taught herein, such process including, for example, tubing connectors, adhesives, or solder.

Figure 7:
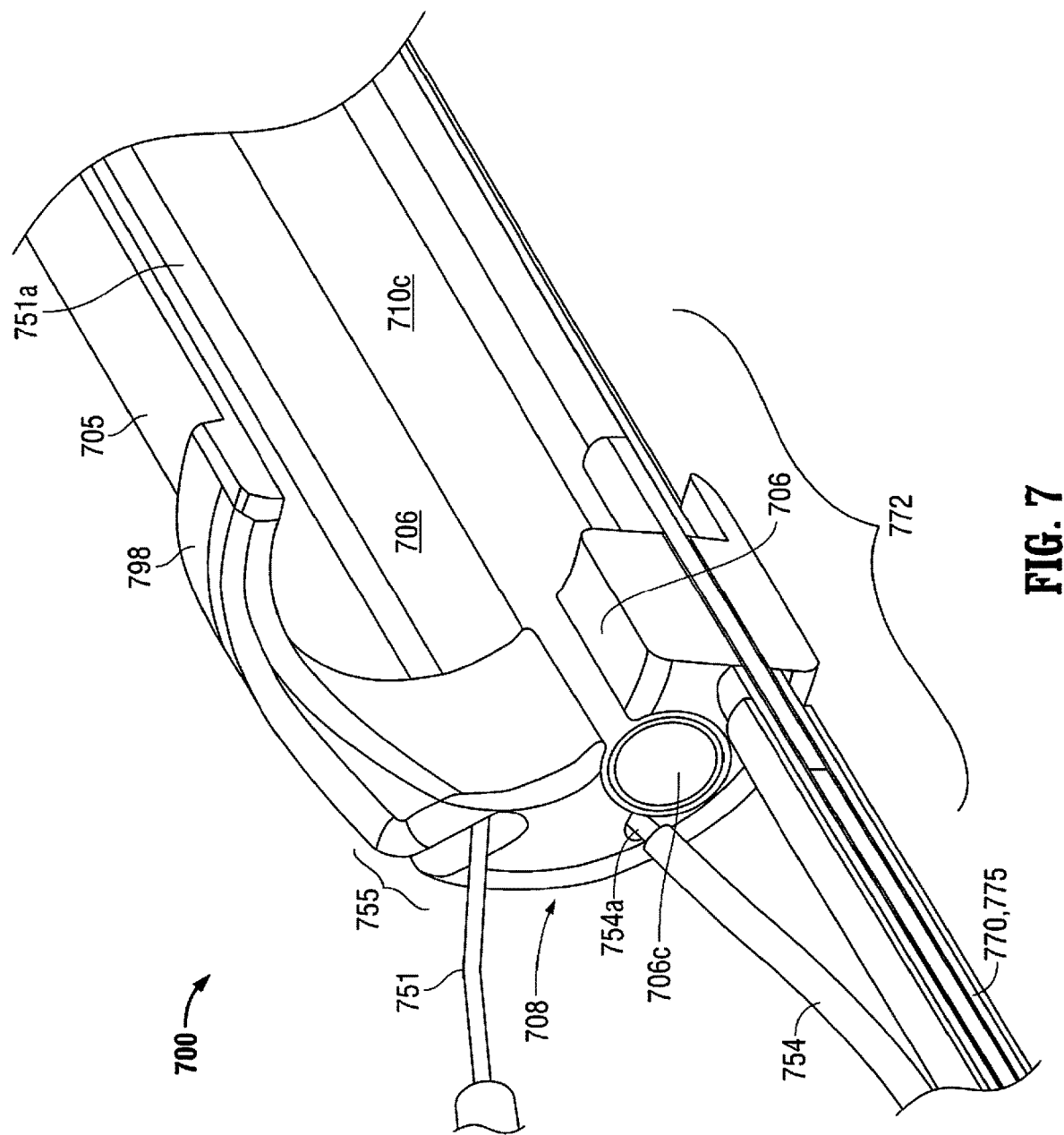
FIG. 7 illustrates a cutaway view of the distal end of the outer tube of a system as taught herein, showing components of the expansion and collapse of the retractor, according to some embodiments.

FIG. 7 illustrates a cutaway view of the distal end of the outer tube of a system 700 as taught herein, showing components of the expansion and collapse of the retractor, according to some embodiments. The figure illustrates the distal end 708 of outer tube 705. The distal end 708 includes a slot guide 755 to control the orientation of an expanding retractor element 751, as well as a port 754a for operably receiving/supporting a lower retractor element 754. Another slot guide {not shown) can be provided to control the orientation of another retractor element. A lumen 706c can be provided to contain a working channel 710c for insertion of a tool channel as described above for insertion of working instruments or alternatively for direct insertion of working instruments without a tool channel. The lumen 706 of the outer tube 705 can also be used to guide an endoscope {not shown) through an exit port in distal end 708. Only a portion of retractor components 751, 754, 770, is shown to partially describe the relation between the outer tube 705 and the retractor in some embodiments. The retractor can be configured, for example, for the expansion to occur distal to the distal end 708 of the outer tube 705. For example, the retractor can include four retractor elements as in the embodiments described above, with retractor elements 751 and 754 shown and the two other retractor elements not shown because of the cutaway view. A proximal coupler 798 is operably connected to the four retractor elements, whether at least substantially attached and/or at least slidably-engaged to the retractor elements. The retractor can be configured to reversibly stiffen an otherwise flexible arrangement of the retractor, the arrangement designed to facilitate ease of positioning of the system 700 in a subject and to reversibly stiffen for the expansion of the retractor in the subject. The stabilization of the retractor can, in some embodiments, include stabilizing the retractor through a stabilizer subsystem as taught herein, the stabilizer having, for example, a flexible beam 770 that can be converted to an at least substantially-rigid beam 775, by slidably engaging a rigid, or substantially rigid, component 772 as taught herein in operable connection with the flexible beam 770, to support the expanded retractor. The flexible bean 770 can be stiffened in the manners described herein with respect to the flexible beams of the other embodiments.

Figure 8:
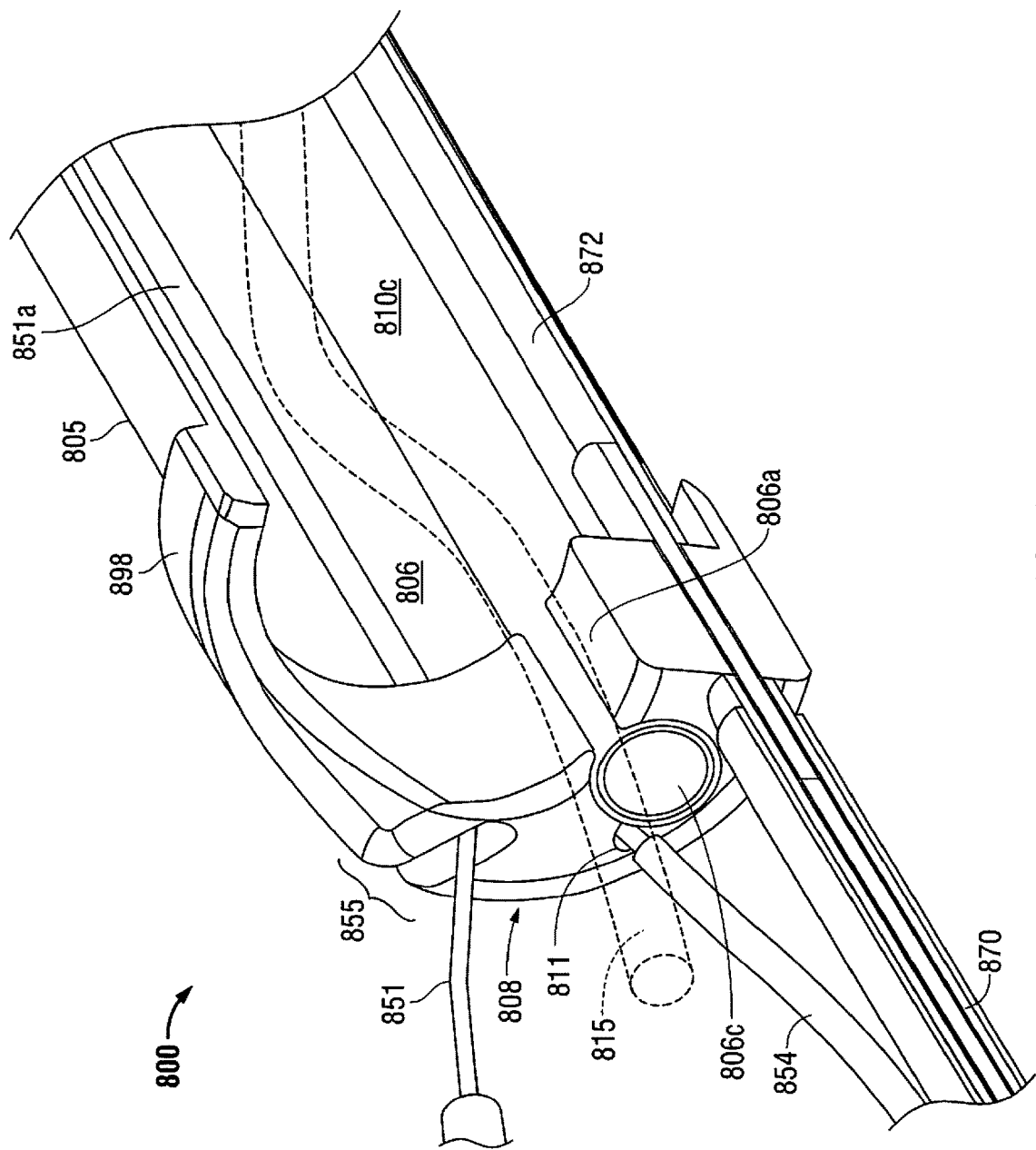
FIG. 8 illustrates the cutaway view of FIG. 7, showing the distal end of the outer tube of a system as taught herein, in which components of the system can be floating in the outer tube to enhance flexibility for positioning the system in a subject, according to some embodiments.

FIG. 8 illustrates a cutaway view similar to FIG. 7, except in this embodiment, a floating channel system is provided. That is, FIG. 8 shows the distal end of the outer tube of a system as taught herein, in which components of the system can be floating in the outer tube to enhance flexibility for positioning the system in a subject, according to some embodiments. The figure illustrates the distal end 808 of outer tube 805. The distal end 808 includes a slot guide 855 to control the orientation of an expanding retractor element 851 and an opening 811 for lower retractor element 854. A second slot guide and a second opening (not shown) are provided to receive respectively another upper and lower retractor element. A lumen 806c can be provided to contain a working channel 810c which receives a tool channel to guide a working instrument or alternatively directly receives a working instrument. The lumen 806 of the outer tube 805 is used to guide an endoscope 815. Only a portion of the retractor components 851, 854 are shown to partially describe an embodiment of the relation between the outer tube 805 and the retractor. The retractor can be configured, for example, for the expansion to occur distal to the distal end 808 of the outer tube 805. For example, the retractor can include four retractor elements in the same manner as described above, only two of which are shown (elements 851 and 854). A proximal coupler 898 is operably connected to the retractor elements, whether at least substantially attached and/or at least slidably-engaged to the retractor elements. The retractor can be configured to reversibly stiffen an otherwise flexible arrangement of the retractor, the arrangement designed to facilitate ease of positioning of the system 800 in a subject and to reversibly stiffen for the expansion of the retractor in the subject. The stabilization of the retractor can, in some embodiments, include stabilizing the retractor through a stabilizer subsystem as taught herein, the stabilizer having, for example, a flexible beam 870 that can be converted to an at least substantially-rigid beam in any of the manners described herein with respect to the rigidifying of the flexible beam, e.g., slidably engaging a rigid, or substantially rigid, component 872 as taught herein in operable connection with the flexible beam 870, to support the expanded retractor. As in the other embodiments described herein, an actuator can be utilized which is operably coupled to the rigidifying structure to advance and retract it with respect to the flexible beam 870.

The retractor elements are movable between a collapsed insertion position and an expanded position to form an asymmetric working chamber as in the embodiments described above.

During a use of the system 800, the working channel 810c can be a floating channel that is (i) at least substantially attached to the lumen of the outer tube at a first proximal location (not shown) and a first distal location 806c and (ii) at least substantially floating in the lumen 806 of the outer tube 805 between the first proximal location {not shown) and the first distal location 806c. Likewise, during the use of the system 800, the endoscope 815 can be a floating endoscope 815 that is {iii) at least slidably-attached to the lumen 806 of the outer tube 805 at a second proximal location (not shown) and a second distal location 806a and (iv) at least substantially floating in the lumen 806 of the outer tube 805 between the second proximal location (not shown) and second distal location {806a). And, during the use of the system 800, the working channel 810c and the endoscope 815 also form separate floating components of a floating arrangement that (v) at least substantially increases the flexibility of the system 800 over a second such system having separate lumens for a tool and an endoscope, the separate lumens affixed to the lumen throughout the length of the outer tube between the proximal end and the distal end of the outer tube, the increased flexibility facilitating an ease of positioning the system 800 in the subject for the treatment of the target tissue. In some embodiments, the endoscope 815 can be at least slidably-attached to the distal end 808 of the outer tube 805 by inserting the endoscope 815 through a dedicated port (not shown) for the endoscope 815, such that the system 800 is configured to be substantially limited to a sliding movement in and out of the distal end 808 of the outer tube 805. And, in some embodiments, the endoscope 815 can be allowed to also float in a port 806a that is substantially larger than the endoscope 815, providing a sliding motion for the endoscope as well as room for side-to-side movements as well.

Figure 9A:
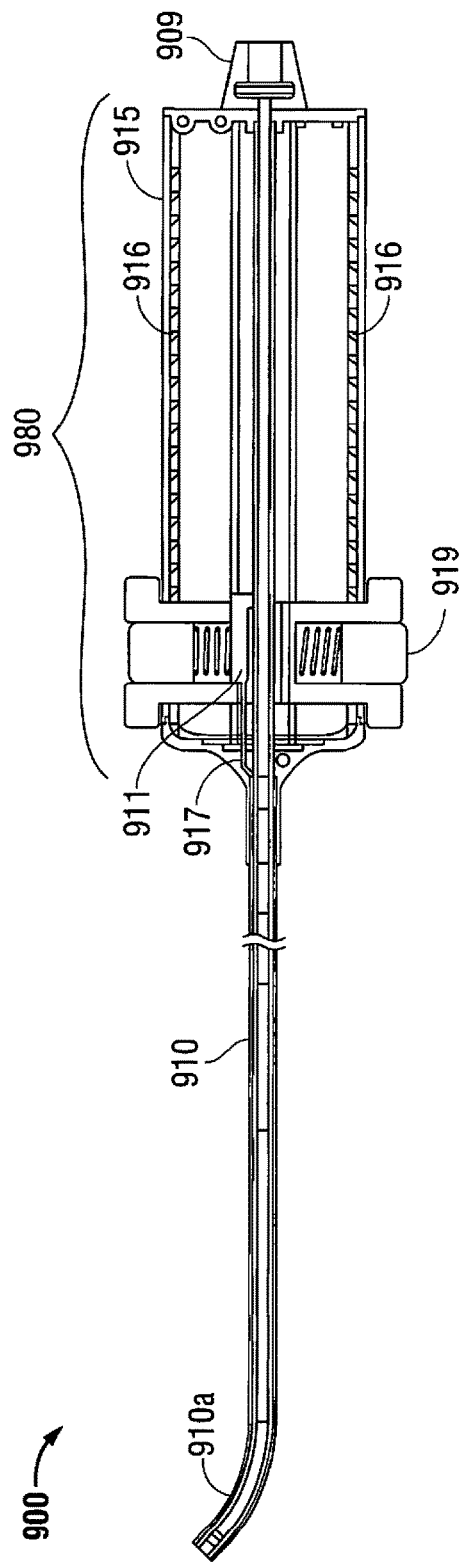
FIGS. 9A and 9B illustrate side views of working, and/or floating, channels that can be used to guide tools as taught herein, according to some embodiments.
Figure 9B:
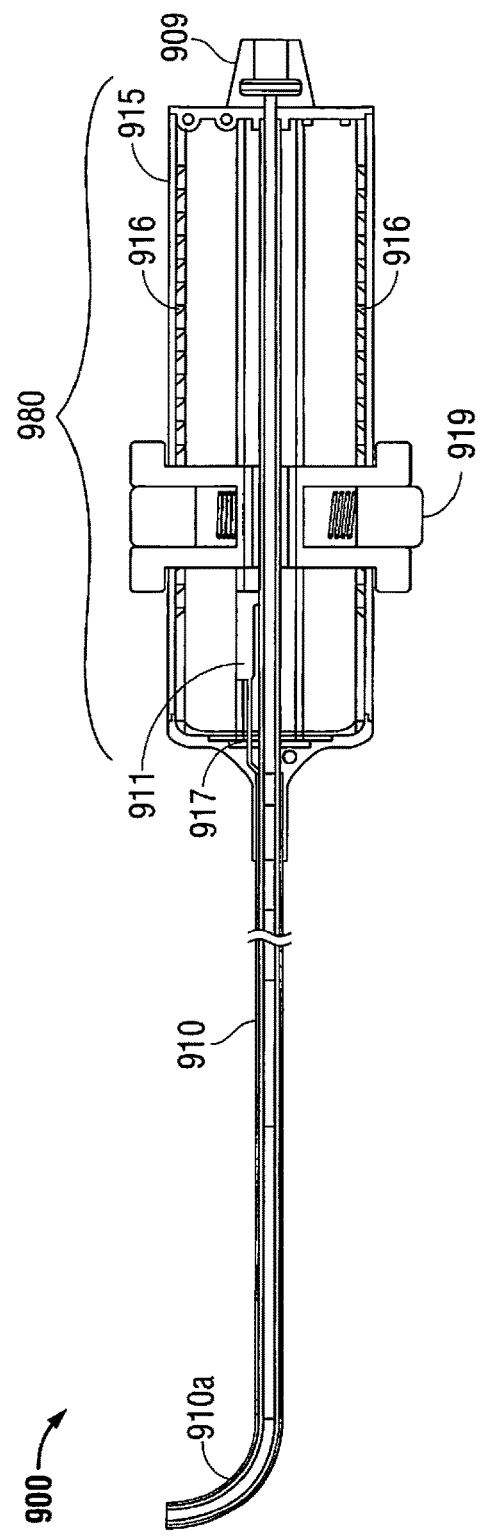

FIGS. 9A and 9B illustrate side views of working, and/or floating, channels that can be used to guide tools as taught herein, according to some embodiments. As discussed herein, the working channels can have at least a portion of which floats in the lumen of the outer tube in a manner that is the same or similar to FIG. 8 to further enhance the flexibility of the outer tube during position of the system in a subject. In some embodiments, the terms "channel," "floating channel", and "tool channel" can be used interchangeably. Each tool channel can be operatively connected to a handle 980 in a manner that is the same or similar to the operable connections taught herein for the retractor actuator and/or the stabilizer actuator. FIG. 9A shows the tip 910a of the tool channel 910 in a substantially extended position, whereas FIG. 9B shows the tip 910a of the tool channel 910 in a substantially bent position, such that the distal tip 910a is deflected substantially normal to the central axis of the tool channel 910. A system 900 consistent with other systems taught herein, for example, can include an entry port 909, a tool channel 91 inserted through entry port 909, a wire coupler 911, ratchet teeth 916, a pull wire 917 for flexing or extending the tip 910a of the working channel 910, and wire actuator 919. The ability to flex the tip 910a of the tool channel 910 facilitates independent positioning of a tool (not shown) in the treatment of a target tissue in a subject. In some embodiments, the wire actuator 919 can be multi-positional, having at least three positions for bending tip 910a of tool channel 910. In some embodiments, the wire actuator 919 can have tooth engageable with one of a plurality of ratchet teeth 916 in handle housing 915 to provide a plurality of positions for reversibly-fixing the bent tip 910*a* in position during use of the tool (not shown) in the treatment of the target tissue in the subject. More specifically, when the wire actuator 919 is moved from its distal position of FIG. 9A to a more proximal position, it pulls pull wire 917, which is attached to the tip 910*a* of tool channel 910, proximally to tension the tip 910*a*, causing it to bend to the configuration of FIG. 9B. Engagement of the tooth of actuator 919 with the teeth 916 maintains the position of actuator 919 and thus maintains the bent position of the tip 910*a*. Note although the tip is shown bent at substantially 90 degrees to the longitudinal axis of the tool channel 910, bending to other angles is also contemplated. Also, in some embodiments, actuator 919 is provided to control the angle of tip 910*a* by controlling the degree of proximal retraction of the pull wire 917, with further retraction further bending the tip 910*a* and less retraction bending the tip 910*a* to a lesser degree. More than one tool channel can be provided, and the multiple tool channels can be controlled by actuator 919, or alternatively, a separate actuator 919 can be provided for each tool channel. Also, various mechanisms can be utilized to lock the actuator(s) 919 in position to maintain the bent position of the tip of the tool channels.

Other mechanisms can also be utilized to control the tool channels. Alternatively, one or more of the tool channels can have a pre-bent {pre-curved} tip which is substantially straight when in the insertion position within the confines of the multi-lumen tube (catheter) and returns to the pre-bent position when exposed from the confines of the catheter.

As described herein, the channels can be configured to control the trajectory and position of instruments such as forceps in the working space created by the retractor. In some embodiments, a channel can be removed from, or inserted through, the outer tube of the system, alone or inside an additional channel that may be used as a guide. The channels can be virtually any size considered by one of skill to be useful in the systems described herein. For example, a channel can have an inner diameter ranging from about 1 mm to about 5 mm, from about 2 mm to about 4 mm, from about 1 mm to about 3 mm, or any range therein. The length of the channel should, of course, complement the length of the system. For example, the channel can have a length ranging from about 40" to about 72", from about 48" to about 60", from about 42" to about 70", from about 44" to about 68", or any range therein in increments of 1".

The channels can also comprise any material or configuration known to one of skill to be suitable for the uses described herein. For example, the channels can comprise a single polymer layer, multiple polymer layers, a wire reinforced layer, or a combination thereof. In some embodiments, a channel can comprise (i) an inner layer of a polymer such as, for example TEFLON or polyethylene for slippery luminal surface on the inner diameter of the channel; (ii) a metal such as, for example, a stainless steel, nitinol, or cobalt chromium as a wire reinforcement in the configuration of a braid, mesh, or helical coil layer covering the inner layer; and, (iii) an outer layer of a polymer such as, for example, PEBAX, polyurethane, polyethylene, silicone, PVC, or nylon.

In some embodiments, the channels can be configured such that the outer layer (iv) is the most rigid in the proximal section of the channel (i.e., the first about 12" to about 24" of the channel), having a hardness of about 60 Shore D to about 80 Shore D; (v) has a medium stiffness in the middle section (i.e., the next about 12" to about 36" of the channel), having a hardness of about 50 Shore D to about 72 Shore D; and, (vi) is the most flexible in the distal section (i.e., the next about 0.5" to about 2" of the channel), having a hardness of about 20 Shore D to about 50 Shore D). The distal section of the channel can be the section that flexes and can be the distal about 1" of the channel, in some embodiments. In some embodiments, the channels can have a rigid section just proximal to the distal section to keep this flexible section straight when there is a bending moment on the tip such as when the instrument which is inserted through the channel is grasping a tissue during a gastrointestinal treatment, for example. The length of the rigid section of the channels can range, for example, from about 1 cm to about 10 cm, from about 2 cm to about 8 cm, from about 3 cm to about 7 cm, from about 4 cm to about 6 cm, about 6 cm, or any range therein in 1 cm increments. The rigid section can include a rigid tube comprising a reinforcement material such as, for example, stainless steel or NITINOL, or a polymer such as PEEK or a polyimide embedded between the outer polymer layer and the inner polymer layer. The rigid section can have any suitable length to perform its function in the system. In some embodiments, the rigid section can have a length ranging from about 0.001" to about 0.005".

The thickness of the inner layer of the channels can range from about 0.0005" to about 0.005", from about 0.001" to about 0.004", from about 0.002" to about 0.003", about 0.001", or any range therein in 0.0005" increments. The thickness of the reinforcement layer can range from about 0.001" to about 0.006," from about 0.002" to about 0.005," from about 0.003" to about 0.005," from about 0.001" to about 0.003," about 0.002", or any range therein in increments of 0.0005". The thickness of the outer layer can range from about 0.003" to about 0.012", from about 0.004" to about 0.010," from about 0.005" to about 0.009," from about 0.005" to about 0.008," about 0.010", or any range therein in increments of 0.001".

For flexing the distal end of the channel, there can be a side lumen with a pull wire embedded between the inner layer and the outer layer. In some embodiments, the side lumen can be located between the inner layer and the reinforcement layer, or the side lumen can be a part of the inner layer. The side lumen can be made of any material considered by one of skill to be useful in the systems taught herein. For example, the material can include a flexible tube of polymer such as, for example, TEFLON or polyethylene. In some embodiments, the side lumen runs parallel to the length of the channel in the distal section of the channel and then helical proximal to the distal section of the channel. The pitch of the helix can vary, for example, from about 1.0" to about 6.0", from about 2.0" to about 5.0", from about 1.0" to about 4.0", from about 3.0" to about 5.0", about 4.0", or any range therein in 0.1" increments. By routing the side lumen helically, the wire tension can be distributed all around the shaft so that the shaft can be rotated in any orientation smoothly and remain at least substantially stable. In some embodiments, the pull wire can run from the wire actuator in the handle into the side lumen, out of the distal end of the side lumen, and looped around a rigid ring. The rigid ring (stainless steel, 0.002-0.005" thick, 0.040"-0.25" long) at the distal end and back into the side lumen and out into the handle and attached to the wire actuator. The handle can be operatively connected to the channel, the handle having a housing, and a lumen in communication with the channel. The wire actuator is operatively attached to the pull-wire inside the housing with a button on the outside of the handle allowing the wire actuator to slide back (proximal) and forth (distal) on the handle to pull and push the pull-wire. Pulling the wire makes the tip flex and become rigid, whereas pushing the wire can make the tip relax and straighten. The slide has a means for locking the wire actuator in place, for example, using complementary ratchet teeth on the housing and wire actuator mechanism. When the wire actuator button is pressed, the ratchet teeth can disengage and unlock the pull-wire. In some embodiments, the tip can flex from about 0 degrees to about 150 degrees. In another embodiment, the tip can flexed from about 45 degrees to about 100 degrees. The can be designed to be flexible in bending but stiff in torsion, allowing the channel to follow the curvatures of the anatomy and allow for a rotation of the handle from outside the body during use, transmitting torque to rotate the tip to a desired direction.

The tool (working) channels positioned inside the outer tube provide a multi-lumen catheter having manipulable passages for independently manipulating tools from outside the body into the working space inside created by expansion of the retractor. In some embodiments, from 1 to 3 flexible tubes run inside of the outer tube and can be detached from the outer tube, as described herein, which facilitates the flexibility of the system. In some embodiments, these flexible tubes can be attached at two points: (i) the proximal coupler of the retractor, which can be a ring-type structure having ports at the distal end of the outer tube, and (ii) at the proximal end of the shaft, such as at the handle. This can provide a floating arrangement in the outer tube that is unique, constraining the ends of the flexible tubes while allowing for a substantially free-floating movement of the flexible tubes in the outer tube to enhance the flexibility of the system.

In some embodiments, 2 inner tubes can be positioned adjacent to the inner surface of the outer tube to provide, effectively, 3 separate channels. The 2 inner tubes can function as 2 independent tool channels while the space between these first 2 channels and the outer tube functions as a third channel. The third channel can be substantially larger than the other 2 channels. Each of the first 2 tool channels can have, for example, an inner diameter ranging from about 2 mm to about 6 mm, about 3 mm to about 5 mm, or any range therein. In some embodiments, the diameter of the first 2 tool channels can be about 4 mm. Each of the channels can be designed to accommodate an endoscope such as a colonoscope, as well as endoscopic tools that include, for example, forceps, graspers, clip applier, dissectors, snares, electrical surgical probes, or loops. In some embodiments, the largest diameter channel can be the channel for the endoscope.

The channel for accommodating the endoscope can be designed to have an inner diameter, for example, ranging from about 5 mm to about 15 mm, from about 6 mm to about 12 mm, from about 11 mm to about 14 mm, from about 5 mm to about 10 mm, from about 8 mm to about 13 mm, or any range therein in 1 mm increments. The inner tubes can comprise any suitable material known to one of skill to be useful for the purposes set-forth herein, as well as composites thereof. For example, the inner tubes can comprise a fluoropolymer such as TEFLON for lubricity to ease tool or endoscope passage and movements. Other materials that may be used include, for example, polyethylene, polypropylene, PEBAX, nylon, polyurethane, silicone, and composites thereof, each of which may also be used with a lubricant coating. The tubes may also comprise a metallic wire reinforcement such as a braid, mesh or helical coil, each of which may be embedded in the tube.

One of skill should appreciate that the systems taught herein can be used as a surgical suite with a floating, multi-lumen-catheter retractor system having a reversibly-stabilized and reversibly-expandable retractor for a minimally invasive treatment of a subject. In these embodiments, the system can comprise a flexible outer tube for guiding a floating channel and a floating endoscope in a substantially floating arrangement within the system. Due to the construction of the floating system, the system is highly flexible, such that the flexible outer tube can be highly flexible and have a lumen, a proximal end, and a distal end; and, the floating channel can serve as a guide through which a tool is manipulated in a treatment of a target tissue in a subject. The retractor can be a reversibly-stabilized and reversibly-expandable retractor forming a treatment space upon expansion. The retractor can be configured, for example, for the expansion to occur distal to the distal end of the outer tube and to reversibly stiffen an otherwise flexible arrangement of the retractor, the flexible arrangement designed to facilitate the positioning of the system in the subject and to reversibly stiffen for the expansion of the retractor. That is, the system can include a stabilizing/rigidifying structure as in the embodiments described above, which can be slidable to rigidify the element and retractor system.

During a use of the system, the floating channel can be (i) at least slidably-attached to the lumen of the outer tube at a first proximal location and a first distal location and (ii) at least substantially floating in the lumen of the outer tube between the first proximal location and the first distal location. Likewise, during the use of the system, the floating endoscope can be (iii) at least slidably-attached to the lumen of the outer tube at a second proximal location and a second distal location; and, (iv) at least substantially floating in the lumen of the outer tube between the second proximal location and second distal location. And, during the use of the system, the floating arrangement can (v) at least substantially increase the flexibility of the system over a second such system having lumens for a tool and an endoscope, the lumens affixed to the lumen of the outer tube throughout the length between the proximal end and the distal end of the outer tube. The increased flexibility can facilitate an ease of positioning of the system in the subject; and, the reversibly-stiffened arrangement of the retractor can form an at least substantially rigid beam as a structural support for the expansion in the subject for the treatment of the target tissue.

In some embodiments, the retractor comprises at least two expandable retractor elements, each of the members having a proximal end and a distal end, the proximal end slidably engaged with the outer tube, and each of the members configured such that an increase in the amount of sliding of the proximal end toward the distal end compresses the member and expands the retractor. These embodiments can also include a distal nexus or coupler located distal to the distal end of the outer tube and at which the distal end of each of the at least two retractor elements is affixed; and, a stabilizer subsystem connecting the distal nexus to the distal end of the outer tube and having an at least substantially rigid component configured to reversibly stiffen an otherwise flexible portion of the retractor for an asymmetric expansion of the retractor.

In some embodiments, the retractor comprises four expandable retractor elements, each of the members having a proximal end and a distal end, the proximal end slidably engaged with the outer tube, and each of the members configured such that an increase in the amount of sliding of the proximal end toward the distal end compresses the member and expands the retractor. These embodiments can also include a proximal coupler attached to the distal end of the outer tube, the proximal coupler having four retractor ports for the slidable engagement with the four retractor elements, the four retractor ports positioned circumferentially around the proximal coupler and configured to facilitate a reversible, axial sliding of the retractor elements for the asymmetric expansion of the retractor. These embodiments can also include a distal nexus or coupler located distal to the distal end of the outer tube and at which the distal ends of each of the four retractor elements are affixed; and, a stabilizer subsystem connecting the distal nexus to the distal end of the outer tube and having (i) a flexible component that extends from the proximal coupler to the distal nexus and (ii) an at least substantially rigid component that is slidably engaged with the proximal coupler and reversibly extends from the proximal coupler to the distal nexus to reversibly-stiffen the retractor in an asymmetric expansion of the retractor. The retractor elements can be moved to the expanded position in any of the ways discussed above. Also, if desired, only two of the retractor elements expand as in the embodiments described above.

The flexible component and the rigid component can have central axes that are each at least substantially parallel to the central axis of the distal end of the shaft, the rigid component forming an at least substantially rigid beam as a structural support for the asymmetric expansion, the rigid beam having a luminal side and an abluminal side.

The systems provided herein can be used in several different methods of treatment. For example, the systems can be used in a method of treating a gastrointestinal lesion using a multidirectional and multi-angular approach to the lesion. The method can include positioning the system in a subject's gastrointestinal tract, the positioning including placing the retractor in proximity to a target lesion for a treatment; expanding the retractor to create the treatment space for use of the tool; treating the lesion with the tool; collapsing the retractor; and, withdrawing the system from the subject. The lesion can include, for example, a perforation, a tissue pathology a polyp, a tumor, a cancerous tissue, a bleed, a diverticuli, an ulcer, an abnormal vessel, or an appendix.

It should be appreciated that there are a number of procedures and variations, in addition to those taught above, that can be used readily by one of skill in the implementation of the systems taught herein. In some embodiments, one of skill can insert the endoscope through the endoscope channel of the system and extend the distal end of the endoscope distal to the distal end of the retractor to form an assembly. The assembly can then be inserted into a body lumen or orifice, such as the colon, and advanced orally until the distal end of the scope or the lens is in proximity to the target tissue (lesion or defect) to be treated. The system can then be advanced forward over the scope until the retractor is positioned over the distal end of the endoscope while observing the image from the endoscope. The system can be advanced until the target tissue is located between the proximal coupler and distal nexus of the retractor while observing the image from the endoscope. The handle or outer tube can be rotated to rotate the retractor so that the target tissue is at the desired position relative to the retractor members while observing the image from the endoscope. The retractor can then be straightened and stabilized by converting the flexible beam to a rigid beam. The retractor can then be expanded by moving the retraction actuator forward on the handle while observing the image from the endoscope. This action pushes the tissue outwards, creates a working space around the target tissue, and anchors and stabilizes the target tissue. Optionally, while the retractor is expanded, the system can be pulled back to shift the peak of the most expanded members distally to improve working distance between the endoscope and the peak of the asymmetric work space, wherein the peak is generally recommended to be located around the target tissue. With the instruments inserted into the working (tool) channels, insert the working channels into the proximal ports of the system and advance the instruments and channels distally until the tips of the working channels are distal to proximal coupler of the retractor while observing the image from the endoscope. At this time, the tips of the working channels can be flexed to the appropriate angulation for the tools to approach the lesion to be treated. The working channels can be rotated and moved axially as needed to the desired position for the tools. Likewise, the instruments/tools can be advanced relative to the distal end of the working channels as needed to extend the instruments as needed to reach the target tissue. Various instruments can be inserted through the working channels as desired, and both the endoscope and the instruments can be advanced and positioned independently into the working area to further manipulate and visualize the target tissue at closer proximities or angulations. This is because, in some embodiments, the endoscope can also flex within the working space.

In some embodiments, it's desirable to provide for delivering a system taught herein with an optional cover, or sheath that covers a portion of the system, including the retractor, during delivery of the retractor to a target site, during a treatment of a target tissue at the target site, during a removal of the target tissue, and/or during a removal of the system from the subject, or a combination thereof. Recall that some embodiments of such an optional cover 355 have been illustrated herein, for example, in FIGS. 3A and 3K. One of skill will appreciate that the retractor has elements that can catch, snag, or otherwise disturb or contact tissue during delivery, or removal, of the retractor to or from the target site. Also, the treatment of the target tissue may include, for example a dissection of tissue that can be performed within the cover without intermingling the target tissue with the surrounding tissues. Moreover, the dissected tissue may be a cancerous or other tissue that is desirable to contain during treatment or removal by encapsulating it within the cover. The terms "cover" and "sheath" can be used interchangeably in many embodiments, and one of skill can appreciate that such embodiments are open to improvements, as taught herein.

Figure 10A:
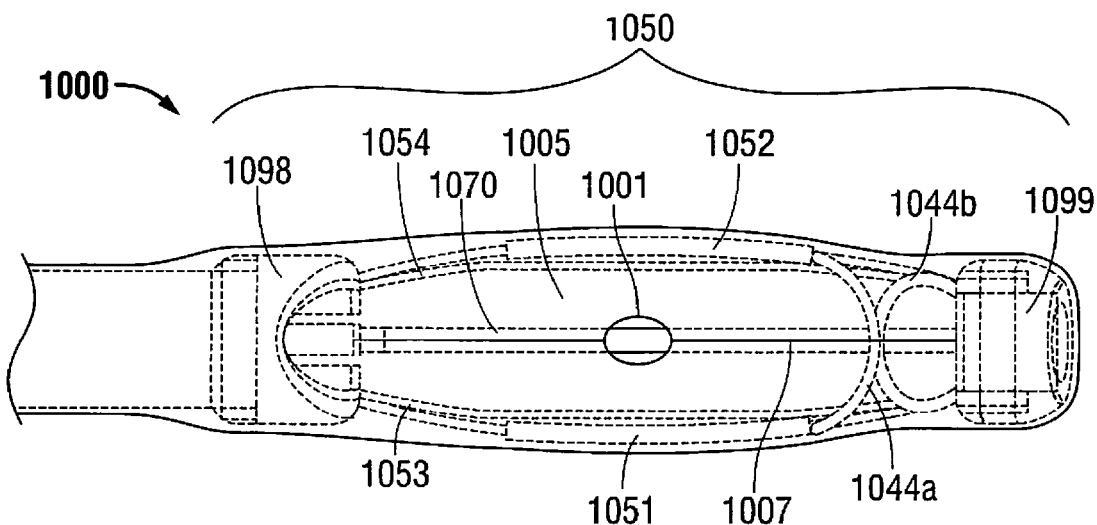
Figure 10B:
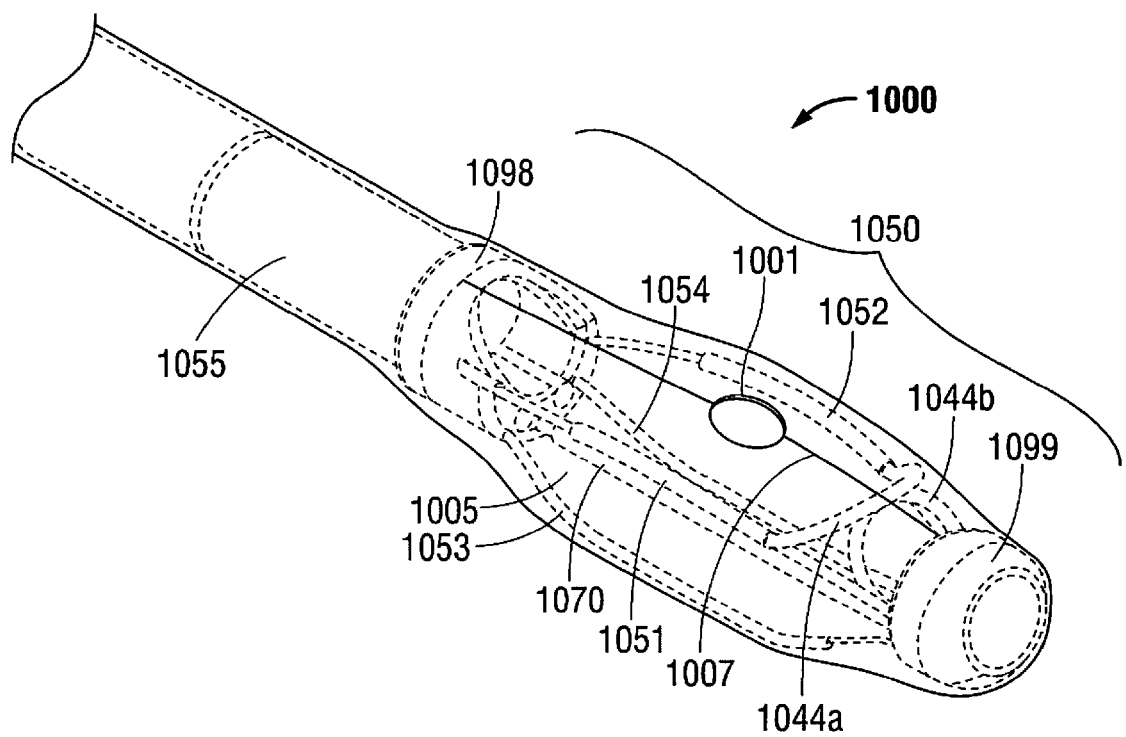
Figure 10C:
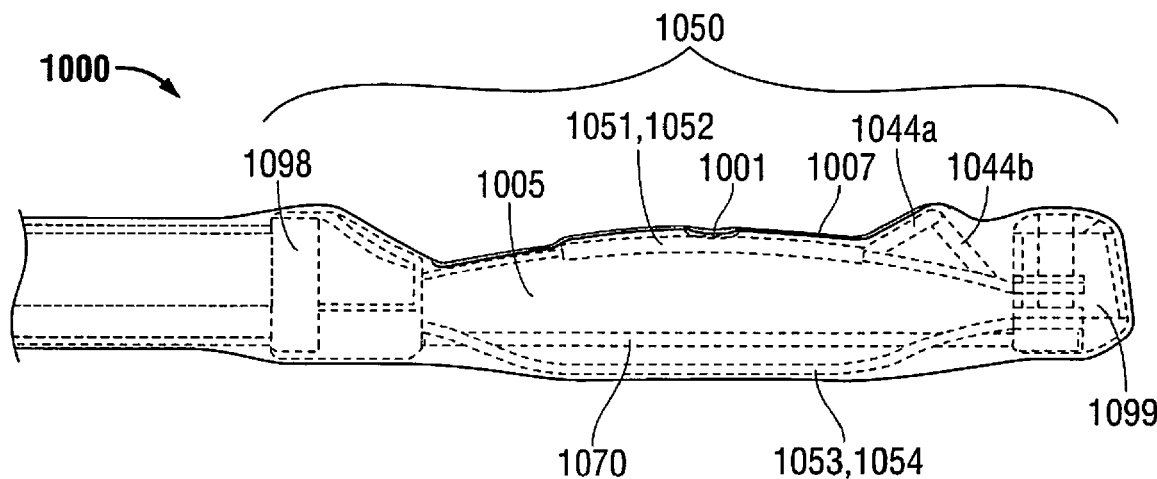
Figure 10D:
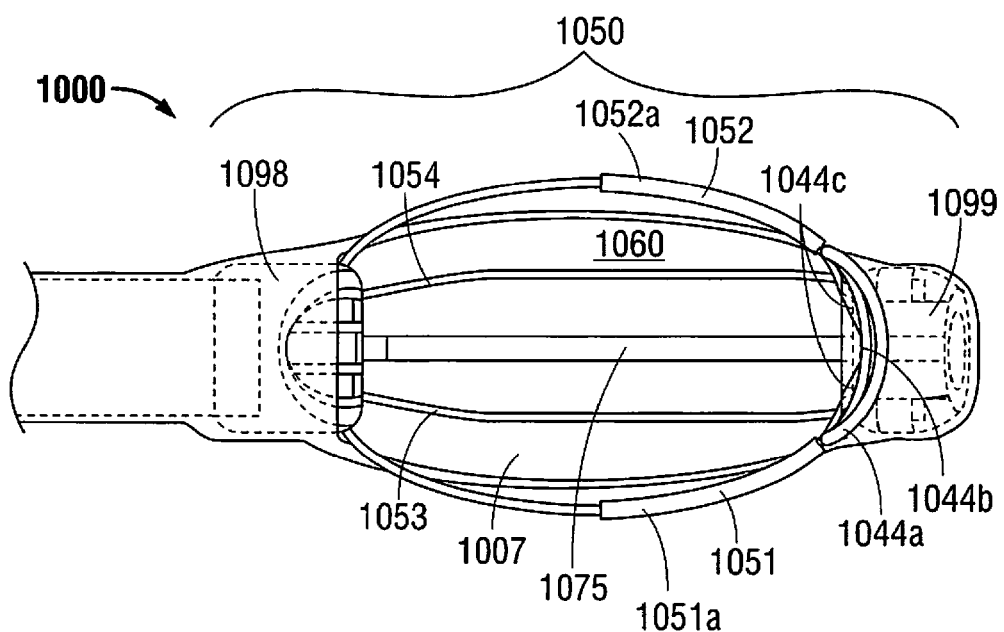
Figure 10E:
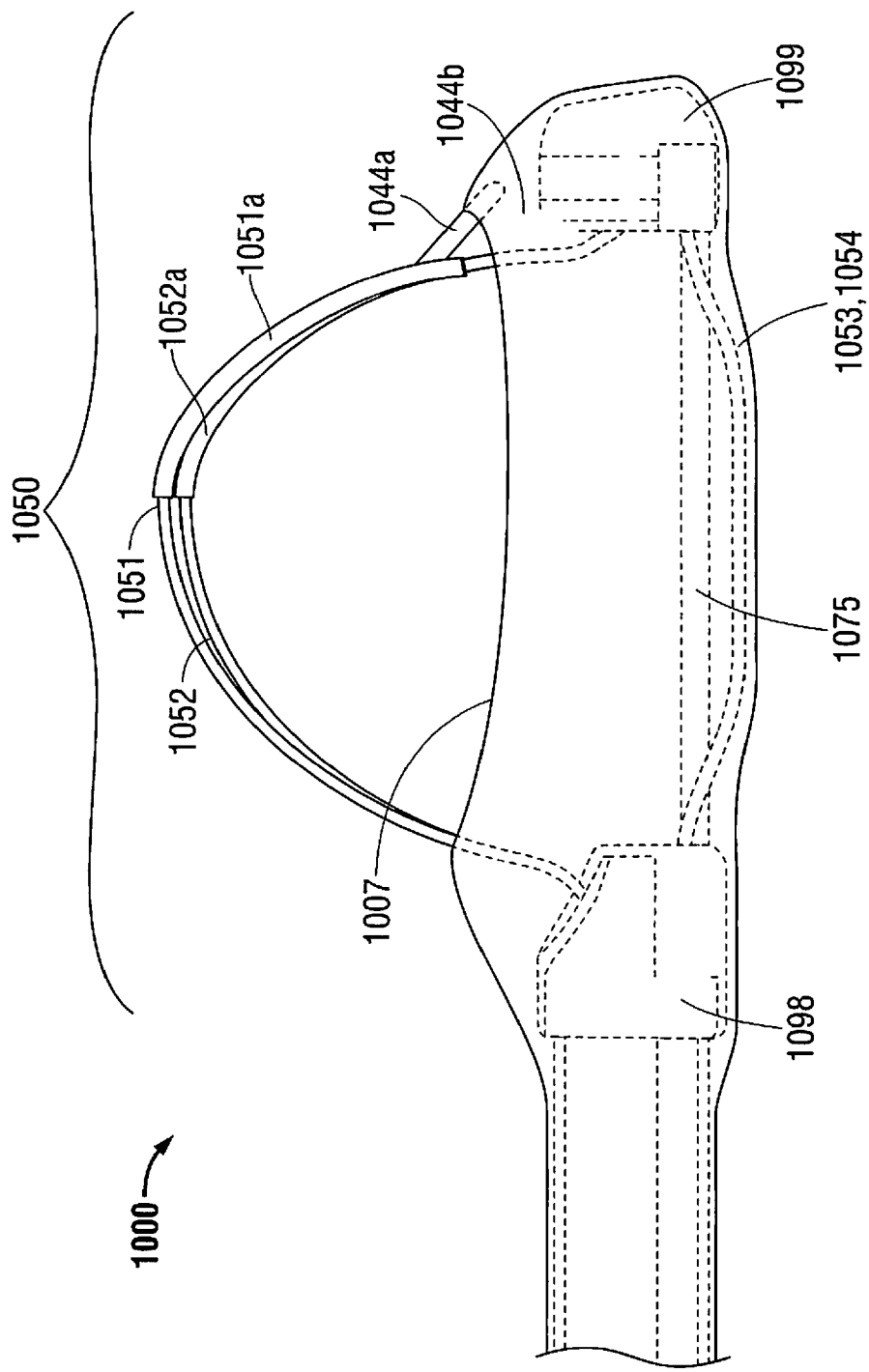

FIGS. 10A-10E illustrate a retractor sheath covering a retractor of a system as taught herein, according to some embodiments. FIGS. 10A-10C show top, oblique, and side-views showing a flexible, clear sheath 1000 that covers a collapsed configuration of the retractor 1050 to render an at least substantially smooth and/or atraumatic surface 1005 for a delivery of the retractor 1050 to a target site (not shown) for a treatment of a target tissue (not shown). In FIGS. 10A-10C, the cover is in a closed configuration that can be sustained until the expansion of the retractor 1050 for the treatment, or it can be reversibly-obtained following the treatment. FIGS. 10D and 10E show a top-view and side-view of an expanded configuration of the retractor with the cover in an open configuration for the treatment.

The sheath 1000 can be designed to prevent or inhibit the retractor elements 1051,1052,1053,1054 and bridge members 1044a, 1044b from catching, snagging, or otherwise disturbing or contacting tissue during a delivery or removal of the retractor 1050 to or from the target site. The sheath 1000 is attached at one end to the distal hub or coupler 1099 and extends proximally past the proximal coupler or hub 1098 and is attached to the outer surface of the catheter 1055. Alternatively, the sheath 100 can be attached at a proximal end to proximal coupler 1098. Retainers can be used at any position around the retractor to facilitate a retention of the configuration of the working space 1060, for example, to retain the configuration under forces of the expansion of the retractor 1050. During the procedure the sheath 1000 can also prevent or inhibit tissue from entering the retractor 1050 until desired. The sheath 1000 can also act as a collection means for entrapping and/or pulling out a resected tissue, which can be particularly desirable in the resection of cancerous tissue in some embodiments. The sheath 1000 can be at least substantially closed around the retractor 1050 during delivery, and can be designed to open as the retractor 1050 is expanded to create the working space 1060 for the treatment. Alternatively, the expansion of the retractor elements and the sheath can be independent.

A flexible beam 1070 can be converted to the at least substantially rigid beam 1075 using the methods and structure of conversion as described above in conjunction with the other embodiments. For example, an actuator can be operably connected to the beam (rigidifying structure) 1075 to advance it into a lumen of the flexible beam 1070, or alternatively advance it over the flexible beam 1070 (as shown in FIG. 10D), to stiffen (make more rigid) the flexible beam 1070. The bridge member 1044a can connect the expandable retractor elements 1051, 1052 and bridge member 1044b can connect elements 1053, 1054 to restrict lateral movement and stabilize the retractor as in the other bridge members described herein. In alternate embodiments, bridge member 1044b extends from bridge member 1044a and connects to elements 1053, 1054 such that all four elements 1051, 1052, 1053 and 1054 are connected by the bridge elements 1044a, 1044b. Bridge member 1044c can connect elements 1053, 1054. Coverings 1051a and 1052a can be applied to the retractor elements 1051, 1052, respectively, to control expansion as described in the embodiment of FIG. 11 below.

In some embodiments, the sheath 1000 can be perforated longitudinally (not shown}, designed such that the sheath 1000 opens upon expansion of the retractor 1050 through tearing of the perforation at the target site. In some embodiments, a tongue-and-groove mechanism, for example a ZIPLOCK mechanism, can be used to at least substantially close a slit 1007 at the top of the retractor 1050 which can also open upon the expansion of the retractor 1050 at the target site. In some embodiments, a larger perforation, or unclosed portion 1001, can remain in the sheath 1000 to facilitate the tearing or opening of the sheath at the target site upon the expansion of the retractor 1050. In some embodiments, the terms "slit" and "opening" can be used interchangeably.

In some embodiments, the sheath can be reversibly opened, such that the sheath can be re-closable. For example, a drawstring, cable, or wire, can be operably positioned in communication with the opening for the re-closing of the opening by pulling or pushing the drawstring, cable, or wire from outside the patient during the treatment. In some embodiments, the edges of the opening can form longitudinal pockets or channels for pulling or pushing the drawstring, cable, or wire as desired from outside the patient during the treatment, such as by routing the drawstring, cable, or wire through the system and, perhaps, through the handle as with the other actuation means. In some embodiments, a drawstring is used to re-close the sheath, wherein the strings can be tensioned at the handle to close the slit, or loosened to allow the retractor to expand. In some embodiments, the sheath has a stiffening strip running transversely around the mid portion of the cage to facilitate the cage wires expanding without catching on the surrounding sheath. The stiffening strip can be another layer of the sheath welded or glued onto the existing sheath. It can also be formed as a thickened area. Alternatively, a stiffer material can be inserted in the pocket running transversely. The stiffening material may be the same as that of the sheath or it may be a stiffer material.

One of skill will appreciate that any of the known materials and/or methods of covering the sheath may be useful for the purposes taught herein. For example, the sheath can range from about 10 mm to about 30 mm at the ends that are attached to the proximal coupler and distal nexus, each of which can be used to define the ends of the retractor 1050. Moreover, the sheath can be heat welded, glued, or heat-shrunk to the proximal coupler and/or distal nexus, or perhaps substantially proximal or distal to these components, to fasten the sheath to the retractor. In some embodiments, the sheath may even cover the system as a sterilizing, or clean, cover, such that the sheath is an extension of a disposable and/or replaceable component that may be applied, for example, in a sterilization process. And, in some embodiments, the sheath can be larger at the mid portion where the diameter can range, for example, from about 20 mm to about 40 mm in a closed configuration. The sheath can be, for example, opaque, translucent, or clear, and the material composing the sheath can be, for example, a polyethylene, nylon, fluorinated ethylene propylene (FEP), TEFLON, polyethylene terephthalate (PET), or polycarbonate. And, in some embodiments, the sheath material can range, for example, from about 0.0010" to about 0.0060" thick, from about 0.0020 to about 0.0080" thick, from about 0.0030" to about 0.0050" thick, from about 0.0010" to about 0.0030" thick, from about 0.0005" to about 0.0100" thick, about 0.0020" thick, or any range therein in about 0.0005" increments.

In use, when the retractor system 1050 is moved from the collapsed insertion position of FIG. 10B to the expanded position of FIG. 10E, the expandable retractor elements are expanded away from the sheath 1000. The sheath 1000 can remain open at a surface facing the target tissue to be treated, e.g., removed, from the patient's body. Alternatively, the sheath 1000 can remain closed and be opened by an endoscopic tool to receive the removed lesion. Note as shown in FIG. 10E, in the expanded position, the sheath 1000 is covering the retractor elements 1053, 1054 and rigid beam 1075 and is spaced from expanded elements 1051, 1052. In alternate embodiments, the sheath can also cover elements 1051, 1052 in their expanded configuration.

Figure 11:
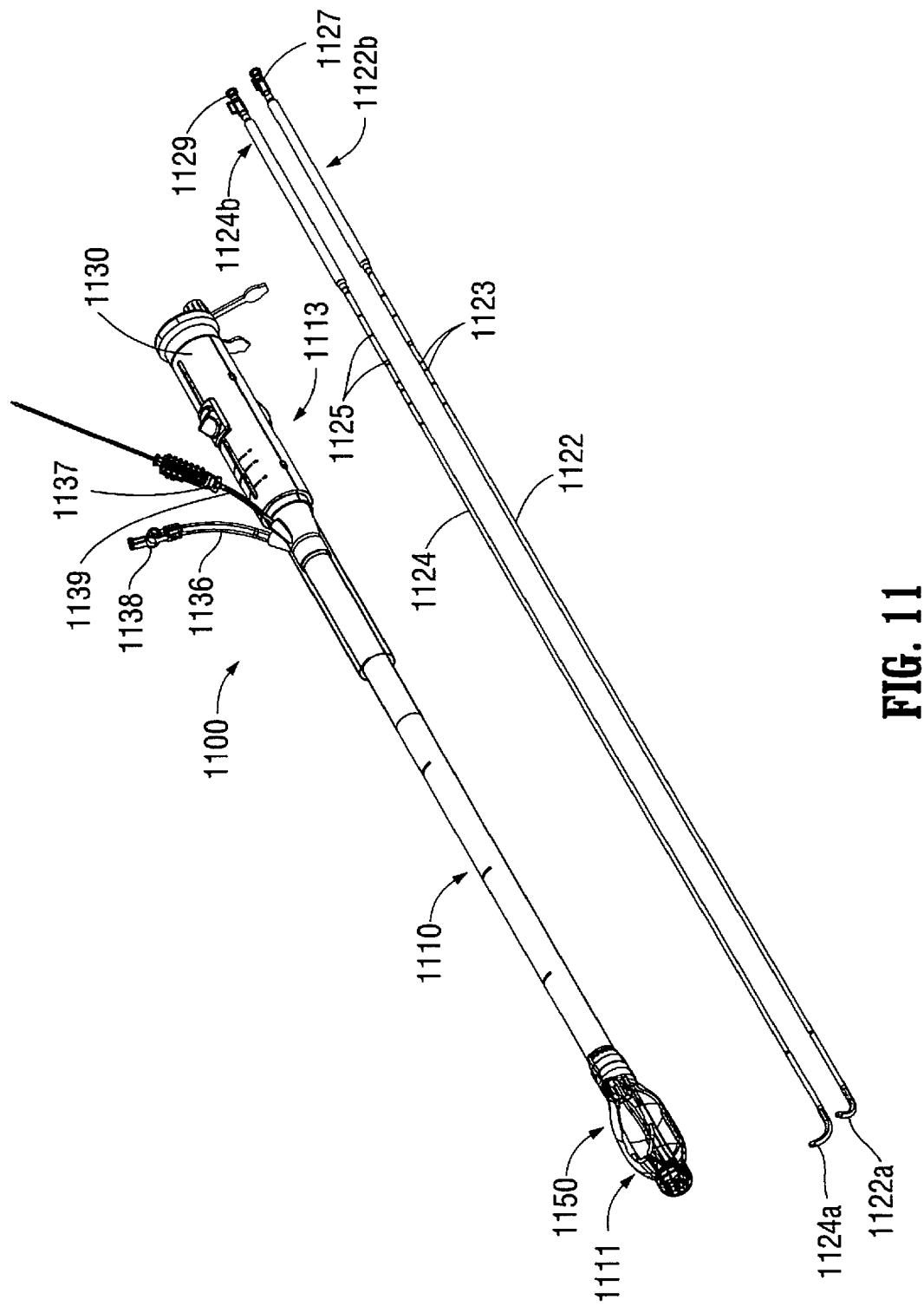
FIG. 11 is a perspective view of an alternate embodiment of the system showing the catheter and two tool channels.

FIGS. 11-30 illustrate alternative embodiments of the system, designated generally by reference numeral 1100. System 1100 includes a multi-lumen catheter or tubular member 1110 configured to receive one or more tool channels or flexible instrument guides. FIG. 11 shows two tool channels 1122 and 1124, it being understood that in some embodiments, only one tool channel can be utilized and in other embodiments more than two tool channels can be utilized, with the catheter provided with a sufficient number of lumens. The tool channels 1122, 1124 can be packaged as a kit with the catheter 1110 as shown in FIG. 11. Alternatively, the tool channels 1122, 1124 can be packaged separately. In other embodiments, the tool channels are packaged already inside the lumens of the catheter 1110. Each tool channel 1122, 1124 has a lumen (channel) to receive an endoscopic instrument (tool) therethrough.

Figure 12:
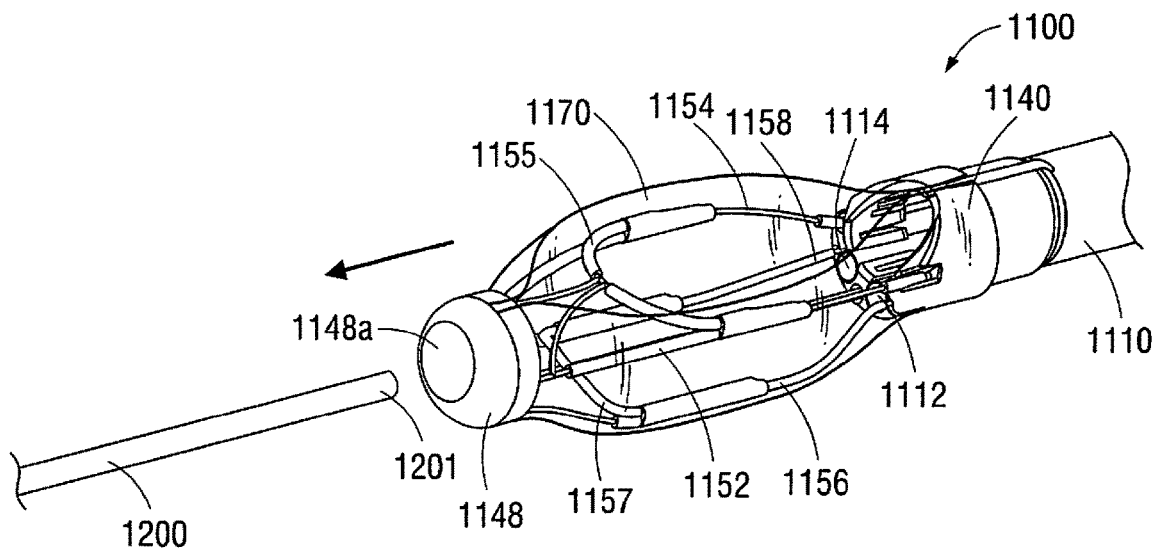
FIG. 12 is a perspective view of the catheter of FIG. 11 being inserted over the proximal end of the endoscope of FIG. 13 (prior to insertion of the endoscope into the colon), the retractor system shown in the collapsed position.

The tool channels (also referred to herein as flexible tubes or flexible guides) 1122 and 1124 are inserted through the proximal end of the catheter 1110 and advanced through respective lumens 1112, 1114 in the catheter 1110 (see FIG. 12). As shown in FIG. 16, which illustrates a proximal portion 1113 of catheter 1110, the catheter 1110 can include ports 1115, 1117, cooperating with the lumens 1112, 1114, respectively (see e.g. FIG. 13), which can include valves to maintain insufflation when the tool channels 1122, 1124 are inserted therethrough and translated axially therein. Tool channel (tube) 1122 preferably has a pre-bent tip 1122a, best shown in FIGS. 11 and 18, to provide a curved distal end. Tool channel (tube) 1124 also preferably has a pre-bent tip 1124a, providing a curved distal end. When the tool channels 1122, 1124 are inserted into the lumens 1112, 1114 of catheter 1110, the tips 1122a, 1124a are preferably substantially straightened to facilitate advancement through the lumens. When the tool channels 1122, 1124 are advanced sufficiently distally so the distal tips 1122a, 1124a are exposed from the confines of the walls of the catheter lumens 1112, 1114, the tips 1122a, 1124a, return to the pre-set curved position. This can be understood with reference to FIG. 18 which illustrates in phantom the straightened position of the tool channels 1122, 1124 for movement within the catheter 1110. As in the other embodiments disclosed herein, the tool channels 1122, 1124 can be composed of superelastic material, although other materials to provide the curved tip which returns from a substantially straight insertion shape to a curved shape when exposed can also be used, such as stainless steel. Also, as in the other embodiments disclosed herein, shape memory properties of material such as Nitinol can be used with a memorized curved tip shape. In alternative embodiments as described above, the tool channels 1122, 1124 can have a mechanism such as a pull wire which is actuated to bend its distal end. The tool channels 1122, 1124 in the embodiments of FIGS. 11-30 are unattached to the catheter 1110 so that the user can freely control their axial movement from a proximal end portion 1122b, 1124b, during use. However, it is also contemplated that in alternate embodiments the tool channels can be attached to the catheter.

The tool channels 1122, 1124 can optionally include markings 1123, 1125, respectively, at a region proximal to the catheter 1110 to provide a visual indicator to the user of the depth of insertion of the tool channels 1122, 1124 through the catheter lumens 1112, 1114. The tool channels 1122, 1124 can have a luer fitting 1127, 1129, respectively, (FIGS. 11 and 19A) with a valve, at the proximal end which can close off backflow of insufflation gas from the body. This maintains insufflation when the endoscopic tool is inserted through the tool channels 1122, 1124 as described below. The tool channels in an alternate embodiment shown in FIG. 19B have a hemostatic valve 1121A, 1121B connected at a proximal end of tool channels 1122', 1124', respectively, to maintain insufflation during tool insertion. As shown, valves 1121A, 1121B are proximal of luer fittings 1127', 1129'. The tool channels 1124', 1126' are identical to tool channels 1124, 1126 in all other respects.

In one embodiment, the tool channels 1122, 1124 can be composed of a flexible soft material, such as Pebax. A superelastic nitinol backbone can in some embodiments be embedded in the wall of the Pebax material, e.g., within the curved portion. Other materials are also contemplated.

Catheter 1110 also preferably has a lumen 1116 (see e.g., FIG. 16) configured and dimensioned to receive an endoscope 1200. In some embodiments, the lumen 1116 is dimensioned to receive a conventional endoscope, e.g., a conventional colonoscope, and the catheter 1110 is back-loaded over the endoscope. This is described in more detail below in conjunction with the method of use. In alternate embodiments, the lumen 1116 can receive an articulating endoscope. Moreover, in alternate embodiments, the endoscope can be inserted into the catheter and inserted into the body lumen.

Figure 31A:
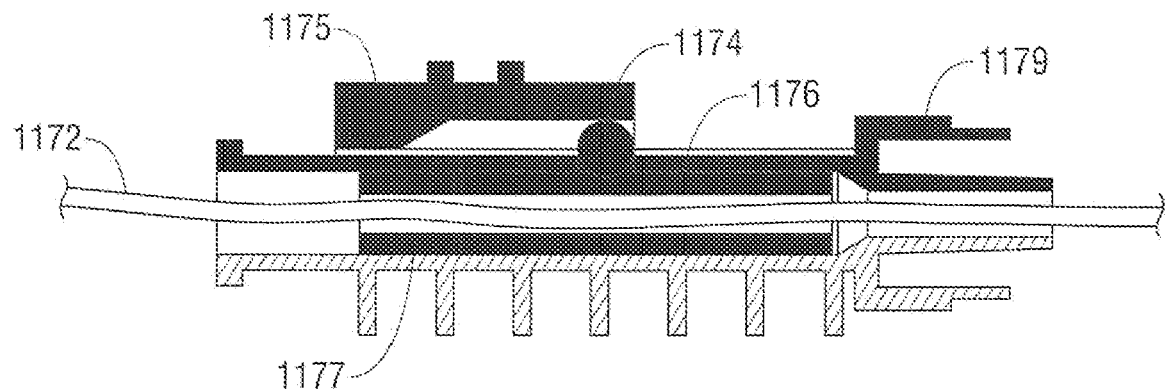
FIGS. 31A and 31B are cross-sectional views illustrating the switch for retaining the suture for closing the covering (bag).
Figure 31B:
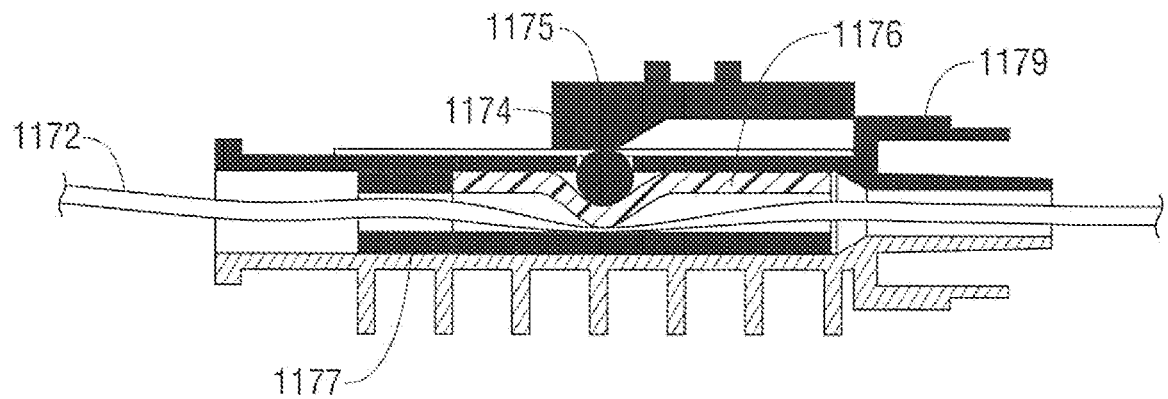

With reference to FIGS. 11 and 16, catheter 1110 includes a handle housing 1130 at the proximal portion 1113 which contains two actuators: actuator 1132 for controlling movement of the retractor system 1150 and actuator 1134 for controlling movement of the rigidifying (stabilizing) structure. These are discussed in more detail below. Catheter 1110 also includes tubing 1139 having a luer coupling 1137 and a control switch 1175 (see FIGS. 31A, 31B) for closing off an internal gasket 1176. The string, e.g., suture, 1172 for closing covering 1170 is secured by the elastomeric gasket 1176 as the switch 1174 is moved from the position of FIG. 31A to the position of FIG. 31B. More particularly, in the initial position of FIG. 31A, the ball valve 1174, seated in a slot in the housing 1179, does not apply a force to the gasket 1176. This enables the suture 1172 to freely move within the lumen of the catheter. When it is desired to lock the suture 1172 in position, i.e., after the suture 1172 is tensioned to close the covering 1170, the switch 1175 is slid forward, thereby camming the ball 1174 downwardly (as viewed in the orientation of FIG. 31B) to collapse the lumen in the gasket 1176 against the suture 1172 to thereby secure the suture 1172. This locks the suture 1172 against movement which thereby maintains the covering (bag) in the closed position encapsulating the target tissue as described herein. Note that the reverse movement of the switch 1175 unlocks the suture 1172 to enable free movement of the suture 1172. Catheter 1110 also has tubing 1136 having a one-way stopcock 1138 to provide an insufflation port. This port can be used to supplement the insufflation gas provided by the endoscope 1200. The insufflation gas flows through lumen 1116 in the area around the endoscope 1200 since the cross sectional dimension of the lumen 1116 exceeds the cross-sectional dimension of the endoscope 1200 to leave a sufficient gap. As shown, the tubings 1139, 1136 are positioned distal of the actuators 1132, 1134, Turning now to the retractor system 1150, which forms a working space expanding system, and in certain clinical applications, a body lumen reshaping or reconfiguring system, and with initial reference to FIG. 13, the retractor system 1150 is positioned at the distal portion 1111 of the catheter 1110 (distal of proximal hub 1140) and includes flexible retractor elements 1152 and 1154. Retractor system also includes retractor elements 1156 and 1158. Retractor elements 1152, 1154 form the expandable elements which create the working chamber (space) within the body lumen and form an asymmetric cage. Retractor elements 1156, 1158 form the base of the retractor system, thus helping to define the retractor cage along with elements 1152, 1154. In some embodiments, retractor elements 1156, 1158 do not undergo any change when the retractor system 1150 moves from the collapsed insertion position to the expanded position; in other embodiments, retractor elements 1156, 1158 undergo a slight change in position, i.e., slight expansion or bowing, when the retractor system 1150 is expanded. Retractor elements 1152, 1154, are expandable to form an asymmetric working chamber to improve visibility and working space as described in detail above with respect to the other systems forming asymmetrical working spaces.

Figure 15:
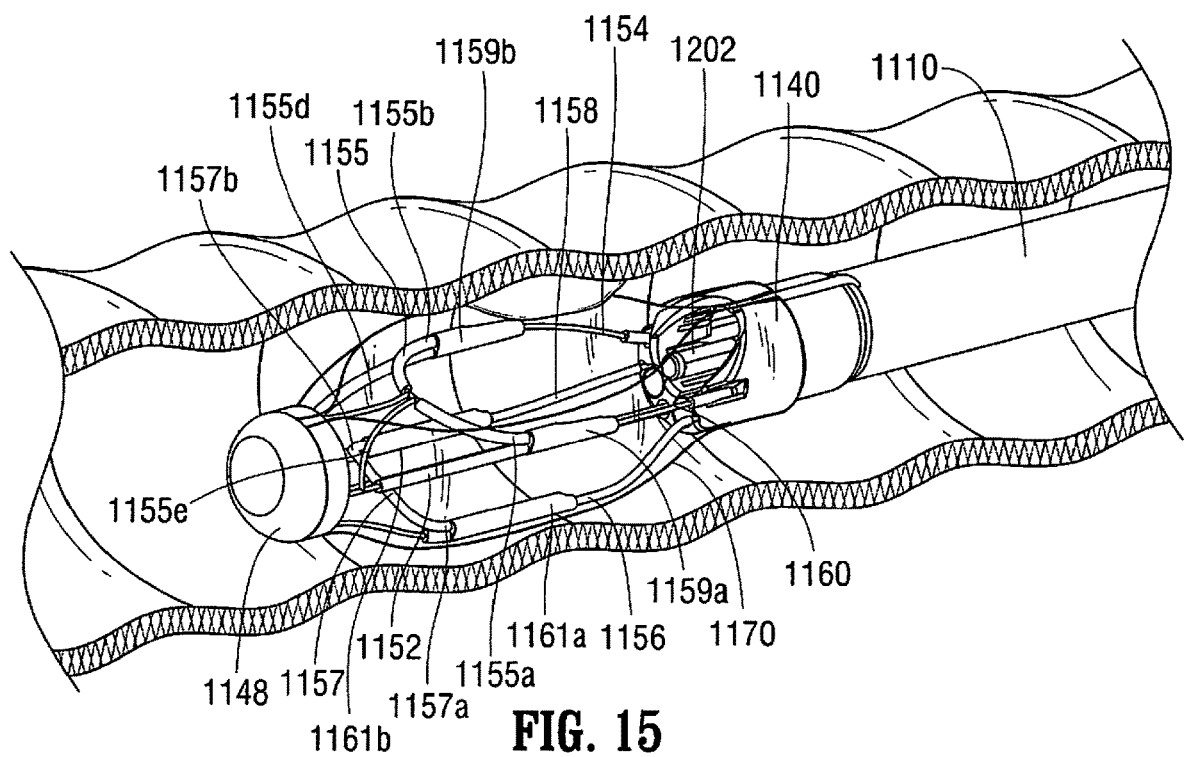
FIG. 15 is a perspective view showing the catheter fully advanced over the endoscope to the desired position adjacent the target tissue, the retractor system shown in the collapsed (non-expandable) position.
Figure 16:
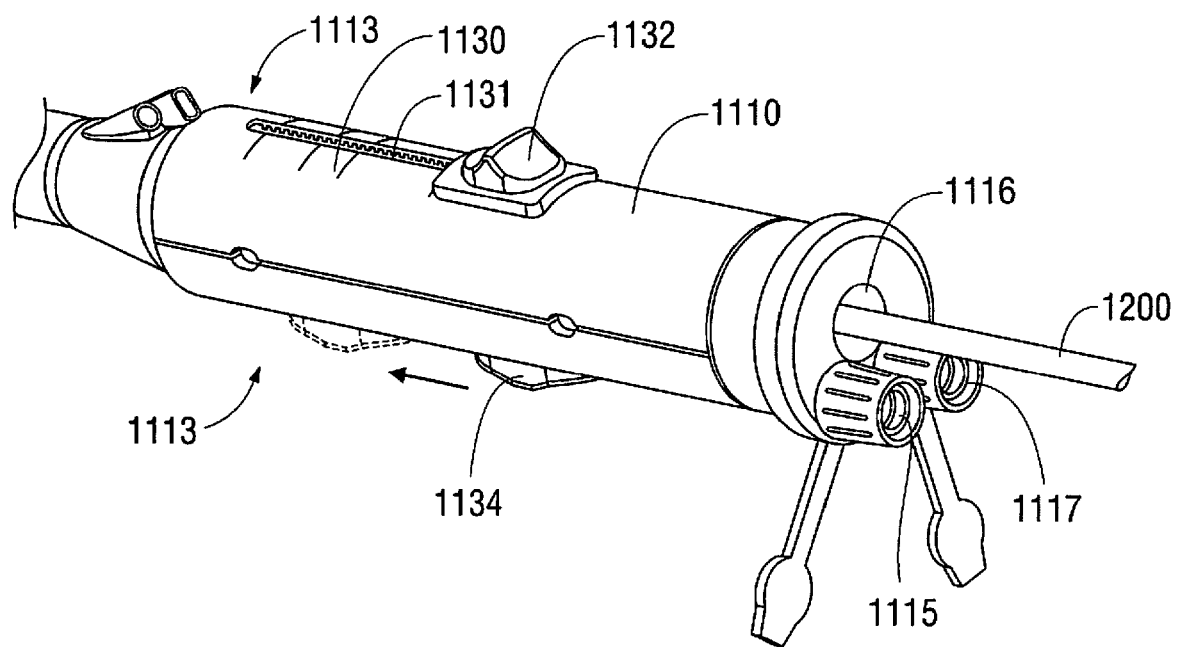
FIG. 16 is a perspective view of the proximal end of the catheter of FIG. 11.
Figure 21A:
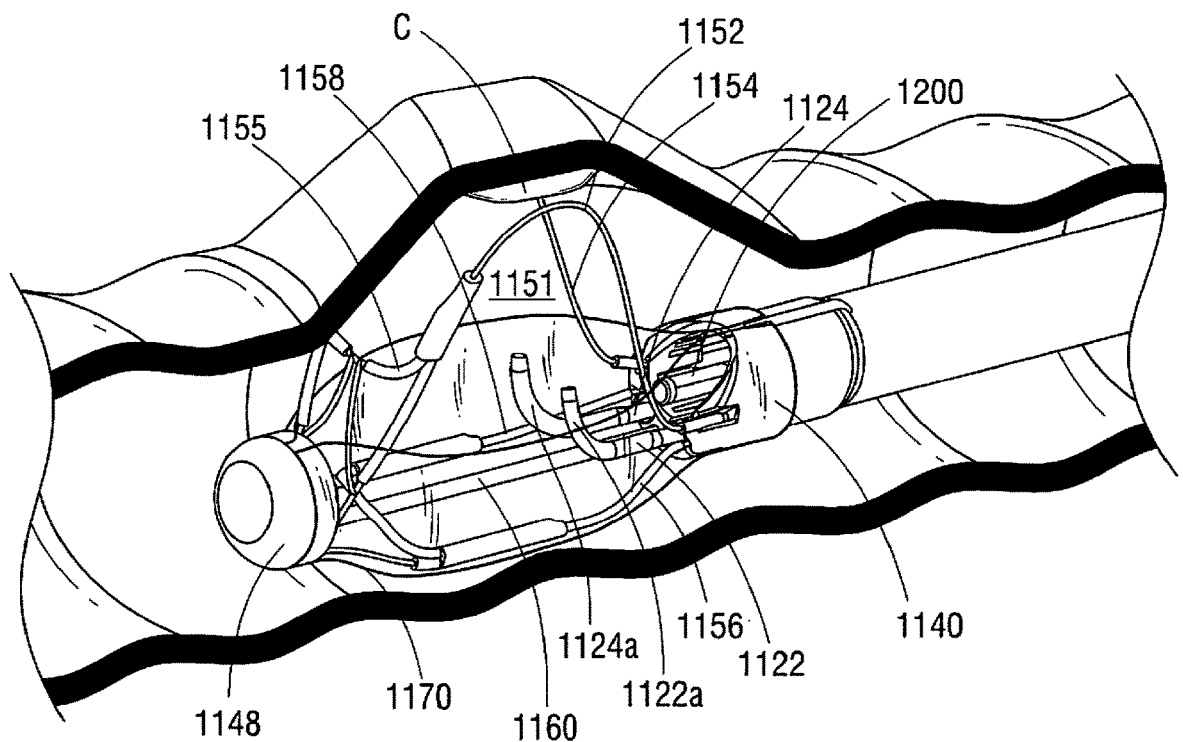
FIG. 21A is a view similar to FIG. 15 showing the retractor system in the expanded position and further illustrating the tool channels being advanced into the working space (chamber) created by the expansion of the retractor system.

As shown by comparing FIGS. 15 and 21A, retractor elements 1152 and 1154 move from a collapsed insertion position wherein they preferably do not extend beyond, or significantly beyond, the transverse dimension of the catheter 1110 to an expanded position wherein they bow laterally outwardly and have a transverse dimension extending beyond the transverse dimension of the catheter 1110. Also by comparing FIGS. 15 and 21A, it can be seen that lower (as viewed in the orientation of these figures) elements 1156, 1158 in the collapsed position do not extend beyond, or significantly beyond, the transverse dimension of the catheter 1110 and when the retractor is expanded, remain substantially in the same position so they still do not extend beyond, or significantly beyond, the transverse dimension of the catheter 1110. In some embodiments, the elements 1156, 1158 do not extend at all beyond the transverse dimension of the catheter 1110. As in the embodiments described above, the retractor system 1150, i.e., the retractor elements 1152, 1154, expand to only one side of a plane passing through a longitudinal axis of the catheter 1110, thereby creating the asymmetric working space 1151 (and asymmetric cage), with its attendant advantages described herein.

Retractor elements 1152, 1154 have a bridge member 1155 to add stability to the retractor and maintain a desired orientation of the retractor elements during the expansion. The bridge member 1155 is attached to the two retractor elements 1152, 1154, preferably at an intermediate portion, to create a transverse structure for the elements 1152, 1154, limiting side-to side movement. As shown, bridge member 1155 has a first arm 1155*a* connected to retractor element 1152 and a second arm 1155*b* connected to retractor element 1154. The upper surface (as viewed in the orientation of FIG. 15) can be arcuate as shown. The bridge member 1155 can be a separate component attached to the retractor elements by tubular elements 1159*a*, 1159*b*, which are fitted over and attached to retractor elements 1152, 1154, respectively. In this version, the tubular element 1159*a*, 1159*b* has a first opening to receive the retractor element and a second opening to receive an arm of the bridge member, although alternatively they can both be received in the same opening. Note the tubular elements 1159*a*, 1159*b* also bulk up the diameter of the retractor elements 1152, 1154 since in some embodiments the retractor elements 1152, 1154 are about 0.035 inches in diameter (although other dimensions are contemplated). Other methods of attachment of the bridge members are also contemplated. Alternately, the bridge member 1155 can be integrally formed with one or both of the retractor elements 1152, 1154. The bridge member 1155 can be composed of a material similar to the elements 1152, 1154 or can be composed of a different material. The bridge member 1155 can also include legs 1155*d* and 1155*e* which are connected to lower elements 1158, 1156, respectively, to attach the bridge member to lower elements 1158, 1156, respectively, to add to the stability of the retractor system. These leg members 1155*d*, 1155*e* are preferably composed of soft elastomeric material such as polyurethane tubing to add more structure to the cage and facilitate expansion of the cage in a more predictable fashion.

Additional bridge members (not shown) can be provided on the retractor elements 1052, 1054 to increase stability. The bridge member 1055 can, in some embodiments, in the collapsed position, extend substantially axially as in FIGS. 15 and 17A, but change to angle inwardly (downwardly) toward the longitudinal axis of the catheter 1010 in the expanded position of the retractor elements 1052, 1054 such as in FIG. 21A.

An additional bridge member 1157 (or alternatively multiple bridge members) extends between the two lower (as viewed in orientation of FIG. 15) retractor elements 1156, 1158. These elements 1156, 1158 can help open up the lower section of the retractor system 1150 and help form the cage for the working space, and the bridge member(s) 1157 can help to stabilize these elements 1156, 1158, e.g., limit side to side movement. The bridge member 1157 as shown has arms 1157*a*, 1157*b* connecting to elements 1156, 1158, respectively. The bridge member 1057 can be a separate component attached to the retractor elements by tubular elements 1161*a*, 1161*b* which are fitted over and attached to retractor elements 1156, 1158, respectively. The tubular elements 1161*a*, 1161*b* can have a first opening to receive the element 1156 or 1158 and a second opening to receive an arm of the bridge member 1157, although alternatively they can both be received in the same opening. Other ways of attaching the bridge member(s) are also contemplated. Alternatively, the bridge member 1157 can be integrally formed with one or both of the retractor elements 1156, 1158. The bridge member 1157 can be composed of a material similar to the elements 1156, 1158 or can be composed of a different material.

Additional bridge members (not shown) can be provided on the retractor elements 1156, 1158 to increase stability. The bridge member 1157 can, in some embodiments, in the collapsed position, be substantially parallel with a longitudinal axis of the catheter 1110 or extend substantially axially such as in FIG. 15, and substantially remain in this position in the expanded position of the retractor elements 1152, 1154 as in FIG. 21A since in this embodiment, the retractor elements 1156, 1158 remain in substantially the same position when the retractor system 1150 is expanded.

The catheter 1110 includes a proximal coupler (cap) 1140 through which the retractor elements extend. Handle housing 1130 includes a longitudinally extending slot 1131 (FIG. 16) along which retractor actuator 1132 axially slides. The retractor elements 1152, 1154 are coupled to the actuator 1132 via block 1146, shown in FIGS. 20A and 20B. That is, each retractor element 1152, 1152 has a proximal extension that extends through the respective lumen 1112, 1114 in the catheter 1150 and is connected at its proximal end to the block 1146. In this manner, when the actuator 1132 is moved along axial slot 1131 from its proximal position of FIG. 20A to its distal position of FIG. 20B, the block 1146 is moved distally, thereby forcing the retractor elements 1152, 1154 laterally outwardly since the elements 1152, 1154 are fixedly attached to the distal coupler 1148 at their distal ends. Elements 1156, 1158 in this embodiment, are fixedly attached to the distal coupler 1148 at their distal ends, and fixedly attached to the proximal coupler 1140 (or other portion of the catheter 1110) at their proximal ends such that movement of actuator 1132 does not effect movement of these elements 1156, 1158. It should be appreciated, however, that if it is desired to have the elements 1156, 1158 move, e.g., flex slightly outwardly when the retractor 1150 is expanded, these elements 1156, 1158 can be attached to the block 1146 so they would be moved when actuator 1132 is advanced, or alternatively attached to a separate actuator. In one embodiment, the elements 1152, 1154, 1156 and 1158 can be fixed within slots formed in the distal coupler 1148. Note the proximal and distal couplers 1140, 1148 can have openings dimensioned to receive an endoscope when the catheter 1110 is backloaded over the endoscope as described below. Housing 1130 can include a plurality of teeth (not shown) similar to the teeth of FIGS. 6A-6D for engagement by a tooth coupled to the actuator 1132, thereby forming a retaining or locking mechanism to retain the retractor elements in one of several select positions. A release mechanism for the retaining or locking mechanism can be provided.

Additionally, it should be appreciated that alternative ways to expand the retractor elements can be utilized, including for example providing relatively movable couplers 1140, 1148 to expand the retractor elements 1152, 1154 (and optionally 1156, 1158) in the same manner as the couplers described above, e.g., couplers 198, 199. The retractor elements can also alternatively be made of self-expanding material, such as shape memory material, which expand when exposed from the catheter or sheath.

Retractor elements 1152, 1154 can optionally have a small crimp forming a flattened position at a distal end adjacent where they are anchored to the distal coupler 1148. This reduces the bending stiffness at the point so it acts like a hinge to create a more predictable direction of expansion, e.g., to deflect upwardly and slightly outwardly. This also decreases the amount of force required to initiate the bending. Such flattened portion can also be used with the retractor elements of the other embodiments disclosed herein.

The retractor system 1150 can be configured to reversibly stiffen an otherwise flexible arrangement of the retractor 1150. In this regard, retractor system 1150 can include a substantially-rigid beam to support the expanded retractor 1150 which helps to create a more stabilized chamber (or cage) as described herein. With reference to FIGS. 15 and 17A, a flexible tube or beam 1160 is provided in the collapsed configuration, whereas in FIG. 17B, the retractor system has a rigid beam that is formed from the flexible beam 1160. More specifically, in this embodiment, the flexible beam 1160 is in the form of a rod or tube 1165 having a lumen to slidably receive therein a stabilizing or rigidifying structure such as a rigid tube or rod (beam) 1162. The rigidifying (stabilizing) structure 1162 is independently actuated by the user by movement of actuator 1134. Actuator 1134 is slidably mounted within a longitudinally extending slot of housing 1130. In the initial position of FIG. 17A, rigidifying structure 1162 is retracted within a lumen of the catheter and either not engaged, or only partially engaged, with flexible tube (or rod) 1160. Rigidifying structure 1162 attached at its proximal end to sliding block 1164 which is operably connected to actuator 1134. To rigidify tube 1160, actuator 1134 is slid distally to the position of FIG. 17B, thereby advancing sliding block 1164 and the attached stabilizing structure 1162 distally. Such movement advances the rigidifying structure 1162 through the lumen 1165 of the flexible tube 1160 to the distal end 1160a to thereby stiffen the beam. The rigidifying structure 1162 can optionally be removed from the flexible beam 1060 to return the system back to the original more flexible state to aid collapsing of the retractor system 1050 by sliding the actuator 1134 in the reverse direction (proximally) within the axial slot, thereby withdrawing rigidifying structure 1162 from the advanced position within flexible tube 1160. In one embodiment, the rigidifying structure 1162 is in the form of a structure having a proximal and distal metal tubular structure joined by a flexible braid polyimide tube. However, it should be appreciated that other structures are also contemplated. Note the structures 1160, 1162 can be substantially circular in cross-section, although other cross-sectional shapes are also contemplated. As in the aforedescribed embodiments, the rigid beam limits deflection of the distal end 1111 of the catheter 1110 which could otherwise occur by pressure exerted on the distal end by the body lumen wall.

As shown in FIGS. 17A and 17B, the actuator can include a connector 1135 having a tooth or pawl 1137 to engage a tooth on the rack 1138 positioned within housing 1130 to retain the rigidifying structure 1164 in one of several selected positions.

Figure 17C:
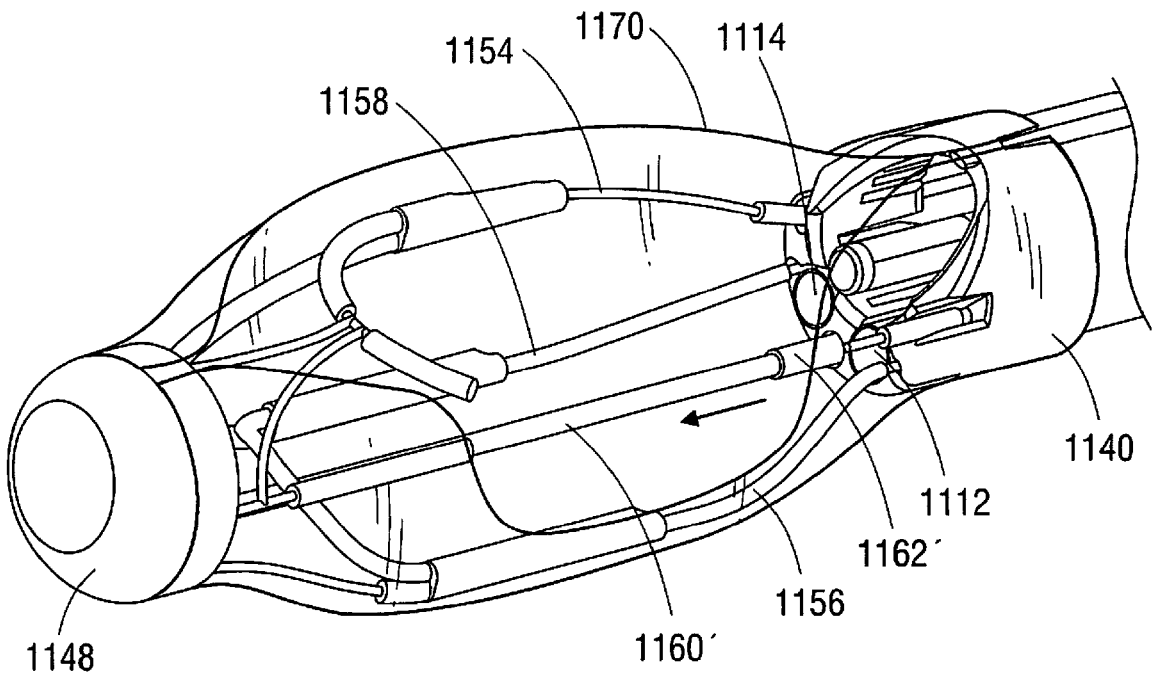
FIG. 17C is a perspective view similar to FIG. 15 showing an alternate embodiment of the rigidifying structure.
Figure 17D:
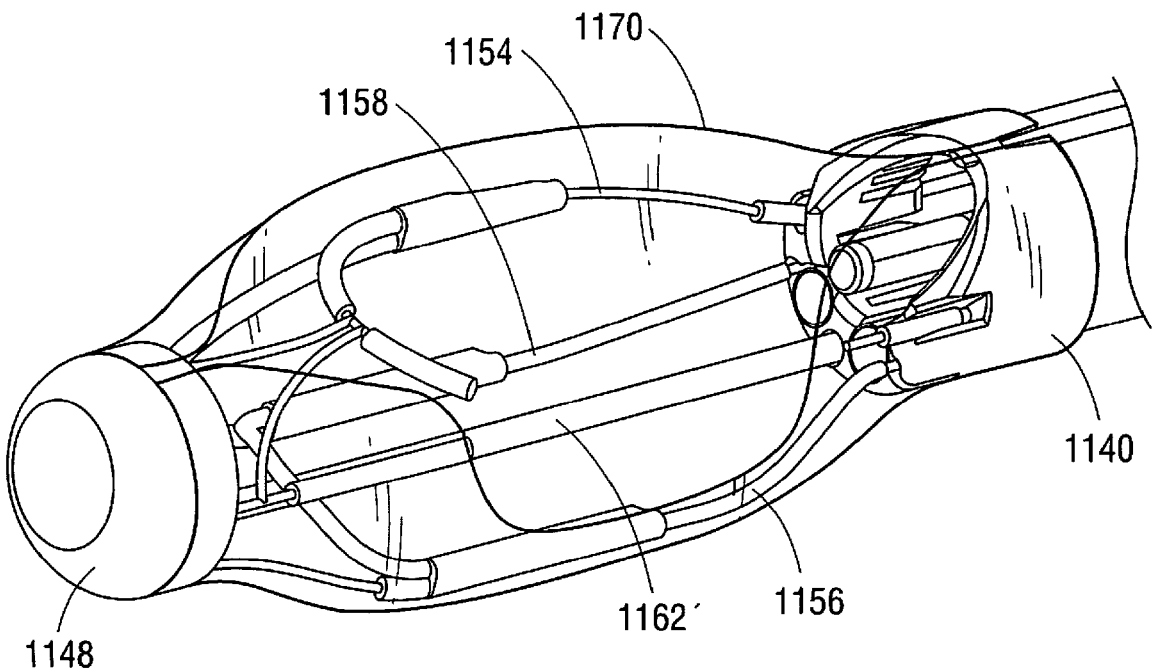
FIG. 17D is a perspective view similar to FIG. 17C showing the rigidifying structure of FIG. 17C advanced over the flexible element.
Figure 18:
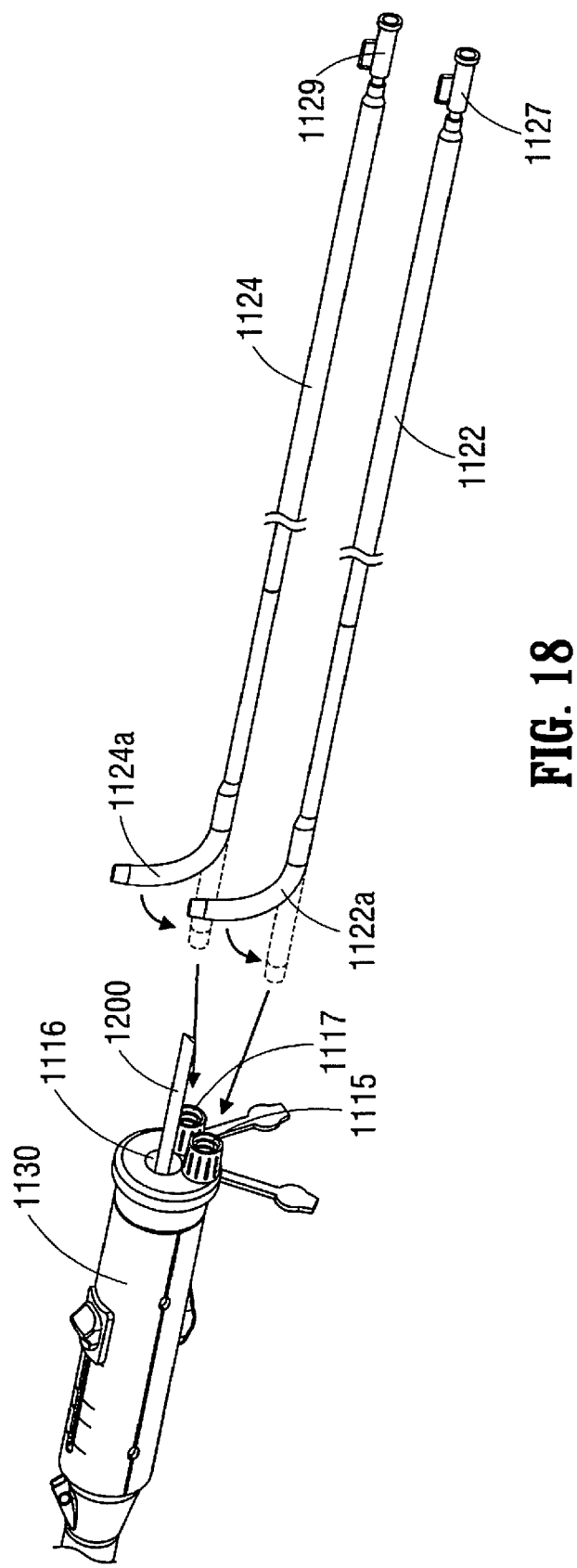
FIG. 18 is a perspective view showing the two tool channels (guides) adjacent the proximal end of the catheter of FIG. 11 for insertion therethrough.

In the alternate embodiment of FIGS. 17C and 17D, instead of advancing a rigidifying structure within the lumen of the flexible element, the rigidifying structure is advanced over the flexible element. More specifically, flexible beam 1160' is rigidified by movement of a rigidifying structure, e.g., tubular member 1162', over the flexible beam 1160'. That is, rigidifying member 1162' has a lumen configured and dimensioned to receive flexible beam 1160' as it is passed thereover in the direction of the arrow of FIG. 17C. Note that flexible element 1152 has been removed from FIGS. 17C and 17D for clarity. Actuator 1134, as well as alternative methods, can be utilized for such movement.

A covering or cover 1170 is preferably provided at a distal end of the catheter 1110. Covering 1170 in the illustrated embodiment is mounted around the perimeter of the proximal coupler 1140 and the distal coupler 1148. In some embodiments, the cover 1170 is pleated and sealed around the couplers (caps) 1140, 1148 by a heat shrink wrap. The cover 1170 is positioned around the elements 1152, 1154, 1156, 1158 in the collapsed insertion position, with an opening in the cover 1170 facing toward the target tissue, e.g., the lesion to be removed. That is, in the orientation of FIG. 15, the opening in cover 1170 faces upwardly. The cover 1170 can be configured to have an opening in the collapsed position, or, alternatively, it can provided with a slit which can be opened due to stretching when the retractor elements 1152, 1154 are moved to the expanded position. When the retractor elements 1152, 1154 are expanded, they move past the cover 1170 toward the target tissue. Alternatively, the edges of the cover 1170 can be attached to the retractor elements 1152, 1154 and thereby move with the retractor elements. When the target tissue is removed by the endoscopic instruments described herein, the removed tissue is placed within the cover 1170, and the cover 1170 is closed, e.g., by a string or suture 1172 shown in FIG. 29 to encapsulate the tissue and prevent leakage and seeding during removal from the body lumen. The suture 1172 can be embedded in a wall of the cover 1170 or in pockets or channels formed in the cover 1170, where it is permanently fixed at a distal anchor point, and pulled proximally to tension the suture 1172 and close the cover 1170.

As with the cover (sheath) 1000 of FIG. 10, the cover 1170 by covering the retractor elements 1152, 1154, 1156, 1158 can provide a smooth and atraumatic surface for the delivery of the retractor system to the target site. The cover 1170, like cover 1000, also helps to prevent tissue, e.g. the luminal walls, from entering through the spaces between the beam 1160 and elements 1156, 1158 during the surgical procedure.

In a preferred embodiment, the two ends of suture 1172 extend out of tubing 1139. Their proximal ends can be covered by a length of tubing to facilitate grasping by the user. The suture 1172 extends through switch 1137 and tubing 1139, through a dedicated lumen (channel) in the catheter, through the covering 1170, and is looped at the distal cap 1148 where it is attached (anchored). During the procedure, the suture 1172 remains untensioned. After the tissue is placed within the cover (bag) 1170, the two proximal ends of the looped suture 1172 are pulled proximally to tension the suture 1172 to close the cover 1170. The switch can then be moved to frictionally engage to the suture 1172 to secure it so it locks in the tensioned position to maintain closure of the cover 1170.

The use of the system of FIG. 11 will now be described with reference to removing a lesion, such as a polyp, from a colon wall, it being understood, however, that the system 1100 can used for other procedures within the colon or the gastrointestinal tract, as well as used for other procedures in other body lumens or body spaces of a patient.

Figure 13:
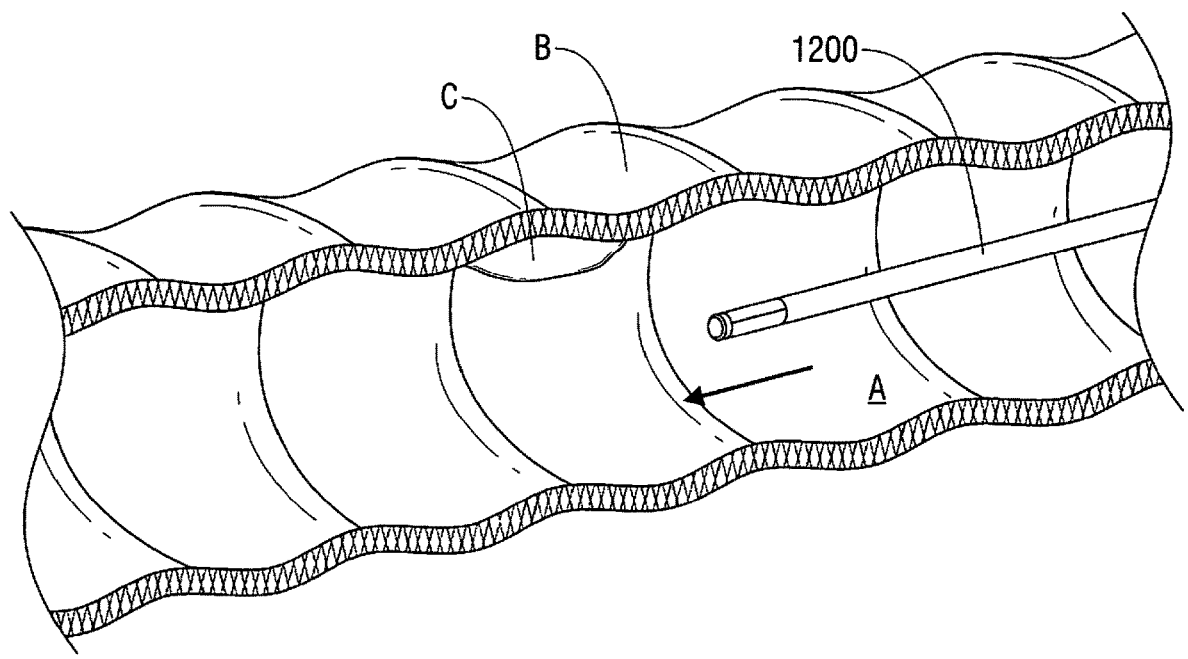
FIG. 13 illustrates insertion of the endoscope through the colon.
Figure 14:
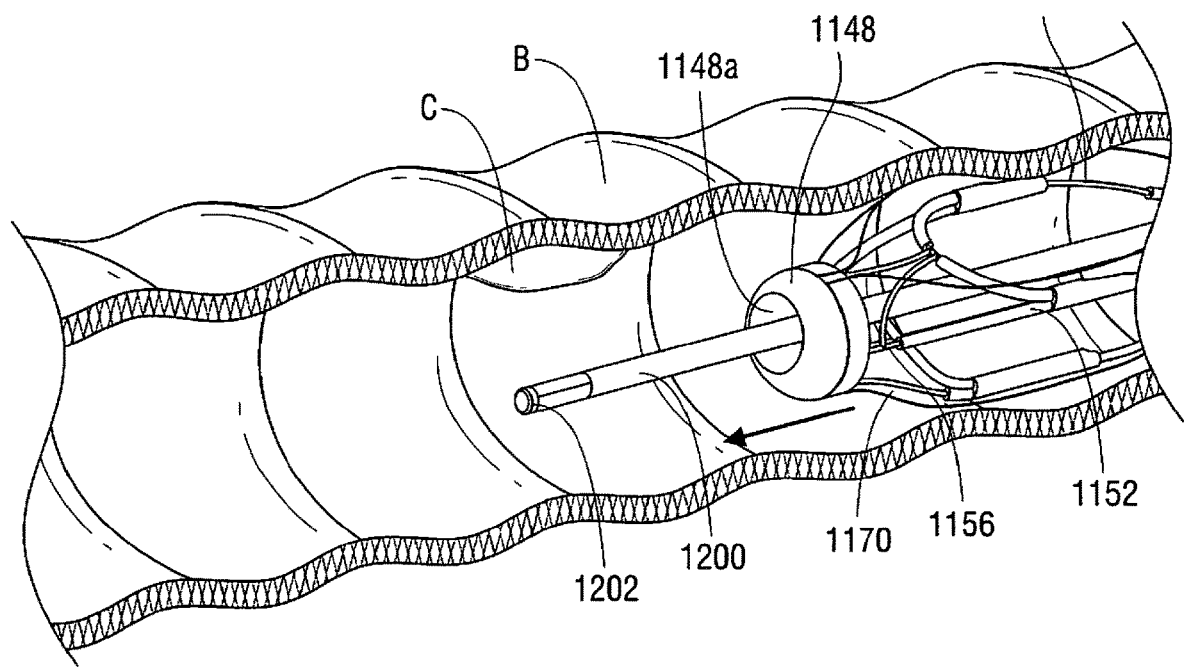
FIG. 14 is a perspective view showing the catheter of FIG. 11 being further advanced over the endoscope of FIG. 13, the retractor system shown in the collapsed position.

Turning first to FIGS. 12 and 13, a distal viewing endoscope 1200, in which the system 1100 has been advanced over the proximal end 1201 as shown in FIG. 12, or alternatively the system 1100 backloaded over the distal end of the endoscope 1200, is inserted through lumen A in the colon B in a procedure to remove the target polyp C from the wall of the colon B. The endoscope 1200 in this embodiment is a distal viewing scope with a wide distal viewing area of about 150-170 degree range so the polyp C and surrounding area can be visualized. After placement of the scope 1200 adjacent the target issue, i.e., slightly proximal of the target polyp C, the system 1100 is further advanced over the endoscope 1200. Distal coupler (cap) 1148 has an opening 1148a, and proximal coupler (cap) 1140 has an opening communicating with the lumen 1116 (FIG. 16) of the catheter 1110 to enable such backloading of the endoscope 1200 and advancement of the system 1100 thereover. The catheter 1110 is advanced over the endoscope 1200 as shown in FIG. 14 until it reaches the target site as shown in FIG. 15, with the retractor system 1050 aligned with the polyp C. As can be appreciated, in this insertion position of the catheter 1110, the retractor system 1150 is in the non-expanded (or collapsed) position, with retractor elements 1152, 1154, preferably not exceeding, or only slightly exceeding, the transverse dimension of the catheter 1110. In this position, the retractor elements, or at least retractor elements 1156, 1158, are covered by the covering 1170. As shown, in this position, the distal end 1202 of the endoscope 1200 is preferably positioned at the end of proximal coupler 1140 and does not extend into the working space 1151 to thereby leave more room for maneuvering of the endoscopic instruments within the working space. Other positions, however, are also contemplated, e.g., in some versions the endoscope can extend into the working space 1151. Note also in this insertion position, actuators 1134 and 1132 are in their retracted position as shown in FIG. 16.

Next, to rigidify the retractor system 1150, the actuator 1134 is moved distally from the position of FIG. 17A to the position of FIG. 17B (see also the arrow in FIG. 16) to advance rigidifying structure 1162 from the retracted position to an advanced position within lumen 1165 of flexible tube 1160. This stiffens/stabilizes the retractor system 1150 as discussed above. Note, as discussed above, the retractor system 1150 can alternatively be stiffened/stabilized by advancement of a rigidifying structure over the flexible element as shown in FIGS. 17C and 17D.

The retractor system 1150 is now expanded. Actuator 1132 is advanced distally from the position of FIG. 20A to the position of FIG. 20B (see also FIG. 19). This advances block 1146 (which is operably coupled to retractor elements 1152 and 1154 as discussed above) which forces retractor elements 1152, 1154 laterally outwardly to the position of FIG. 20B, thereby creating the asymmetric working space (chamber) as described in detail above.

Figure 21B:
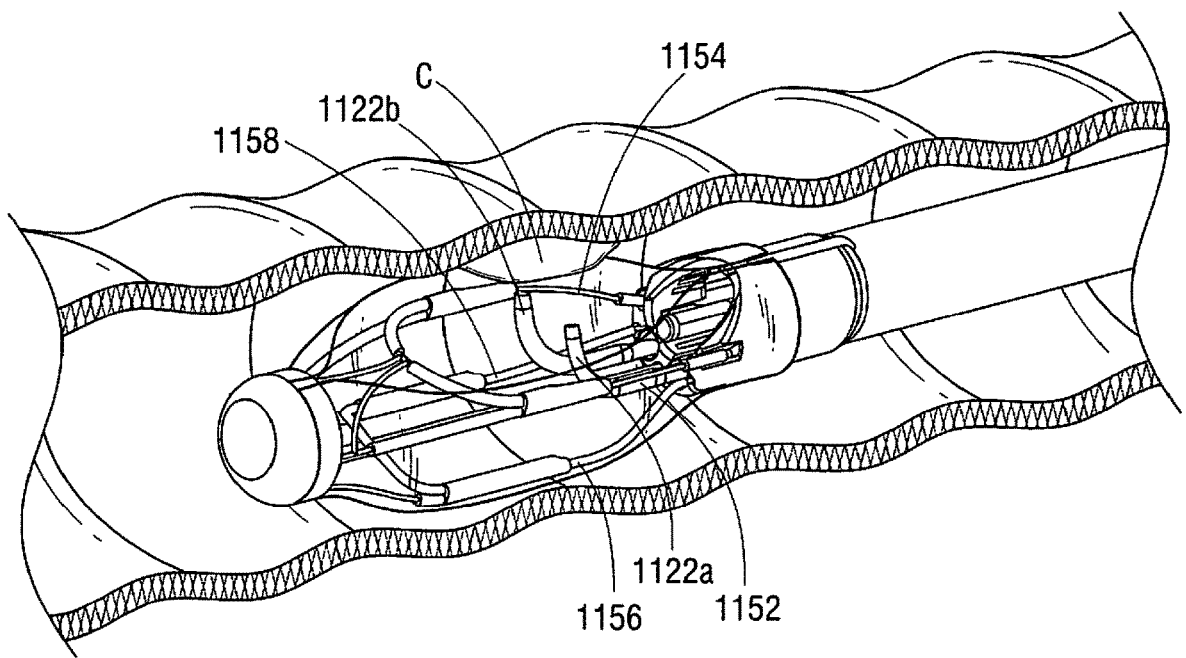
FIG. 21B is a view similar to FIG. 21A illustrating an alternate embodiment wherein the tool channels are advanced from the catheter prior to expansion of the retractor system.

Next, tool channels 1122, 1124 are inserted through the ports 1115, 1117 in the proximal region of the catheter 1110 (see FIG. 19A) and advanced by the user through the catheter lumens 1112, 1114 so they extend out the distal openings of the lumens 1112, 1114 and into the chamber 1151 as shown in FIG. 21A. Note as they emerge from the lumens 1112, 114, and out of the confines of the lumen walls of the catheter 1110, their distal tips 1122a, 1124a return to their curved (bent) position, curving upwardly (as viewed in the orientation of FIG. 21A) toward the polyp C. Note in FIG. 21A, the retractor elements are first expanded, followed by insertion of the tool channels 1122, 1124 out of the catheter lumens 1112, 1114 and into the working space 1151. However, it is also contemplated that in an alternative embodiment, the tool channels 1122, 1124 can be inserted through the catheter lumens 1112, 1114 and into the working space 1151 prior to expansion of the retractor elements 1152, 1154. This alternate method is shown in FIG. 21B, with the tool channel tips 1122a, 1122b exposed, but the retractor system 1150 still in the non-expanded position. Note the tool channels 1122, 1124 can be independently rotated and/or moved axially to adjust their position with respect to the polyp C. As can be appreciated, the terms upwardly and downwardly as used herein refer to the orientation of the system in the referenced Figures. If the position of the system changes, the orientation and terms would also change.

Figure 22:
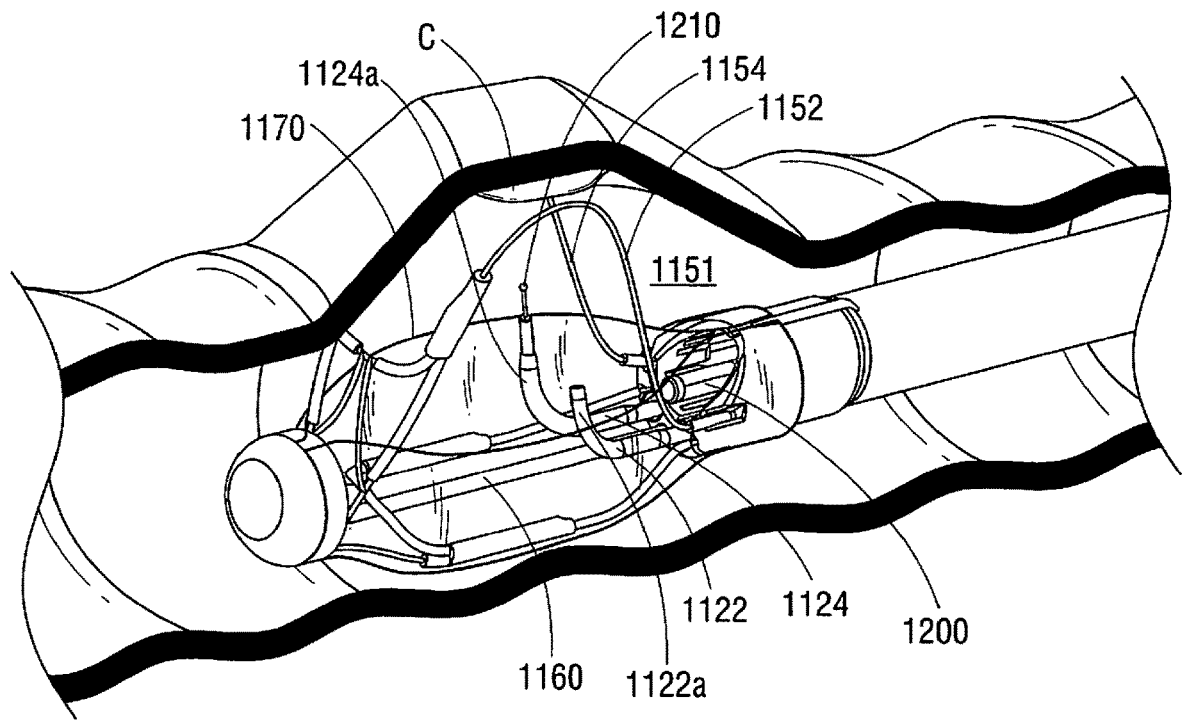
FIG. 22 is a view similar to FIG. 21A showing a first endoscopic instrument (tool) advanced from a first tool channel.
Figure 23:
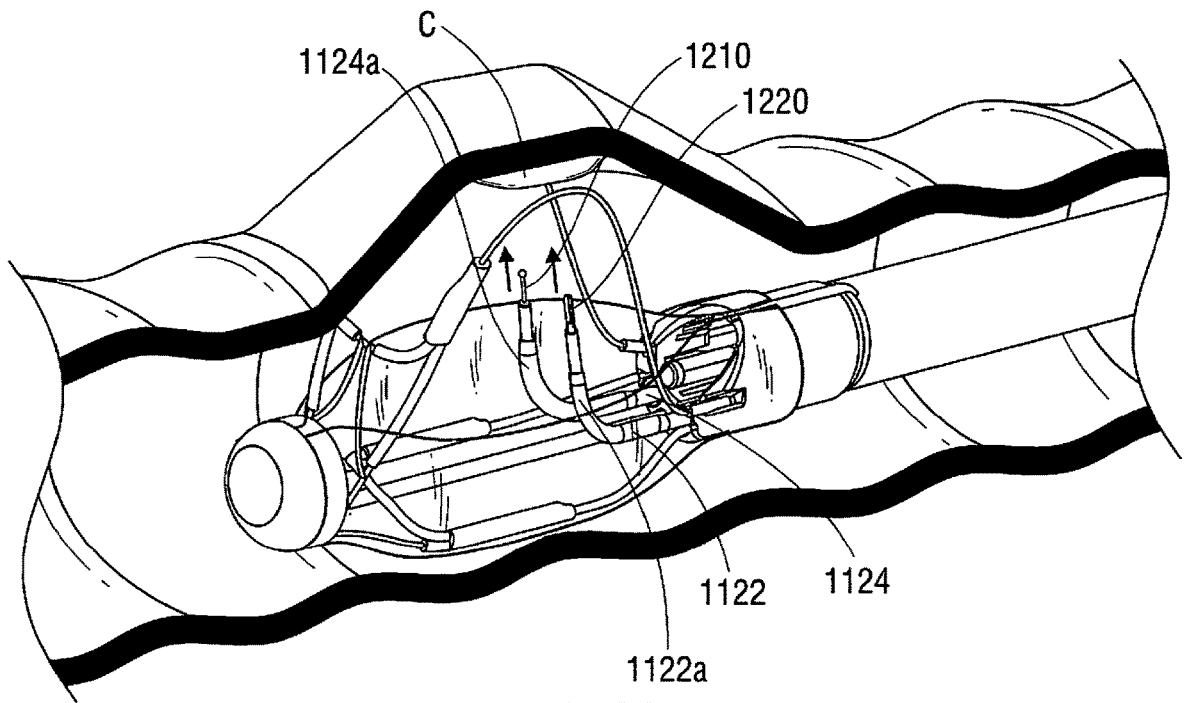
FIG. 23 is a view similar to FIG. 22 showing a second endoscopic instrument (tool) advanced from a second tool channel.
Figure 24:
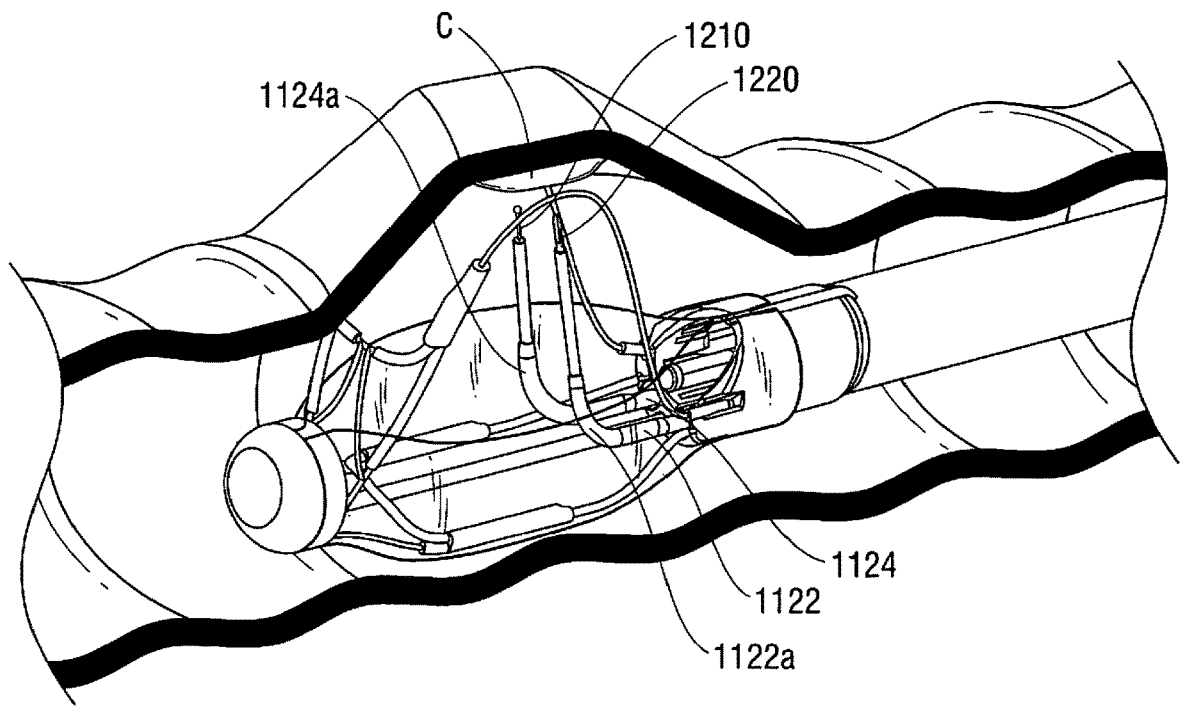
FIG. 24 is a view similar to FIG. 23 showing both endoscopic instruments further advanced from the tool channels.
Figure 25:
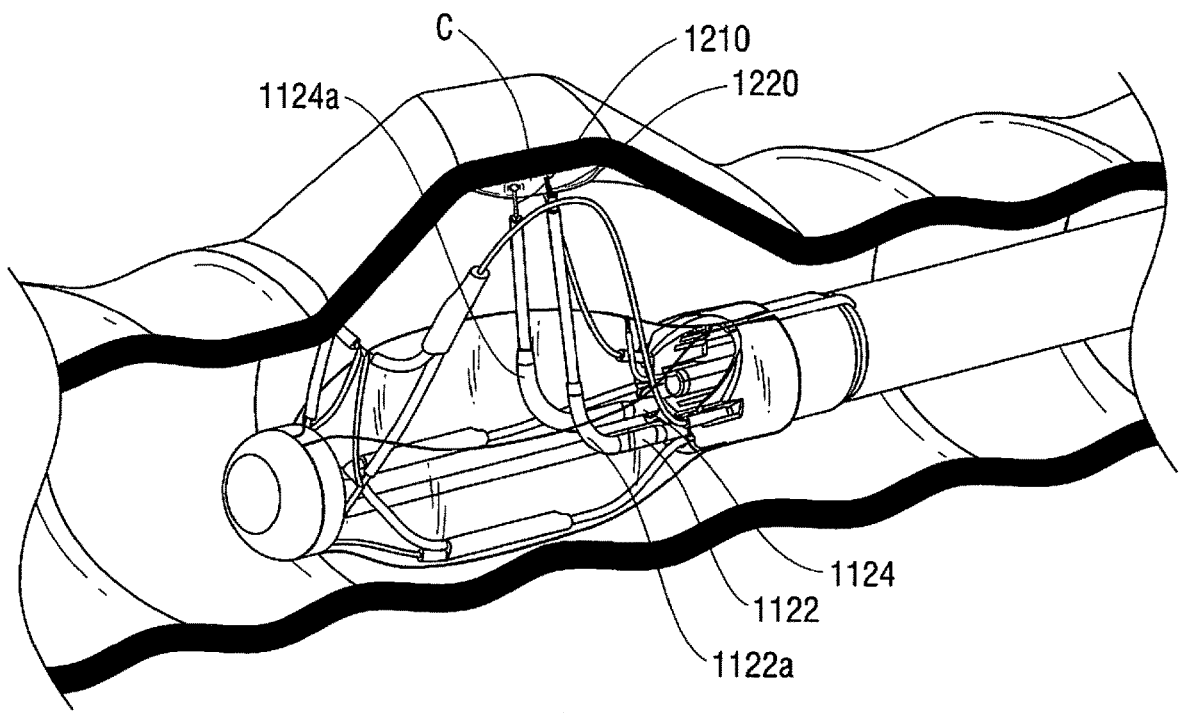
FIG. 25 is a view similar to FIG. 24 showing the endoscopic instruments further advanced from the tool channels to dissect the lesion on the colon wall.

After insertion of the tool channels 1122, 1124, endoscopic instrument (tool) 1210 is inserted through the luer fitting 1129 (FIG. 19A) of the tool channel 1124 and advanced through the lumen (channel) of the tool channel. As shown in FIG. 22, a first endoscopic instrument 1210 extends from tool channel 1124 and follows the curve of the tool channel 1124. A second endoscopic instrument (tool) 1220 is inserted through the luer fitting 1127 of tool channel 1122 and advanced through the lumen of the tool channel 1122. As shown in FIG. 23, the second endoscopic instrument follows the curve of the tool channel 1122. As noted above, the tool channels can include a valve, such as the hemostatic valves as shown in FIG. 19B, so insufflation is not lost during insertion and removal of the endoscopic instruments from the tool channels. The endoscopic instruments 1210, 1220 can be moved further axially as shown in FIGS. 24 and 25 to extend further from the tool channels 1122, 1124 to contact and treat, e.g., remove, the polyp C. This movement of the endoscopic instruments shown by comparing FIGS. 23-25 shows the advantage of the tool channels 1122, 1124. As can be seen, once the tool channels 1122, 1124 are in the desired position with respect to the polyp C, they can be considered as defining a fixed curve. This means that when the endoscopic instruments 1210, 1220 are axially advanced, they move closer to the target polyp C, without a change in curvature and without a change in their axial position with respect to the polyp C, thus providing an extra degree of freedom. The endoscopic instrument 1210, which in the illustrated embodiment is a grasper, applies tension on the polyp C while the electrosurgical dissector 1180 dissects/severs the polyp C from the colon wall B. Other endoscopic instruments for polyp removal can also be utilized. Additionally, in some embodiments, a single tool channel can be utilized and another endoscopic instrument, e.g., a grasper or a dissector, can be inserted through a working channel (lumen) of the endoscope. Such instrumentation inserted through an endoscope can also be utilized with the embodiments having two or more tool channels.

Figure 30:
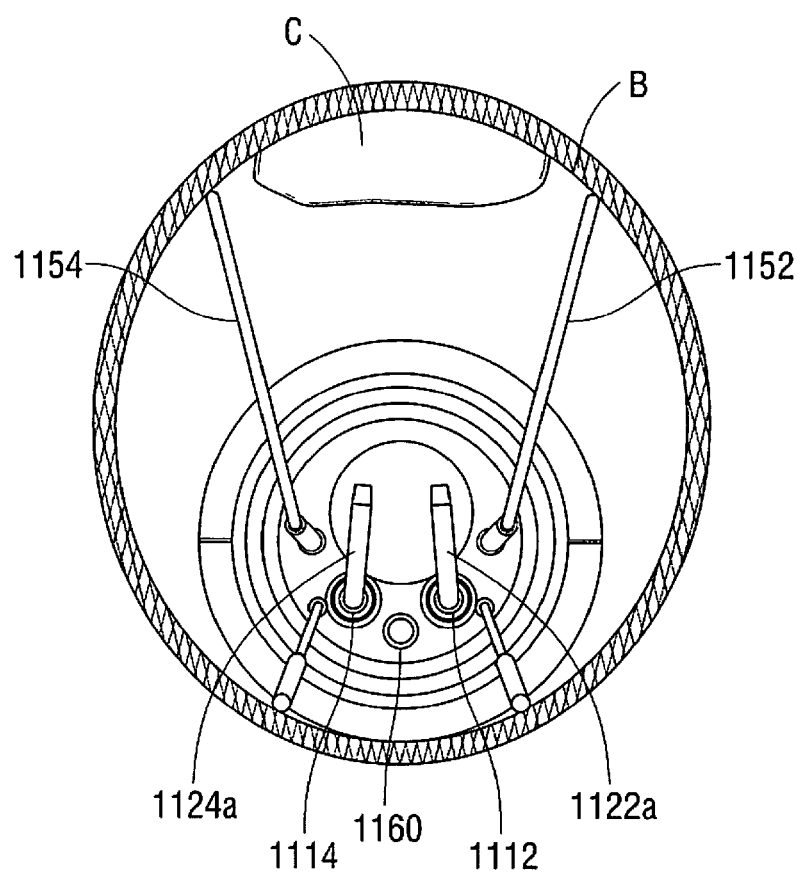
FIG. 30 is a front view of the system in the expanded position of the retractor system and showing two tool channels extending from the catheter.

Also note that due to the angles of the tool channels 1122, 1124 and thus the endoscopic instruments inserted therethrough, tissue triangulation can be achieved as depicted by the dotted lines in FIG. 30.

Figure 26:
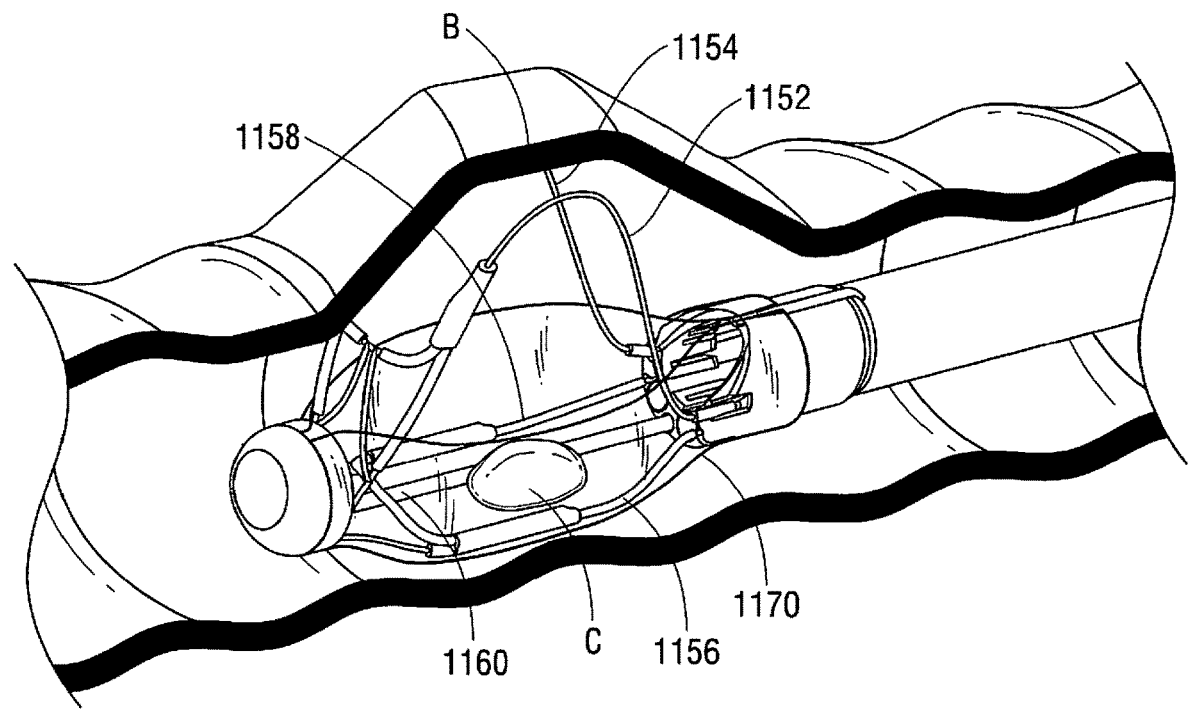
FIG. 26 is a view similar to FIG. 25 showing the lesion which has been removed from the colon wall by the dissecting instrument placed within the retractor system.
Figure 27:
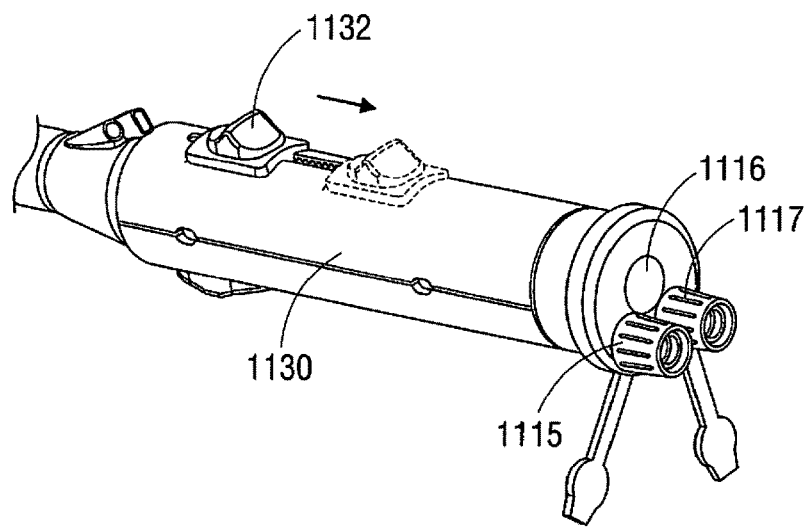
FIG. 27 is a perspective view of the proximal end of the catheter showing proximal movement of the actuator to return the retractor system to the collapsed position for removal from the colon.

After removal of the polyp C from the colon wall B, it is placed within the cover 1170 as shown in FIG. 26, ready for removal from the body. Actuator 1134 can be moved proximally to return the retractor system to the more flexible condition if desired. Actuator 1132 is moved proximally in the direction of the arrow of FIG. 27 to return the expanded retractor elements 1152, 1154 to their collapsed position of FIG. 28 for removal of the catheter 1110. The string or suture 1172 is then tensioned to close the cover (bag) 1170 as shown in FIG. 29, forming a bag to encapsulate the polyp C. The switch 1175 can then be moved to the position of FIG. 31B to lock the string 1172 and thereby maintain the cover 1170 in the closed position. Catheter 1110 is then removed from the colon B with the polyp C protected (encapsulated) within the cover 1170. Note that the cover 1170 is preferably transparent so that the drawings illustrate the retractor elements, bridge members, beam, etc. However, to facilitate understanding of the cover 1170, FIG. 29 shows the retractor elements, bridge elements, beam etc. in phantom insider the bag/cover 1170.

FIGS. 32-42 illustrate alternative embodiments of the system of the present invention. The system includes floating (flexible) channels within the outer tube. In one embodiment, the floating channels are fixed at their proximal and distal ends; in another embodiment the floating channels are fixed at their proximal ends but are unattached at their distal ends. As can be appreciated from the discussion below, the floating channels reduce the overall stiffness of the catheter (outer tube) which would otherwise be stiffer if the channels were fixed along their entire length and did not float within the catheter. The floating channels also reduce kinking of the tool channels {flexible guides) inserted through the floating channels and reduce kinking of the tools inserted through the tool channels (or inserted directly through the floating channels in the embodiments where the tool channels are not utilized).

Figure 32:
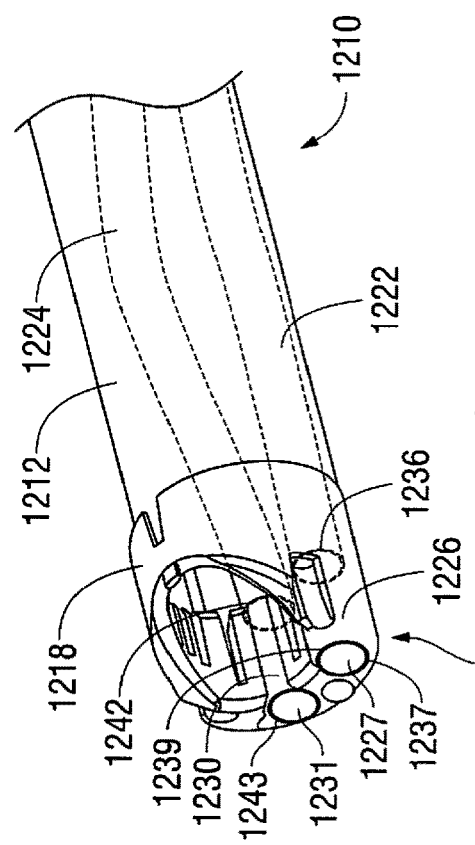
FIG. 32 is a perspective view of the distal end of the outer tube (catheter) of an alternate embodiment of the system showing two floating channels therein.
Figure 33:
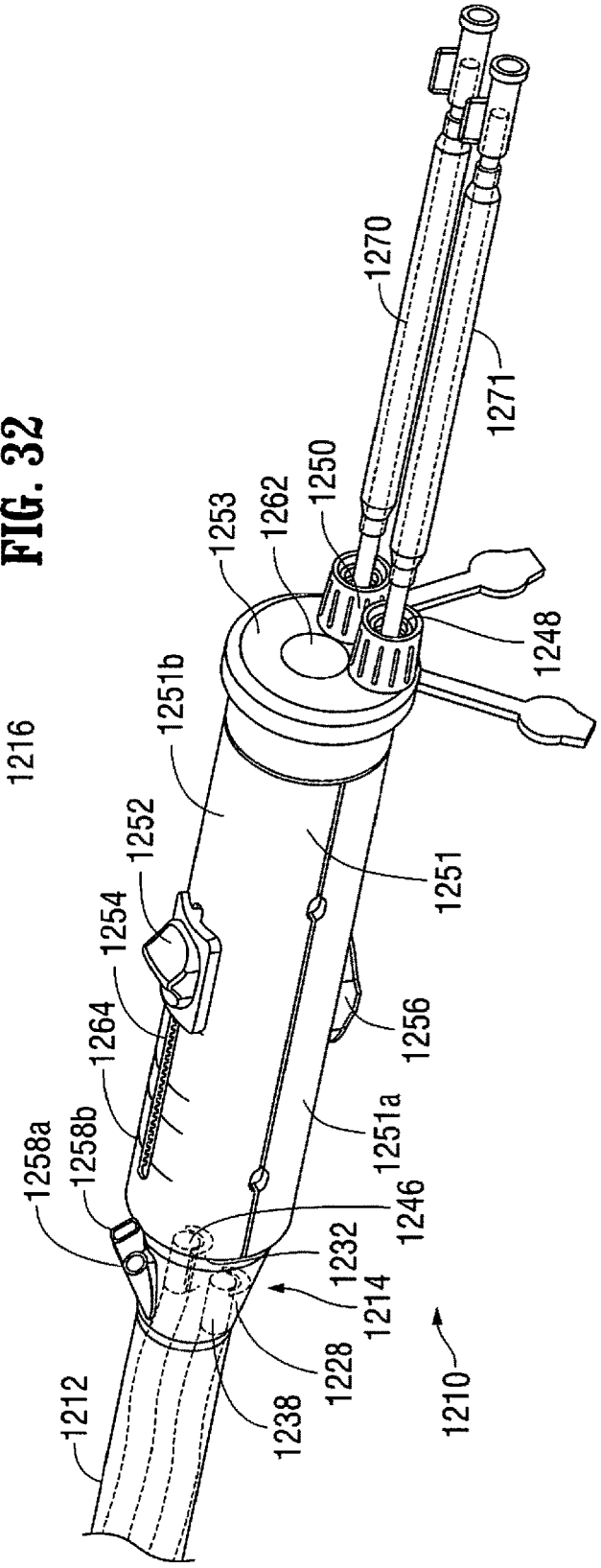
FIG. 33 is a perspective view of a proximal portion of the system of FIG. 32.
Figure 34:
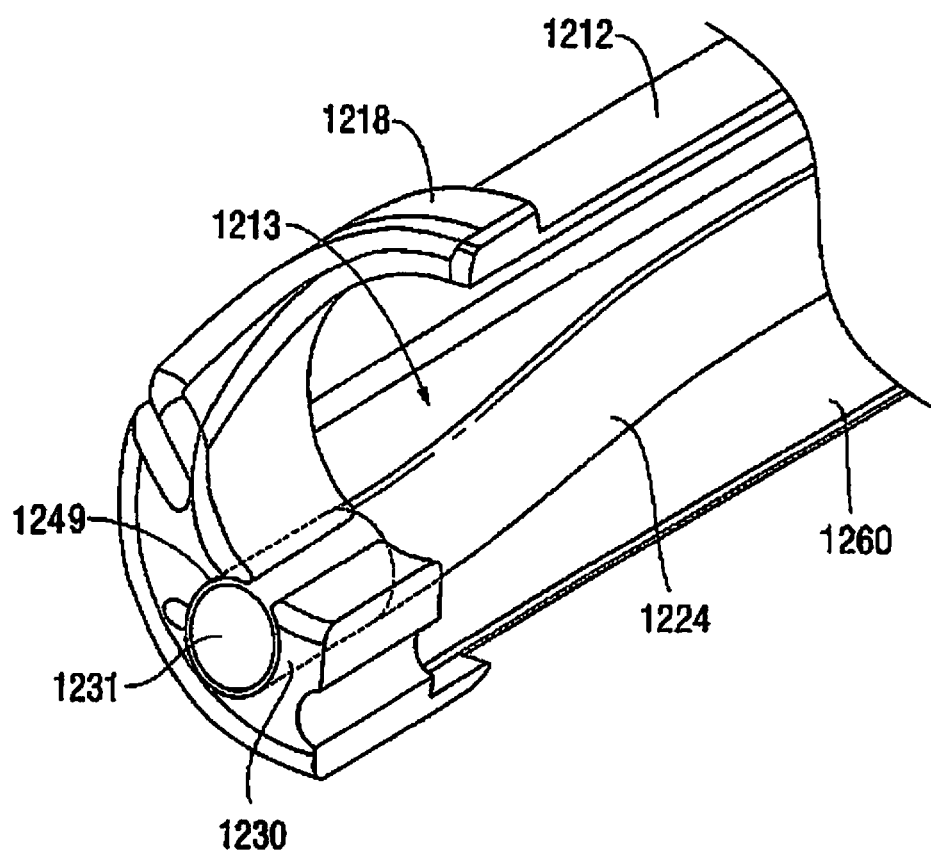
FIG. 34 is a close up cutaway view showing one of the floating channels of FIG. 32.

More specifically, in the embodiment shown in FIGS. 32-34, the system 1210
includes a flexible catheter or outer tubular member (main tube) 1212. The proximal portion of the outer tube 1212 is designated generally by reference numeral 1214 and the distal portion is designated generally by reference numeral 1216. A proximal end cap 1218 is positioned over distal portion 1216 of outer tubular member 1212.

A handle housing 1251 similar to handle housing 1130 of FIG. 11 described above is composed of two half shells 1251*a*, 1251*b* attached together. Shell 1251*b* has an actuator 1252 in the form of a sliding button, although other forms of actuators can be provided. Actuator 1252 is connected to cage wire push tubes, such as push tubes 1428, 1430 of FIGS. 40 and 42 described below, extending through outer tube 1212. Distal movement of the actuator 1252 along slot 1254 causes distal movement of the push tubes 1428, 1430 which causes the flexible elements of the cage to bow outwardly as described below. At the distal end of the handle housing 1251 are access ports 1258*a*, 1258*b* for inflow tubes (not shown) which can be part of a member (organizer) secured within the handle housing 1251 at a proximal region. At the proximal end of the handle housing 1251 is a handle end cap 1253 with an opening 1262 for entry of an endoscope into the outer tube 1212. Ports 1248, 1250 extend from proximal end cap 1253 to provide entry for the tool channels (flexible guides) 1270, 1271. The ports 1248, 1250 preferably include a valve to maintain insufflation when the tool channels 1270, 1271 are inserted therethrough and translated axially therein. Markings 1264 can be provided on the handle housing 1251 to indicate to the user the extent of distal travel of the actuator 1252 to control the size of the expanded cage. For example, the markings provided can be "4, 5 and 6" to indicate expansion of the cage to 4, 5 or 6 centimeters, providing the user with a general indication of the incremental expanded positions. Other markings and/or extent of expansions are also contemplated. The actuator 1252 can have a plurality of teeth or other retention structure to retain the actuator 1252 and thus the retractor elements in select extended positions.

Actuator 1256 on shell 1251*a* provides for rigidifying the cage by rigidifying a flexible beam. As described below, in alternate embodiments, a separate slidable beam for rigidifying the cage is not provided as alternative rigidifying structure is provided. As in the embodiment of FIGS. 17A and 17B, in this embodiment of FIG. 33, a stiffener member in the form of a rigid beam is operatively connected to actuator 1256 so that distal movement of the actuator 1256 advances the stiffener distally either within a lumen of the flexible element or over the outer surface of the flexible element to provide a stiffer structure. Actuator 1256 can be moved proximally to unstiffen the flexible element to facilitate collapse of the retractor system.

With reference to the cross-sectional view of FIG. 37A, the outer tube (catheter) 1212 in this embodiment has a single lumen 1213. This lumen 1213 is dimensioned to receive 1) an endoscope 1200, such as the endoscopes described above; and 2) two flexible channels 1222, 1224. The two flexible channels 1222, 1224 are in the form of flexible tubes and float inside the lumen 1213. That is, the two floating channels 1222, 1224 have intermediate portions that can move radially (laterally) within the lumen 1213 of the outer tube 1212. Stated another way, the floating channels 1222, 1224 are unconstrained within the outer tube 1212 so they can bend relative to the outer tube 1212 so their bending action does not need to follow that of the outer tube 1212. In this manner, when the outer tube 1212 is inserted in the body lumen and needs to bend to accommodate the curvatures of the body lumen, e.g., the gastrointestinal tract, the flexibility of the outer tube 1212 is maintained since the floating channels 1222, 1224 can move within the lumen 1213. As can be appreciated, if the two channels were fixed with respect to the outer tube 1212 so there was no bending or movement with respect to the outer tube 1212, and the channels were forced to bend in conformity with the outer tube 1212, the outer tube 1212 would be much stiffer as the channels would have to carry the bending stresses which could limit bending of the catheter and/or cause kinking of the tool channels or tools extending through the channels of the catheter. Thus, in the embodiments of the present invention which include the floating channels, these advantages of increased flexibility are achieved. It should be understood that any of the systems disclosed herein could be provided with floating channels. Likewise, any of the systems disclosed herein could be provided without floating channels. FIG. 37B provides by way of example a location of the floating channels 1222, 1224 when they are moved within the catheter 1212 as it is bent. Clearly, floating channels 1222, 1224 will move to various other positions in response to catheter bending.

Also, by providing a single lumen in this embodiment to receive the endoscope and the tool channels, rather than separate lumens which would require additional wall structure, a smaller diameter catheter can be provided which also reduces the overall stiffness of the catheter.

The endoscope 1200 in the embodiment of FIG. 37A also floats within the lumen 1213. That is, the endoscope occupies only a certain region of the lumen 1213 and can move radially (laterally) within the lumen 1213 of outer tube 1212 to increase the flexibility of the system. Thus, the endoscope 1200 can move relative to the outer tube 1212 in a similar manner as the floating channels 1222, 1224 can move relative to the outer tube 1212.

In one embodiment by way of example, the internal diameter of the lumen 1213 of the outer tube 1212 ranges between about 5 mm and about 50 mm and is preferably about 10 mm to about 20 mm. Each of the floating channels preferably has an outer diameter of about 2 mm to about 10 mm, and preferably about 5 mm. The endoscope typically has a diameter of about 2 mm to about 20 mm and is preferably about 5 mm to about 12 mm. Thus, as can be appreciated, the floating channels and endoscope occupy only a small percentage of the internal lumen 1213, leaving sufficient room for movement. Note that other dimensions and thus ratios of the floating channels and endoscope to the internal diameter of the lumen 1213 are also contemplated for the systems disclosed herein.

In one embodiment, by way of example, the outer tube 1212 has a length, measured from the distal end of handle 1251 to a distal edge of end cap 1218 of about 10 cm to about 200 cm, and more preferably about 60 cm to about 90 cm. The floating channels 1222, 1224 have a length of about 10.1 cm to about 204 cm, and preferably about 60.5 cm to about 91 cm, thereby exceeding the length of the outer tube 1212. Other dimensions are also contemplated. This greater length of the floating channels 1222, 1224 in the embodiments where they are fixed at both the proximal and distal ends enables the floating movement.

Turning now to details of the floating channels and their securement within outer tube 1212, in the embodiment of FIGS. 32-34, channel 1222, referred to herein as a first flexible channel or a first floating channel or a first flexible tube, has a proximal end 1238 and an opposing distal end 1239. Channel 1224, referred to herein as a second flexible channel or a second floating channel or a second flexible tube, has a proximal end 1246 and an opposing distal end 1249. Note the terms "first" and "second" to describe various components of the systems of the present invention are used herein for ease of description. Note in the embodiments of FIGS. 32-42, two floating channels are provided. It is also contemplated that only one floating channel is provided or more than two floating channels are provided.

Positioned with the outer tube 1212 at a distal end is a first fixed distal tube 1226 which forms a pocket for the first floating channel 1222. First distal tube 1226 has an opening 1227, a proximal edge 1236 and a distal edge 1237. In some embodiments, instead of an opening 1227 the distal end can be closed. Preferably, distal edge 1237 is substantially flush with the distal edge of distal end cap 1218. At the proximal end of the system, positioned either within the outer tube 1212 or alternatively at a distal region of the handle housing 1251, is a first fixed proximal tube 1228.

Also positioned with the outer tube 1212 at a distal end is a second fixed distal tube 1230 which forms a pocket for the second floating channel 1224. Distal tube 1230 has an opening 1231, a proximal edge 1242 and a distal edge 1243. In some embodiments, instead of an opening 1231 the distal end can be closed. Preferably, distal edge 1243 is substantially flush with the distal edge of distal end cap 1218. At the proximal end of the system. positioned either within the outer tube 1212 or alternatively at a distal region of the handle housing 1251, is a second fixed proximal tube 1232 having a proximal edge 1246. The first and second proximal tubes 1228, 1232 are preferably attached to an inner wall of the outer tube 1212 or handle housing 1251 by bonding or welding or other attachment methods. Similarly, the first and second distal tubes 1226, 1230 are preferably attached to an inner wall of the outer tube 1212 by bonding or welding or other attachment methods. Note in FIG. 33, the fixed proximal tubes 1228 or 1232 are shown cutaway (into a half cylinder) for clarity, it being understood that the tubes can be cylindrical in configuration like the distal fixed tubes 1226. 1230. Other configurations for the fixed distal and proximal tubes are contemplated.

The distal end of the first flexible channel (tube) 1222 is positioned within the first fixed distal tube 1226 and secured ttlereto such as by bonding or welding or other attachment methods. It can terminate in any fixed position within the distal tube 1226, and in the illustrated embodiment, terminates at the distal end of the distal tube 1226. The proximal end 1238 of first flexible channel 1222 is positioned within the first fixed proximal tube 1228 and secured thereto such as by bonding or welding or other attachment methods. It can terminate in any fixed position within the proximal tube 1228, and in the illustrated embodiment, terminates at ttle proximal end of the proximal tube 1228. In this manner, the first flexible channel 1222 is fixed with respect to the outer tube 1212 at its proximal end and at its distal end. However, it remains unattached in an intermediate portion between the proximal and distal end, e.g., along its length between its t¹No fixed ends, so it can float within the outer tube 1212. Similarly, the distal end of the second flexible channel (tube) 1224 is positioned within the second fixed distal tube 1230 and secured thereto such as by bonding or welding or other attachment methods. It can terminate in any fixed position within the distal tube 1230, and in the illustrated embodiment, terminates at the distal end of the distal tube 1230. The proximal end of second flexible channel 1224 is positioned within the second fixed proximal tube 1232 and secured thereto such as by bonding or welding or other attachment methods. It can terminate in any fixed position within the proximal tube 1232, and in the illustrated embodiment, terminates at the proximal end of the proximal tube 1232. In this manner, the second flexible channel 1224 is fixed with respect to the outer tube 1212 at its proximal end and at its distal end. However it remains unattached in an intermediate portion between the proximal and distal end, e.g., along its length between its two fixed ends, so it can float within the outer tube 1212.

Figure 19A:
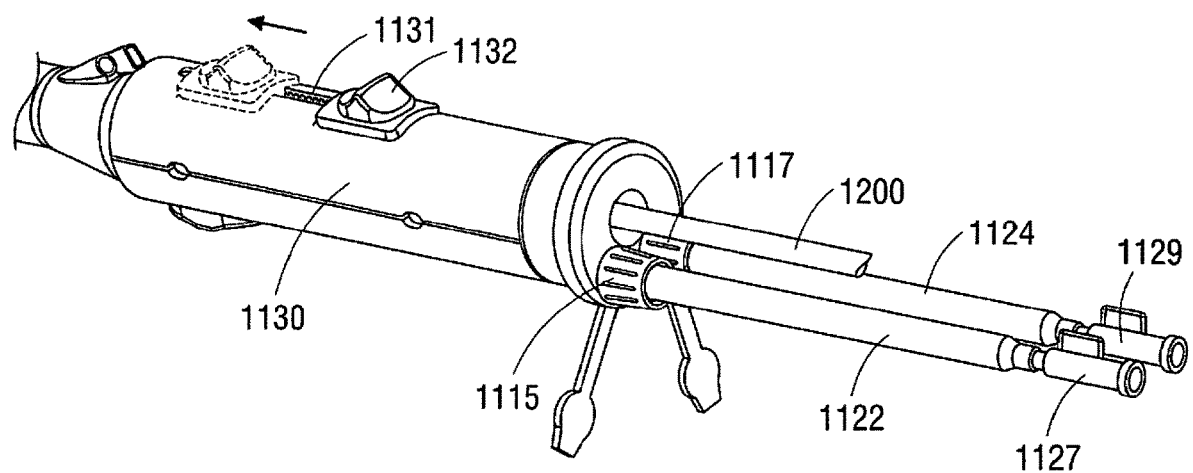
FIG. 19A is a perspective view illustrating the tool channels inserted into the catheter of FIG. 11
Figure 19B:
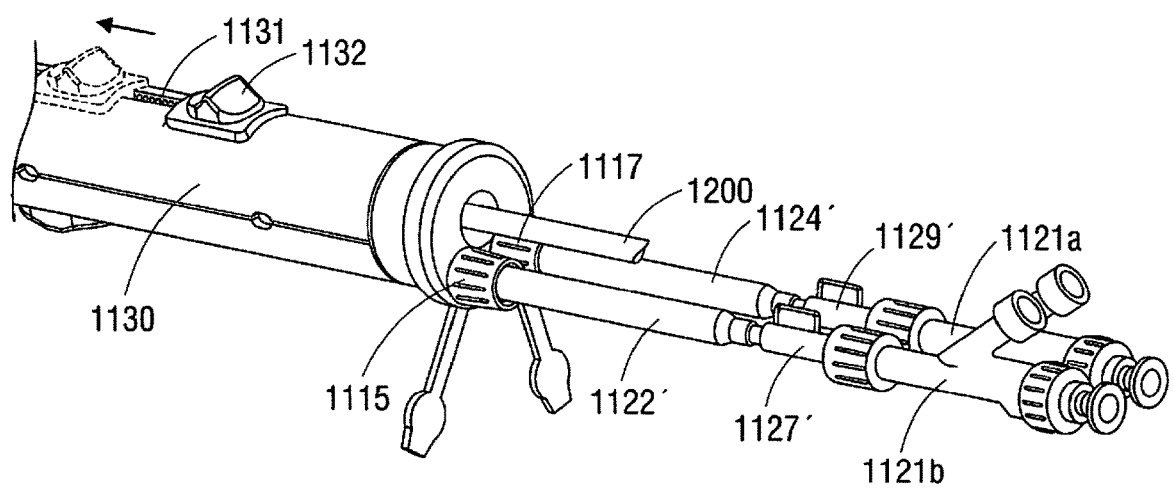
FIG. 19B is a perspective view illustrating an alternative embodiment of the tool channels.
Figure 20A:
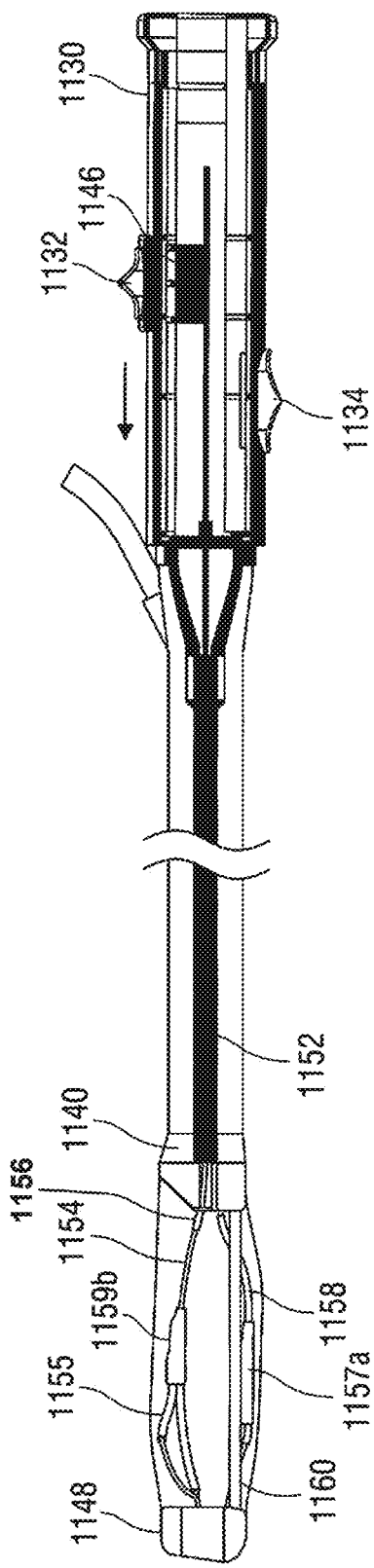
FIGS. 20A and 20B are side views in partial cross-section showing movement of the actuator from a proximal position to a distal position to move the retractor system to the expanded position.
Figure 20B:
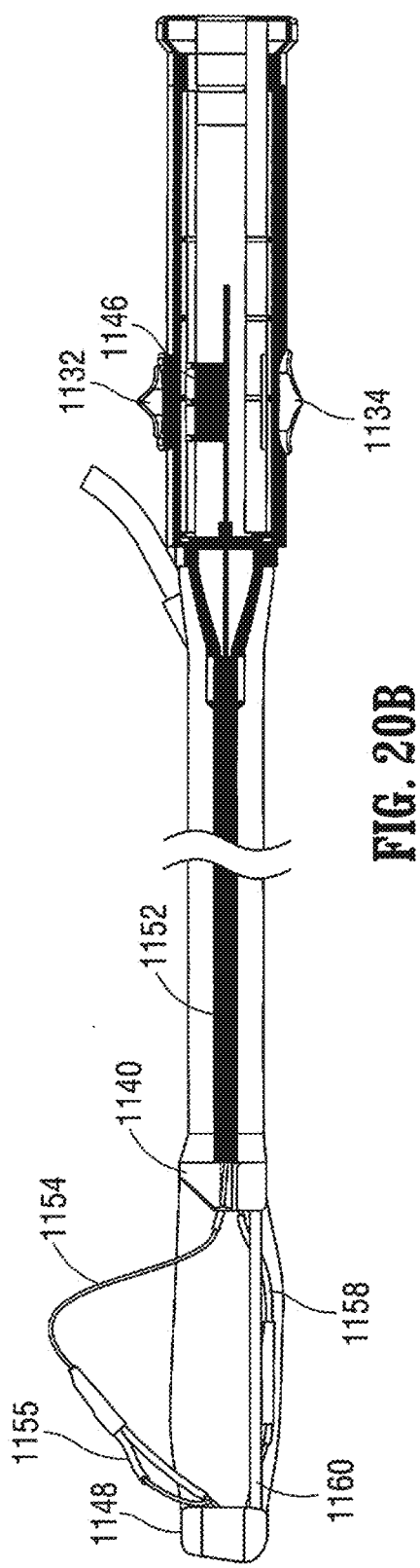

First and second flexible guides or tool channels 1271, 1270 (FIG. 33) are inserted through ports 1248 and 1250 in the same manner as flexible guides (tool channels) 1122, 1124 of FIG. 19A. The flexible guides 1271, 1270 extend through floating channels 1222, 1224, respectively, to emerge out the distal ends into the chamber. Note flexible guides 1271 and 1270 can in some embodiments be composed of a Pebax tubing, an overlying PVC tubing and polyolefin shrink tubing over the PVC tubing. The other flexible guides disclosed herein can also be composed of such structure. This provides a balance between flexibility and rigidity, and also beefs up the proximal end to facilitate handling by the user. Note the flexible guides 1271, 1270 emerge from the proximal cap 1218 and bend at their distal tips in the same manner as flexible guides (tool channels) 1122, 1124. Therefore, since the flexible guides 1271, 1270 are identical in function for guiding/bending working instruments inserted therethrough, for brevity they will not be discussed further since the discussion of flexible guides 1122, 1124 above is fully applicable to flexible guides 1271, 1270. Note for clarity the flexible guides are not shown in the other Figures, it being understood that they would function in the manner of FIGS. 21-25.

Figure 35A:
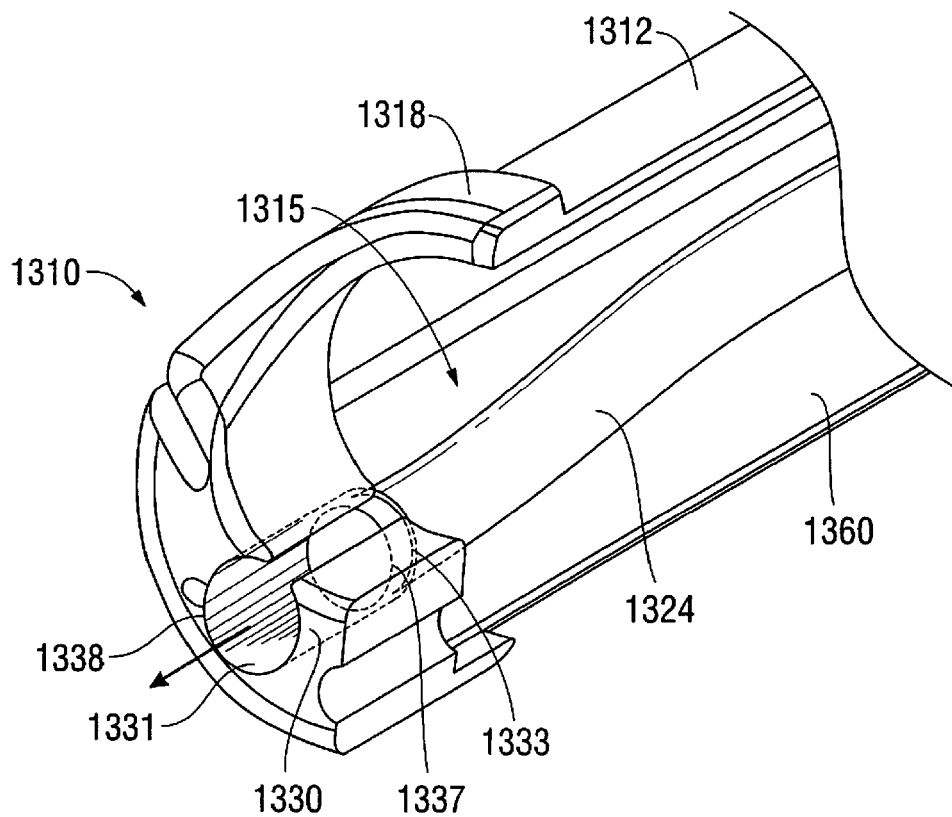
FIG. 35A is a view similar to FIG. 34 showing an alternate embodiment of the floating channel.
Figure 35B:
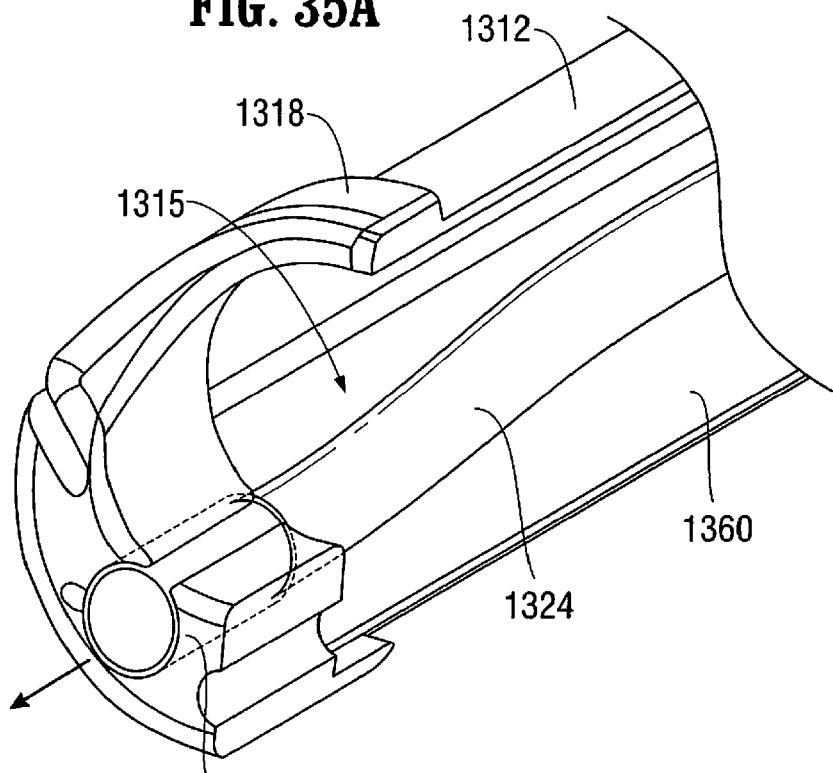
FIG. 35B is a view similar to FIG. 35A showing the floating channel advancing within the fixed distal tube.
Figure 35C:
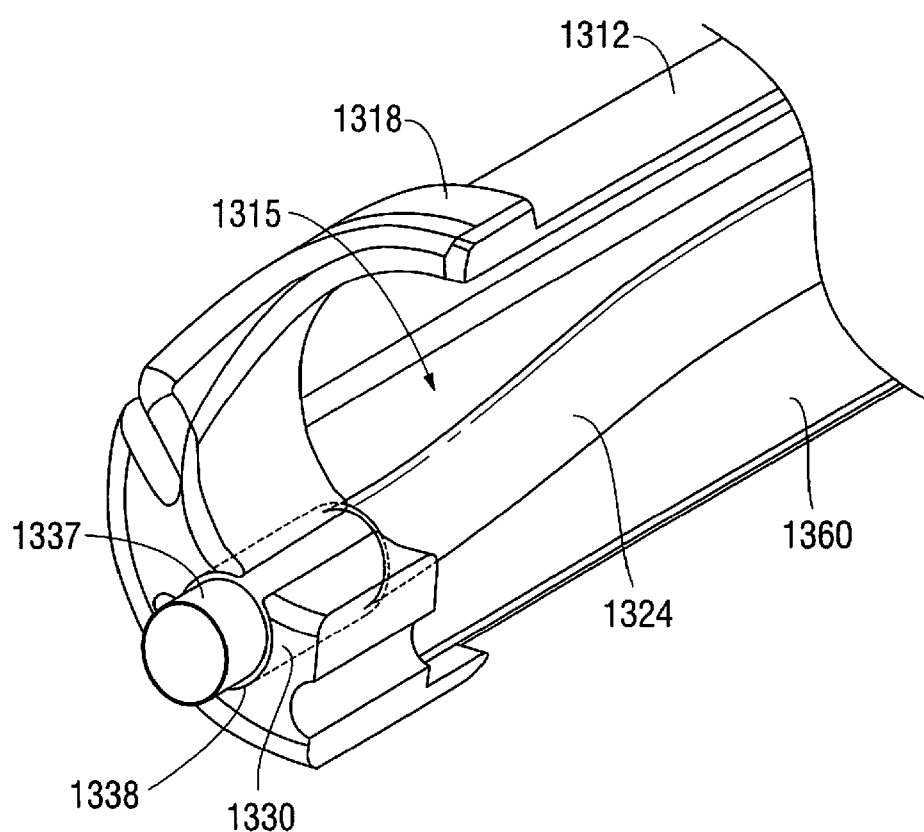
FIG. 35C is a view similar to FIG. 35B showing movement of the floating channel beyond the fixed distal tube.

In an alternate embodiment of FIGS. 35A-35C, the floating (flexible) channels are fixed at their proximal end but remain free (unattached) at their distal ends. More specifically, FIGS. 35A-35C illustrate a cutaway view of the system so that only one of the floating channels, the second floating channel 1324, is illustrated. The first floating channel is attached and configured in a similar fashion as second floating channel 1324. Second floating channel 1324 is attached at its proximal end in the same manner as floating channel 1224, i.e., attached within a fixed proximal tube. The first floating channel 1322 is not shown in FIGS. 35A-35C but is shown in FIG. 38 and is attached at its proximal end in the same manner as first floating channel 1222, i.e., attached within a fixed proximal tube. The floating channels 1322, 1324 differ from the floating channels 1222, 1224 of FIG. 32 in that they are unattached at their distal ends. Consequently, the floating channels 1322, 1324 form telescoping channels within the outer tube (or catheter) 1312.

More specifically, with continued reference to FIGS. 35A-35C and FIG. 38, a first fixed distal tube 1326 is attached within the outer tube 1312 adjacent proximal end cap 1318 positioned over the outer tube (catheter) 1312 of the system 1310. First fixed distal tube 1326 forms a pocket for the first floating channel 1322. Distal tube 1326 has a lumen extending therethrough, a proximal edge 1325 and a distal edge 1329. Preferably, distal edge 1329 is substantially flush with the distal edge of proximal end cap 1318. A second fixed distal tube 1330 is attached within outer tube 1312 adjacent the proximal end cap 1318 and forms a pocket for the second floating channel 1324. Distal tube 1330 has a lumen 1331 extending therethrough, a proximal edge 1333 and a distal edge 1338. Preferably distal edge 1338 is substantially flush with the distal edge of proximal end cap 1318. Second floating channel 1324 has a distal end 1337 which in the position of FIG. 35A is fully within the second fixed distal tube 1330. Upon bending of the outer tube 1312 in one direction, the second floating channel 1324 moves distally to the position of FIG. 35B. Upon additional bending, the floating channel 1324 can extend beyond the distal edge 1338 of the second fixed distal tube 1330 (and beyond the distal edge of the proximal end cap 1318) as shown in FIG. 35C. FIG. 38 (and FIG. 39B) illustrates the effect in bending of the outer tube 1312 in the opposite direction of FIG. 35C. As shown, the second floating channel 1324 remains within the lumen 1331 of the second fixed distal tube 1330 while the distal end 1327 of first floating channel 1322 extends distally beyond the distal edge 1329 of first fixed distal tube 1326 (and beyond the distal edge of the proximal end cap 1318).

Stated another way, the floating channels 1322, 1324 are unconstrained within outer tube (catheter) 1312 and take the shortest path when the outer tube 1312 is bent. Thus, the movement readjusts their position to adjust for the length difference on bending of the outer tube 1312. Note the floating channels 1322, 1324 can also slightly rotate during bending of the outer 1312 to compensate for stress applied to the floating channels during bending. Consequently, this prevents the eccentric positioned channels from being stretched on the outer portion of the curvature and buckling on the inner portion of the curvature. The floating channels can move around within lumen 1315 of outer tube 1312 and take any shape to accommodate bending to increase the flexibility of the device.

Note that in FIG. 35C the outer tube 1312 is bent in a first direction so that second floating channel 1324 on the inside curvature of the outer tube 1312 is advanced distally beyond distal tube 1330. In FIG. 38, the outer tube 1312 is bent in a second opposite direction so that the first floating channel 1322 on the inside curvature of the outer tube 1312 extends beyond the distal tube 1326.

The fixed distal tubes 1326, 1330 which form pockets for the respective floating channels 1322, 1324 are dimensioned so their length exceeds the largest extent of movement in response to the greatest curvature of the outer tube 1312 as a result of bending of the outer tube 1312 during use. This ensures that the floating channels 1322, 1324 will not retract out of the proximal end of the respective fixed distal tubes 1326, 1330, In a preferred embodiment, the length of the distal tubes 1326 and 1330 are between about 1.5 cm to about 3 cm, and preferably about 2 cm. Other dimensions are also contemplated.

Flexible guides identical to flexible guides 1270, 1271 of FIG. 33 and/or flexible guides 1122, 1124 of FIGS. 19-25 are inserted through the floating channels 1322 and 1324 in the same manner as described above so that endoscopic working instruments can be inserted into the chamber formed by the flexible elements for performing the procedure. Note, alternatively, endoscopic working instruments can be inserted directly through the floating channels of any of the embodiments herein without the intermediary flexible guides. Such direct insertion of instrumentation without flexible guides (tool channels) is also described above as an alternative system and method.

The working instruments can include graspers for example. A dissecting/cutting instrument can be inserted through the flexible guide in the floating channel, or alternatively inserted through a working channel of the endoscope. Thus, various working instruments can be inserted through the flexible channels and endoscope channel(s).

The flexible guides described herein, e.g., flexible guides 1270, 1271, can be color coded to improve the system's usability. For example, flexible guide 1270 can be of a first color, such as red, and flexible guide 1271 can be of a second color, such as black. In this way, when the user is manipulating the flexible guides 1270, 1271 at their proximal ends outside the patient's body, the user will more readily see the corresponding color coordinated tip being manipulated within the expanded cage. Note the entire flexible guide can have the same color or alternatively the matching color can be only at the proximal end visible to the user and the distal end visible by the endoscope. It should also be appreciated, that instead of color coding, other indicia can be provided so the user can match the proximal end of the flexible tube with the distal end within the chamber.

Figure 36:
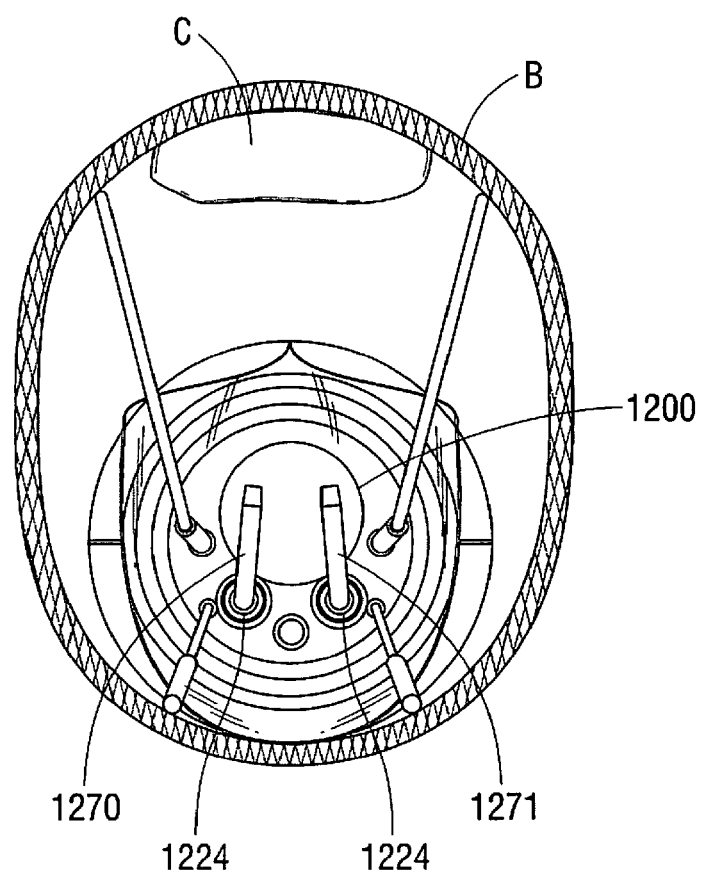
FIG. 36 is a front view of the system of FIGS. 32 and 33 shown within the colon.
Figure 39A:
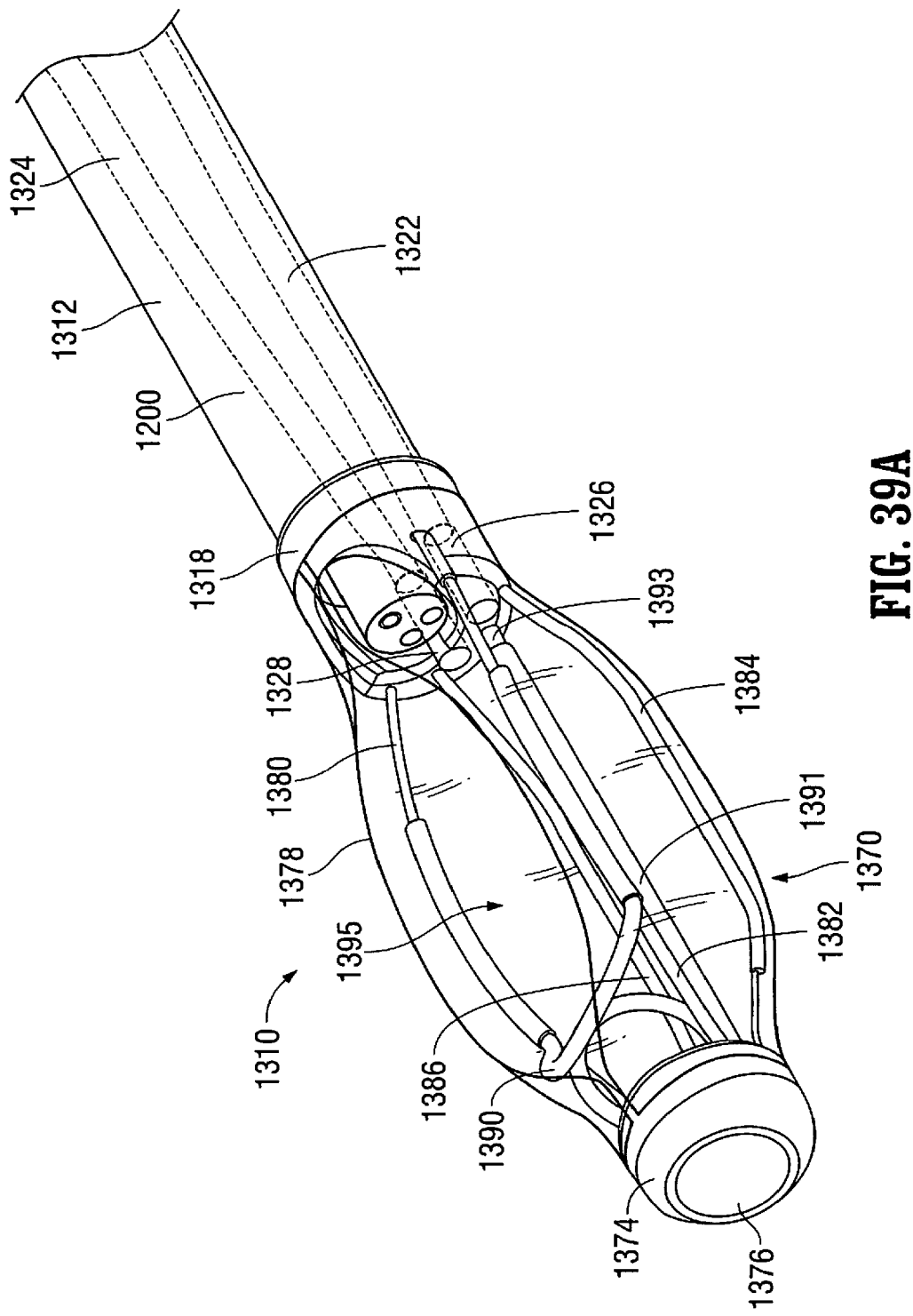
FIGS. 39A and 39B are side perspective views of the distal portion of the system of FIG. 38 showing the effect of bending of the outer tube and movement of the floating channels, and the retractor system shown in the non-expanded configuration.
Figure 39B:
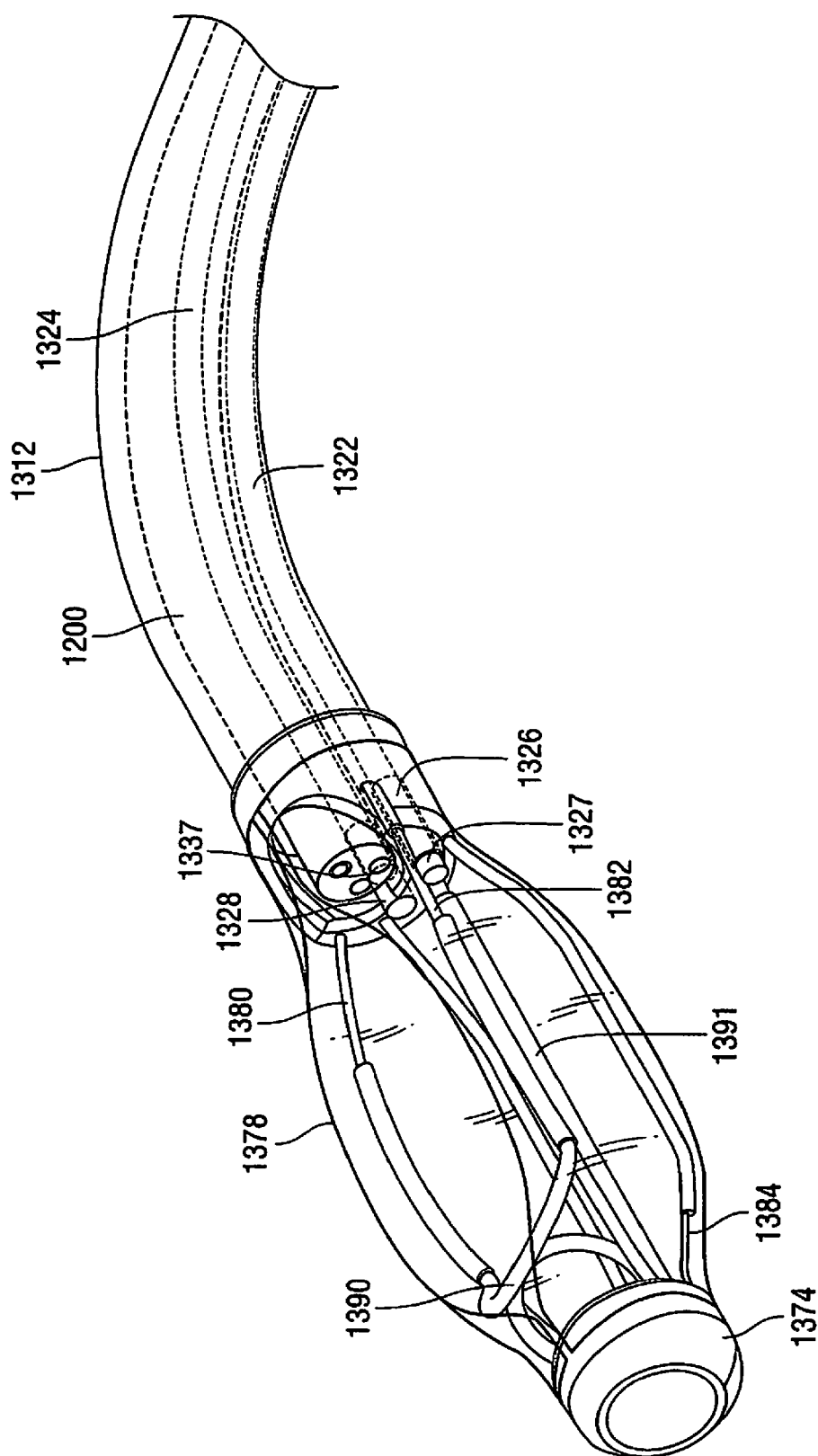
Figure 39C:
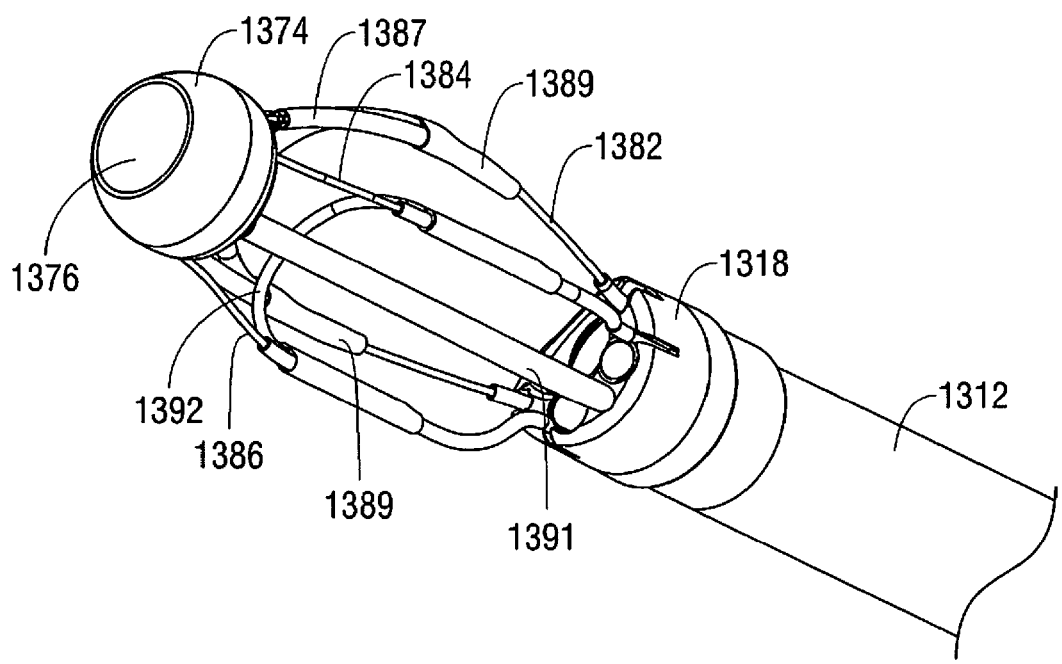
FIG. 39C is a bottom perspective view of the retractor system of FIG. 39A.

FIGS. 39A-39C illustrate the distal portion of the system 1310 to show the retractor elements in the expanded configuration to form the asymmetric cage to create a working space for the surgical procedure. The retractor system 1370 is identical to the retractor system 1150 of the embodiment of FIG. 21A and therefore when expanded from its collapsed insertion position forms a working space expanding system and in certain surgical procedures a body lumen reshaping system which reshapes the body lumen to form an asymmetric space to increase the working space for the maneuverability of the endoscopic instruments through the flexible guides of the system. That is, the retractor system creates a self-contained "surgical suite" which forms an expanded area within the body lumen for the surgeon to perform the surgical procedure within the created space. By reshaping the body lumen, the working space is maximized without overstretching the body lumen. Such working space maximization increases the distance between the target tissue and the end effectors of the endoscopic instruments, hence improving maneuverability of the instruments during the surgical procedure. Note the flexible tool channels (flexible guides) and endoscopic instruments are not shown in these drawings for clarity but would operate in the same manner as in FIGS. 21-25. The retractor system of system 1210 of FIGS. 32 and 33 is identical to the retractor system 1370 of system 1310 and therefore the discussion of the structure and function of the retractor system 1370 is fully applicable to the retractor system of system 1210. FIG. 36 discussed below illustrates an example of the reshaping of the body lumen to a more oval-like configuration.

As noted above, retractor system 1370 is identical to retractor system 1150 and includes flexible retractor elements 1380, 1382 which create the working chamber (space) within the body lumen and form an asymmetric cage. Flexible retractor elements 1384, 1386 form the base of the retractor system 1370. Movement of the retractor elements 1380, 1382, 1384 and 1386 is the same as retractor elements 1152, 1154, 1156 and 1158 described above and/or the same as movement of the retractor elements of FIGS. 40-42 described below. The retractor system 1370, also like retractor system 1150, can include a bridge member 1390 spanning retractor elements 1380, 1382 and optionally a bridge member 1392 spanning retractor elements 1384, 1386, which are configured and function in the same manner as aforedescribed bridge members 1155, 1157 and therefore for brevity are not described herein again in detail as the description above for bridge members 1155, 1157 and their alternatives are fully applicable to the retractor system 1370.

The retractor elements 1380, 1382, 1384, 1386 can be made of substantially flexible materials and are preferably formed of a wire composed of nitinol. A layer of soft compatible material, but preferably PTFE tubing 1387, can be positioned over a portion of the wires. A polyolefin heat shrink 1389 can be positioned over the retractor portion of the elements and bridge member to retain the bridge members. Note the retractor elements angulate at the distal end, i.e., pivot from the distal cap 1374. To bulk up the retractor elements adjacent this region, a covering material such as the PTFE tubing can be provided.

Flexible tube or beam 1391 in the form of a rod or tube has a lumen to receive a stabilizing or rigidifying structure such as rigid tube or rod 1393. (Alternatively, the rigid tube or rod can be slid over beam 1391). Flexible beam 1391 and rigidifying structure 1393 are identical to flexible beam 1160 and rigid beam 1162 of FIGS. 17A, 17B described above. Therefore, for brevity, further details of these components are not provided herein since the structure and function of the beams 1160, 1162 provided in detail above are fully applicable to the beams 1391, 1393. An actuator like actuator 1256 of FIG. 33 is operably connected to the rod 1393 for sliding movement with respect to beam 1391 to increase the rigidity of the cage. Alternative structure for the rigidifying structure described above, such as sliding a rigidifying structure over a flexible beam, are also fully applicable as alternatives to the rigidifying structure of the retractor system 1370 of FIG. 39A and the retractor system of the system 1210 of FIGS. 32 and 33.

Figure 28:
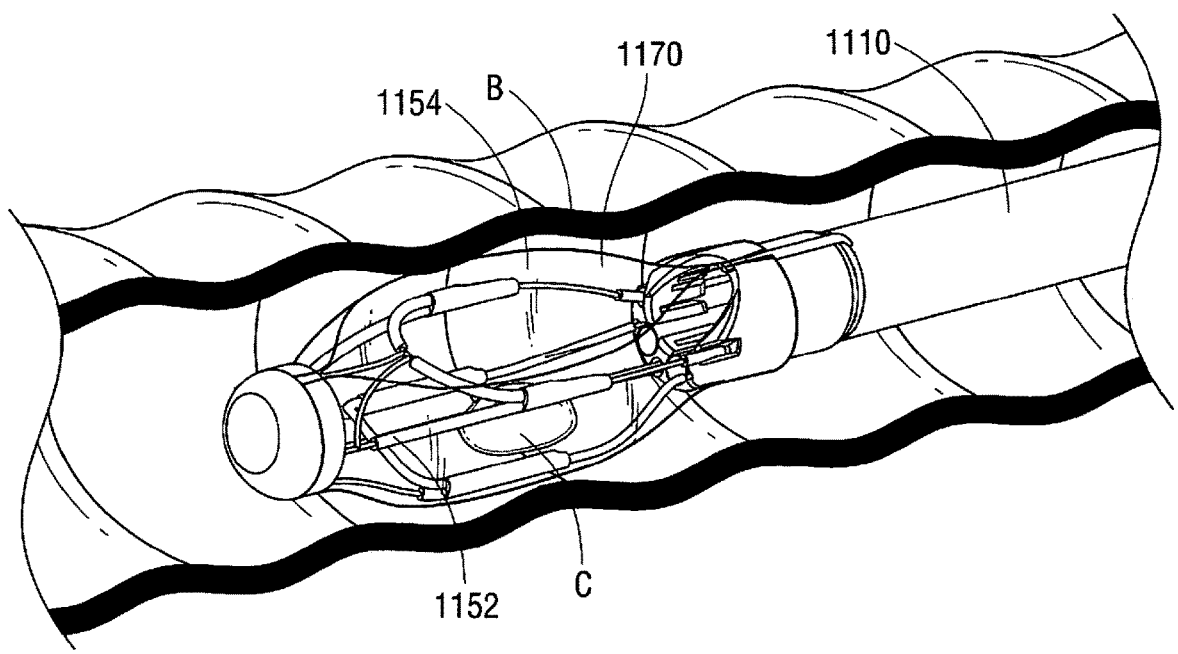
FIG. 28 is a view similar to FIG. 26 showing the retractor system in the collapsed position.
Figure 29:
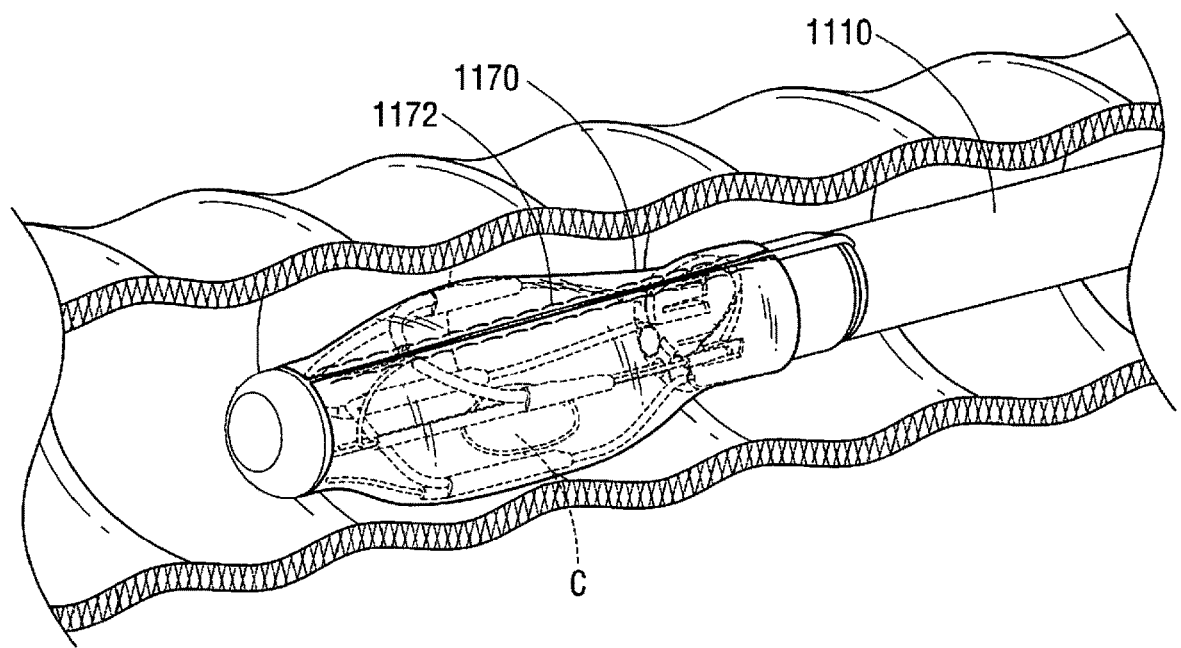
FIG. 29 is a view similar to FIG. 28 showing the covering member closed to encapsulate the lesion for removal.

A covering or cover 1378 identical to cover 1170 of FIGS. 28 and 29 of Figure is provided. The cover 1378 covers the retractor elements 1380, 1382, 1384, 1386 and in the expanded position of the retractor system 1370 has an opening 1395 for access to the tissue. Further details of the cover 1395 are not provided herein since the cover 1395 is identical in structure and function to cover 1170. Also, the various embodiments of the covers described above are fully applicable to the cover for the systems of FIGS. 32-42.

In alternate embodiments, the pursestring to close the cover 1378 of FIG. 32-42 or the cover of any over the aforedescribed covers is eliminated and reliance is on the cover itself. Elimination of the pursestring simplifies the device by providing fewer components and reduces the steps in the surgical procedure. In embodiments without the pursestring, when the tissue, e.g., the severed polyp, is pulled into the cage formed by the retractor elements, and the retractor elements return to their non-expanded position to collapse the cage, the cover closes down on the captured tissue, e.g., the polyp, to prevent or minimize seeding of the pathological tissue, e.g., cancerous tissue, during removal. The grasper can also maintain its grip on the severed tissue so the grasped tissue and catheter are removed together from the body lumen. The target tissue, e.g., polyp, during the procedure and during its removal from the body would typically be located inside the cage and practically isolated by the cage and its cover from the surrounding innocent tissues.

Figure 40:
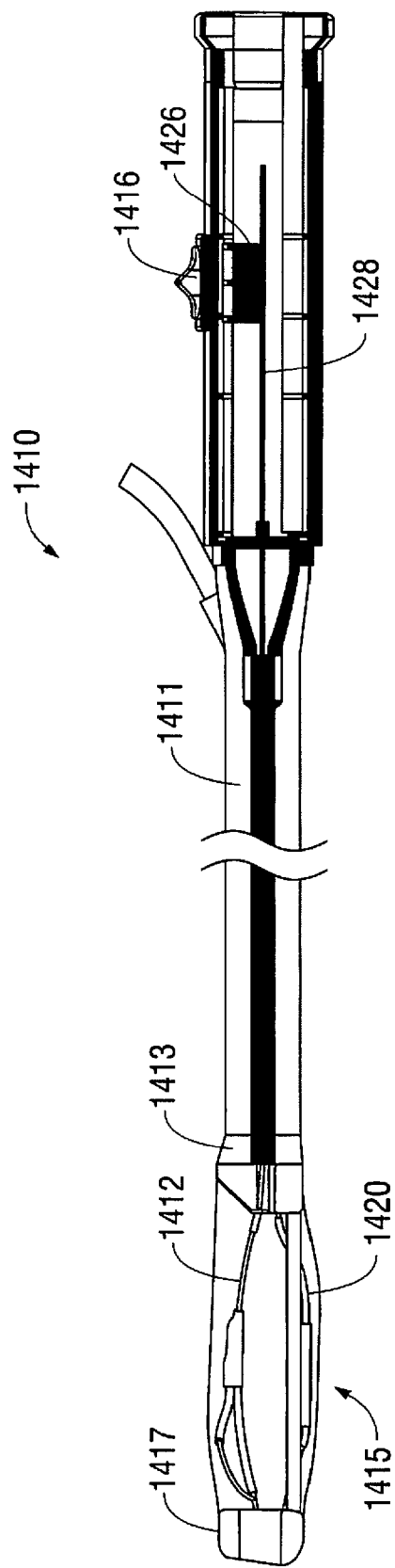
FIG. 40 is a longitudinal cross-sectional view of an alternate embodiment of the system with the retractor system shown in the collapsed insertion position.
Figure 41:
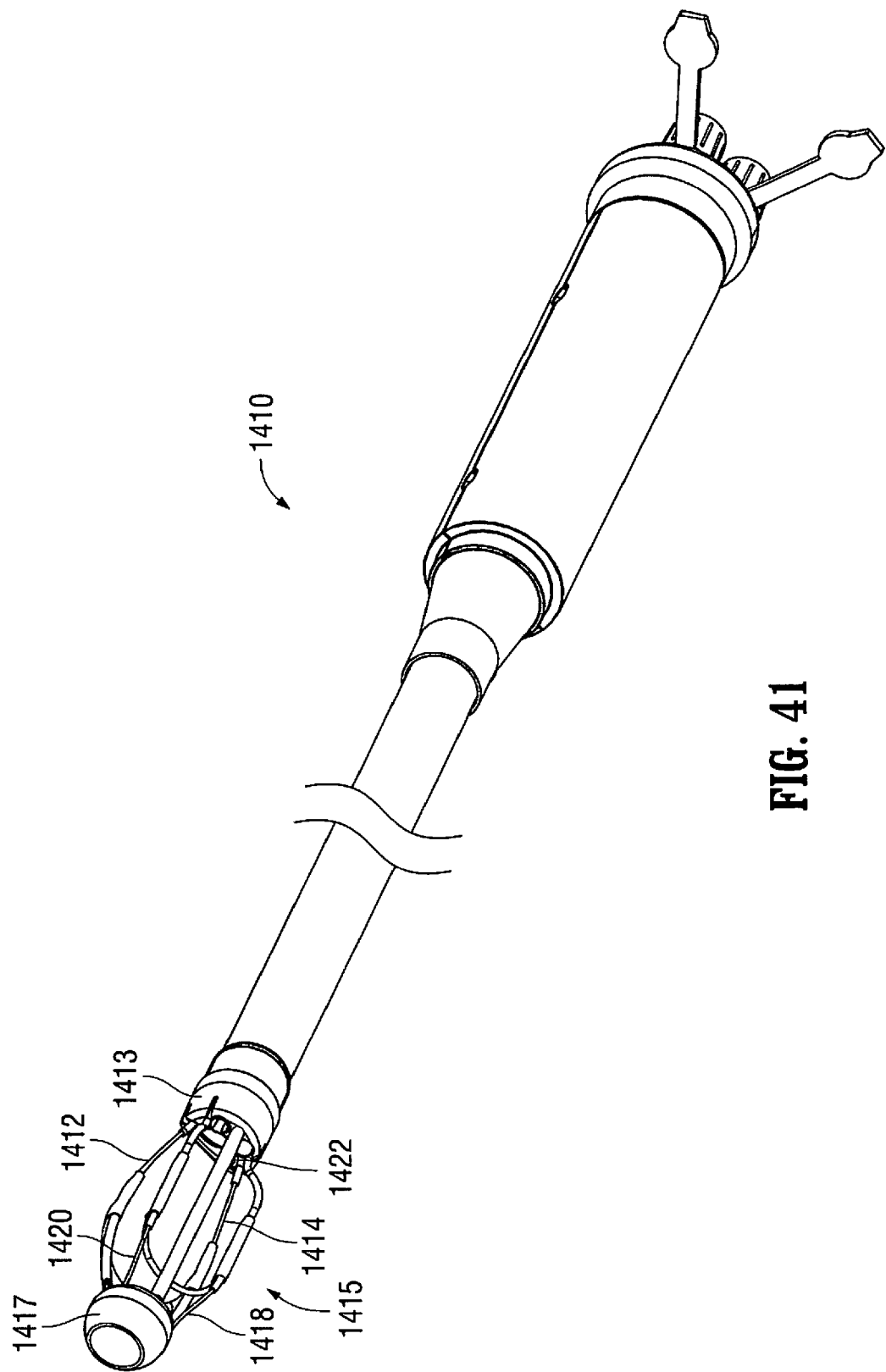
FIG. 41 is a bottom perspective view of the system of FIG. 40 with the retractor system shown in the non-expanded configuration.
Figure 42:
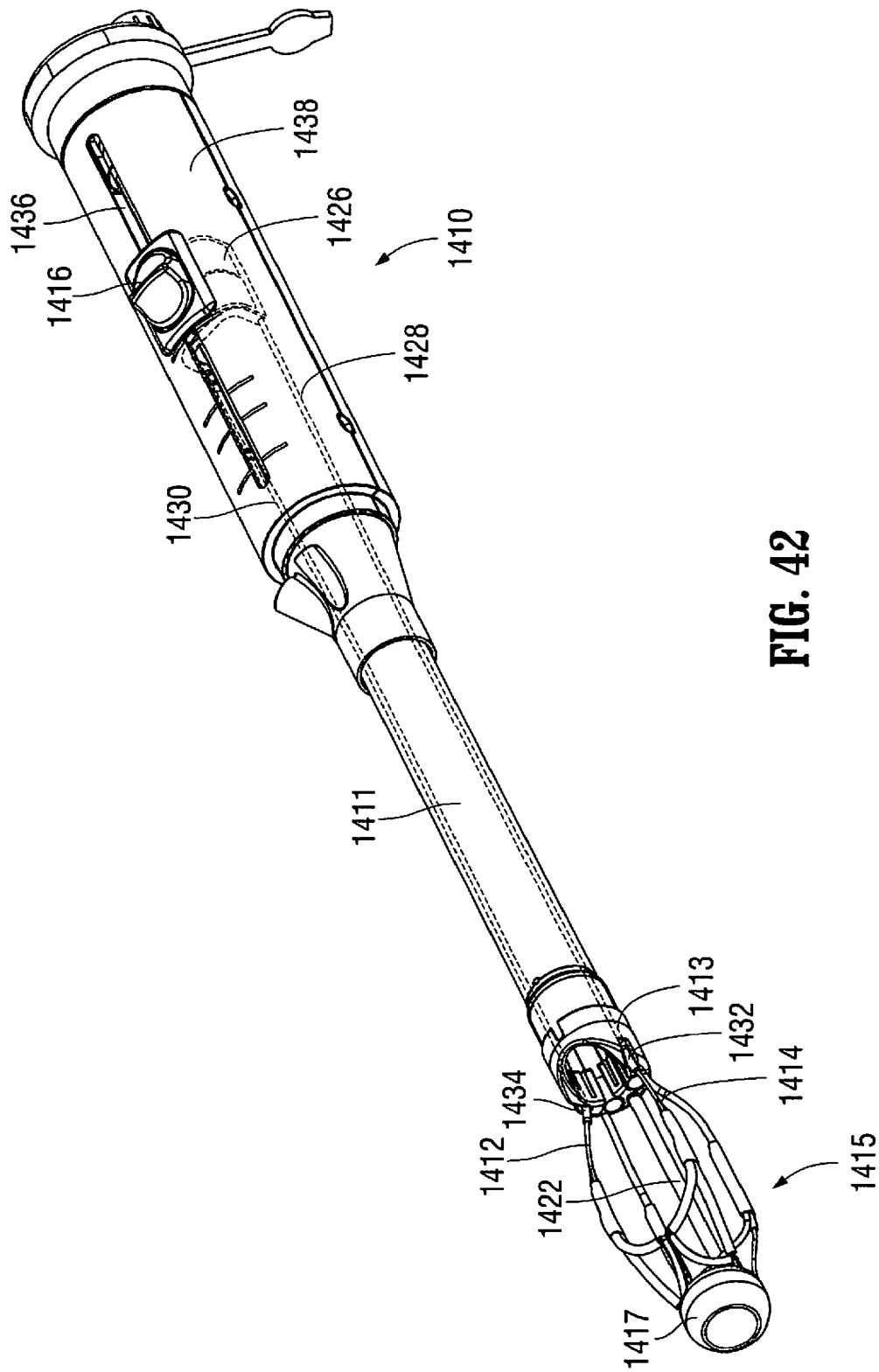
FIG. 42 is a side perspective view of the system of FIG. 41.

FIGS. 40-42 illustrate an alternative retractor system of the present invention. The retractor system 1415 of system 1410 is identical to the retractor system 1370 FIG. 39A (and system 1150 of FIG. 17C) except for the rigidifying structure. In this embodiment, instead of a movable beam to stiffen an otherwise flexible element, an element of the retractor system has inherent stiffness characteristics to stiffen the overall retractor system 1415. More specifically, retractor system 1415 has flexible retractor elements 1412, 1414 which expand (bow outwardly) to form the chamber (cage) to create the working space in the same manner as retractor elements 1380, 1382 described above. These flexible elements 1412, 1414 are expanded by movement of actuator 1416 in the same manner that movement of actuator 1252 (FIG. 33) expands flexible retractor elements 1380, 1382. That is, actuator 1416 is attached to block or carriage 1426 which contains a slot or opening for attachment of push cable 1428. Push cable 1430 is also attached within another slot or opening of block 1426. Thus, push cables 1428, 1430 are operatively connected at their proximal ends to actuator 1416. A connection tube 1432 connects push cable 1428 to flexible element 1414 and connection tube 1434 connects push cable 1430 to flexible element 1412. The connection tubes 1432, 1434 are at the distal end of the outer tube 1411 at the region of the proximal cap 1413. More specifically, a distal end of push cable 1428 is secured within connection tube 1432 and a proximal end of flexible retractor element 1414 is secured within connection tube 1432. A distal end of push cable 1430 is secured within connection tube 1434 and a proximal end of flexible retractor element 1412 is secured within connection tube 1434. Slidable advancement of actuator 1416 within slot 1436 of handle housing 1438 moves push cables 1428, 1430, distally which bows flexible elements 1412, 1414 outwardly to an expanded position due to their attachment at distal end cap 1417. Markings 1440 can be provided to indicate retractor element expansion as in FIG. 33.

Retractor system 1410 also has flexible elements 1418, 1420 forming the base of the cage and identical to retractor elements 1384, 1386 described above. Retractor system 1415, however, differs from retractor system 1370 (and 1150) in that a beam 1422 is provided which itself has sufficient rigidity to maintain the overall stiffness of the expanded cage when fairly mild forces are applied (e.g., weight of small portion of the intestinal wall, minor external intra-abdominal pressure, etc.) and limit bending of the cage with respect to the outer tube 1422 during use when fairly mild forces are applied. That is, the beam 1422 extending from the proximal cap 1413 to the distal cap 1417 maintains the rigidity of the system when fairly mild forces are applied as it is fixed at both ends and extends the length of the expanded cage. The rigidity of the beam 1422, however, is optimized to be sufficiently flexible when fairly significant force is applied to it (e.g., bending force of the endoscope). This rigidifying of the beam can be achieved in several ways. In some embodiments, the wire element which forms the rigidifying beam itself is sufficiently rigid to achieve the stability of the expanded cage. However, to further increase the rigidity, but preserve the desired flexibility, the rigidifying beam in alternate embodiments can have an increased thickness to further optimize the bending of the cage's elements such as beam 1422. As shown, in this embodiment, the diameter or (cross-sectional dimension if a non-circular beam is used) is greater than the diameter (or cross-sectional dimension if non-circular elements are used) of the flexible elements 1412, 1414, 1418, and/or 1420. In other embodiments, the rigidifying beam can be composed of a stiffer material than one or more of the other flexible elements. Such stiffer materials can include for example steel or plastic.

Note the flexible tool guides (tool channels) are not shown in FIGS. 40-42 for clarity, but flexible guides such as flexible guides 1270, 1271 of FIG. 33 can be utilized. Also, in this embodiment only a single actuator is provided for expansion of the retractor system 1415 since an actuator for rigidifying the structure is not necessary.

In all other respects, system 1410 is identical to system 1310.

Note as shown in FIG. 36, the retractor elements of the embodiments disclosed herein form an asymmetric cage to create a working space or working chamber for performance of the surgical procedure. The chamber facilitates instrument maneuverability, for example instruments' triangulation as described above. Note the asymmetric chamber causes a reconfiguration of the body lumen or working space without stretching the body lumen wall beyond a point when it can be injured, e.g., lacerated by the stretching force. Such reconfiguring can be appreciated by reference to FIG. 36 where the body lumen has changed from a substantially circular cross-sectional configuration to a somewhat oval shape configuration where the walls are elongated as shown. As can be appreciated, this increases the distance from the tips of the working instruments to the targeted tissue, such as the polyp C on the wall of the colon B. Thus, the retractor elements change the colon shape at the desired site to a narrower width, particularly at the bottom of the chamber, and taller in height (in the orientation of FIG. 36) to increase working space for the instruments thereby reconfiguring the colon lumen.

The retractor elements of the embodiments disclosed herein also stabilize the luminal wall motion which may be more prominent in the gastrointestinal tract. This may facilitate the surgical procedure, particularly in the gastrointestinal tract.

Note that the various embodiments of the cage described above are expandable to alter the working space within the body space or body lumen. As the cage is expanding, the working space around the target tissue, e.g., lesion, is increasing. More specifically, the distance between the instruments and the target tissue is increasing, hence, facilitating the instruments' maneuverability and ability to perform more advanced surgical techniques inside the lumen, e.g., tissue retraction, dissection, repair. As the cage expands it may press on and deflect at least a portion of the luminal wall. As a result, the shape of the lumen can be changed depending on the size and shape of the cage, the extent of its expansion and the size and shape of the body lumen. In smaller diameter body lumens, such as the bowel, the expansion of the cage may substantially reshape the body lumen as described above. This reshaping can also occur in larger diameter body lumens. However, it should also be appreciated that in certain larger diameter body lumens, such as the stomach, and especially when insufflation is utilized for the surgical procedure, the body lumen may not necessarily be reshaped. For example, the cage may only contact one side of the body lumen wall. However, even in this case, the expanded cage applies a radial force against the body wall to alter the working space. Therefore, whether the cage is used in small or larger diameter working spaces/lumens it advantageously moves at least one side of the wall to increase the distance between the tips of the instruments and the target tissue, thereby functioning as a working space expanding system to facilitate access and maneuverability as described in detail above. As can also be appreciated, the dynamic nature of the cage with its controlled expansion enables the system to function as an organizer to adjust and optimize the distance between the tips of the instruments and the target tissue. Also note that in larger diameter body lumens a symmetric cage might also be able to be utilized, although not optimal.

Note the endoscopic instruments can be used for partial tissue resection, for example, submucosal or subserosal resection. The endoscopic instruments could also be utilized for full thickness tissue resection. The instruments enable removal of the lesion with healthy tissue margins, thereby providing a complete, en-block removal of the pathological lesion.

Without intending to be limited to any theory or mechanism of action, the above teachings were provided to illustrate a sampling of all possible embodiments rather than a listing of the only possible embodiments. As such, it should be appreciated that there are several variations contemplated within the skill in the art that will also fall into the scope of the claims.

We claim:
1. A minimally invasive surgical system, comprising:
   a flexible catheter having an inner wall, an outer wall, and a first lumen;
   a floating channel disposed within the first lumen, the floating channel being free to move radially within the first lumen along a length of the flexible catheter;
   a working space altering system positioned at a distal portion of the flexible catheter, the working space altering system movable from a non-expanded insertion position to an expanded position forming an expanded region, the working space altering system comprising a plurality of flexible elements; and
   a coupler to retain a distal portion of the first and second flexible elements, wherein the coupler include a lumen dimensioned to receive an endoscope therethrough,
   wherein the first lumen is configured and dimensioned to receive a first instrument for axial movement therein, the first instrument having a longitudinal axis and a distal portion movable to an angled position with respect to the longitudinal axis in the expanded region, and
   wherein the coupler includes a lumen dimensioned to receive an endoscope therethrough.
2. The surgical system of claim 1, wherein the first lumen is configured and dimensioned to receive the first instrument and a second instrument for axial movement therein, the second instrument having a longitudinal axis and a distal portion movable to an angled position with respect to the longitudinal axis in the expanded region.

3. The surgical system of claim 1, comprising a second lumen, wherein the second lumen is configured and dimensioned to receive a second instrument for axial movement therein, the second instrument having a longitudinal axis and a distal portion movable to an angled position with respect to the longitudinal axis in the expanded region.

4. The surgical system of claim 3, comprising the first instrument.

5. The surgical system of claim 4, comprising the second instrument.

6. The surgical system of claim 3, wherein the first instrument is an endoscope.

7. The surgical system of claim 6, wherein the second instrument is an endoscopic stapler, a tissue loop, a clip applier, a suture delivering instrument, a cutter, or an energy-based tissue coagulator.

8. The surgical system of claim 1, wherein the floating channel comprises a first tube coupled to a distal end of the flexible catheter.

9. The surgical system of claim 1, wherein first and second flexible elements expand radially responsive to moving the working space altering system to the expanded position.

10. The surgical system of claim 9, wherein at least one of the flexible elements has a rigidity sufficient to stabilize the working space altering system.

11. A minimally invasive surgical system, comprising:
a flexible catheter having an inner wall, an outer wall, and a first lumen;
a floating channel disposed within the first lumen, the floating channel being free to move radially within the first lumen along a length of the flexible catheter;
a working space altering system positioned at a distal portion of the flexible catheter, the working space altering system comprising a plurality of flexible elements; and
a coupler to retain a distal portion of at least a first and a second flexible element of the plurality of flexible elements,
wherein the first and the second flexible elements of the plurality of flexible elements expand radially responsive to moving the working space altering system from a non-expanded position to an expanded position to forming an expanded region,
wherein the first lumen is configured and dimensioned to receive a first instrument for axial movement therein, the first instrument having a longitudinal axis and a distal portion movable to an angled position with respect to the longitudinal axis in the expanded region,
wherein at least one of the flexible elements has a rigidity sufficient to stabilize the working space altering system, and
wherein the coupler includes a lumen dimensioned to receive an endoscope therethrough.

12. The surgical system of claim 11, wherein at least one of the flexible elements has a rigidity sufficient to stabilize the working space altering system.

13. The surgical system of claim 11, comprising the first instrument.

14. The surgical system of claim 11, wherein the first instrument is an endoscope, an endoscopic stapler, a tissue loop, a clip applier, a suture delivering instrument, a cutter, or an energy-based tissue coagulator.

15. A minimally invasive surgical system, comprising:
a flexible catheter having an inner wall, an outer wall, a first lumen, and a second lumen;
a floating channel disposed within the first lumen, the floating channel being free to move radially within the first lumen along a length of the flexible catheter; and
a working space altering system positioned at a distal portion of the flexible catheter, the working space altering system movable from a non-expanded insertion position to an expanded position forming an expanded region, the working space altering system comprising at least first and second flexible elements configured to expand radially responsive to moving the working space altering system to the expanded position; and
a coupler to retain a distal portion of the first and second flexible elements,
wherein the coupler includes a lumen dimensioned to receive an endoscope therethrough,
wherein the first lumen is configured and dimensioned to receive a first instrument for axial movement therein, the first instrument having a longitudinal axis and a distal portion movable to an angled position with respect to the longitudinal axis in the expanded region, and
wherein the second lumen is configured and dimensioned to receive a second instrument for axial movement therein, the second instrument having a longitudinal axis and a distal portion movable to an angled position with respect to the longitudinal axis in the expanded region.

16. The surgical system of claim 15, wherein the first instrument is an endoscope.

17. The surgical system of claim 16, wherein the second instrument is an endoscopic stapler, a tissue loop, a clip applier, a suture delivering instrument, a cutter, or an energy-based tissue coagulator.

* * * * *